United States Patent
Gunde et al.

(10) Patent No.: US 11,319,371 B2
(45) Date of Patent: *May 3, 2022

(54) ANTI-CD3 ANTIBODIES

(71) Applicant: Numab Therapeutics AG, Wädenswil (CH)

(72) Inventors: Tea Gunde, Zurich (CH); Christian Hess, Zurich (CH); Sebastian Meyer, Eggenwil (CH); Alexandre Simonin, Rosenau (FR); Teddy Beltrametti, Schattdorf (CH); David Urech, Jona (CH)

(73) Assignee: Numab Therapeutics AG, Wädenswil (CH)

( * ) Notice: Subject to any disclaimer, the term of this patent is extended or adjusted under 35 U.S.C. 154(b) by 148 days.

This patent is subject to a terminal disclaimer.

(21) Appl. No.: 16/619,121

(22) PCT Filed: Jun. 4, 2018

(86) PCT No.: PCT/EP2018/064630
§ 371 (c)(1),
(2) Date: Dec. 4, 2019

(87) PCT Pub. No.: WO2018/224441
PCT Pub. Date: Dec. 13, 2018

(65) Prior Publication Data
US 2020/0115449 A1    Apr. 16, 2020

Related U.S. Application Data

(60) Provisional application No. 62/515,293, filed on Jun. 5, 2017.

(30) Foreign Application Priority Data

Nov. 27, 2017  (EP) .................................... 17203832

(51) Int. Cl.
*C07K 16/28* (2006.01)
*C07K 16/32* (2006.01)

(52) U.S. Cl.
CPC ...... *C07K 16/2809* (2013.01); *C07K 16/2866* (2013.01); *C07K 16/32* (2013.01); *C07K 2317/24* (2013.01); *C07K 2317/31* (2013.01); *C07K 2317/33* (2013.01); *C07K 2317/567* (2013.01); *C07K 2317/622* (2013.01); *C07K 2317/626* (2013.01); *C07K 2317/75* (2013.01); *C07K 2317/92* (2013.01); *C07K 2317/94* (2013.01)

(58) Field of Classification Search
CPC ............ C07K 16/2809; C07K 16/2866; C07K 16/32; C07K 2317/31; C07K 2317/567; C07K 2317/626; C07K 2317/92
See application file for complete search history.

(56) References Cited

U.S. PATENT DOCUMENTS

2020/0181263 A1* 6/2020 Urech .................... A61P 35/00

FOREIGN PATENT DOCUMENTS

| WO | 2010/037835 A2 | 4/2010 |
|----|----|----|
| WO | 2012/143524 A2 | 10/2012 |
| WO | 2015/063339 A1 | 5/2015 |
| WO | 2015/181098 A1 | 12/2015 |
| WO | 2016/014974 A2 | 1/2016 |
| WO | 2016/020444 A1 | 2/2016 |
| WO | 2016/071355 A1 | 5/2016 |
| WO | 2016/184570 A1 | 11/2016 |
| WO | 2017/023761 A1 | 2/2017 |

OTHER PUBLICATIONS

International Search Report, International Application No. PCT/EP2018/064630 (published under WO 2018/224441), 4 pages (dated Jul. 25, 2018).
Bortoletto et al, "Optimizing anti-CD3 affinity for effective T cell targeting against tumor cells," Eur. J. Immunol., vol. 32, No. 11, pp. 3102-3107 (Nov. 1, 2002).
Lopez-Albaitero et al., "Overcoming resistance to HER2-targeted therapy with a novel HER2/CD3 bispecific antibody," OncoImmunology, vol. 6, No. 3, 12 pages (Mar. 4, 2017).

* cited by examiner

*Primary Examiner* — Brad Duffy
*Assistant Examiner* — Cheom-Gil Cheong
(74) *Attorney, Agent, or Firm* — Prismatic Law Group, PLLC; Ron Kamis

(57) ABSTRACT

The present invention relates to novel antibodies that are specific for human CD3, in particular for the CD3ε domain.

16 Claims, 11 Drawing Sheets

Specification includes a Sequence Listing.

ANTI-CD3 ANTIBODIES

CROSS-REFERENCE TO RELATED APPLICATIONS

This application is a 371 national phase of International Patent Application No. PCT/EP2018/064630 filed Jun. 4, 2018, which claims priority to U.S. Provisional Patent Application No. 62/515,293 filed Jun. 5, 2017, and European Patent Application No. 17203832.5 filed Nov. 27, 2017, the content of which applications is incorporated herein by reference.

INCORPORATION OF SEQUENCE LISTING:

This application contains a sequence listing submitted electronically via EFS-web, which serves as both the paper copy and the computer readable form (CRF) and consists of a file entitled "WR-N13-NP_seqlist_2.txt", which was created on Oct. 1, 2021, which is 63,172 bytes in size, and which is herein incorporated by reference in its entirety.

FIELD OF THE INVENTION

The present invention relates to novel antibodies that are specific for human CD3, in particular for the CD3ε domain.

BACKGROUND OF THE INVENTION

This invention relates to novel anti-CD3 antibodies, in particular antibodies directed against the CD3ε domain, which combine high affinity with high potency, and in particular novel antibodies with an improved specificity and cross-reactivity profile.

The T cell receptor or TCR is a molecule found on the surface of T lymphocytes (or T cells) that is responsible for recognizing antigens bound to major histocompatibility complex (MHC) molecules on the surface of antigen presenting cells (APC). The binding between TCR and antigen is of relatively low affinity. When the TCR engages with antigen and MHC, the T lymphocyte is activated through a series of biochemical events mediated by associated enzymes, co-receptors, specialized accessory molecules, and activated or released transcription factors.

The TCR is associated with other molecules like CD3, which possesses three distinct chains (γ, δ, and ε) in mammals, and either a ζ2 (CD247) chain or a ζ/η chain. These accessory molecules have transmembrane regions and are vital to propagating the signal from the TCR into the cell; the cytoplasmic tail of the TCR is extremely short, making it unlikely to participate in signaling. The CD3- and ζ-chains, together with the TCR, form what is known as the T cell receptor complex.

CD3ε is a type I transmembrane protein expressed on the surface of certain T cells. It participates in the T cell receptor (TCR) complex and interacts with other domains of this complex. One of these interaction partners is CD3γ, which binds to CD3ε in a 1:1 stoichiometry (De la Hera et al, J. Exp. Med. 1991; 173: 7-17). It is believed that binding of the TCR to the MHC-peptide complex on the surface of an antigen presenting cell (APC) and subsequent movement of the T cell along the APC leads to a certain rotation of the TCR complex resulting in a dislocation of CD3ε and CD3γ relative to each other, which is required for efficient TCR signaling and therefore activation of T-cells. Certain antibodies against CD3ε have been demonstrated to induce TCR signaling while others did not. TCR-activating antibodies typically bind to an exposed epitope on CD3ε, whereas some non-stimulatory antibodies have been demonstrated to bind to the interface between CD3ε and CD3γ, or to concomitantly bind to CD3ε and CD3γ, thus possibly interfering with the relative displacement of CD3ε and CD3γ (Kim et al, JBC. 2009; 284: 31028-31037).

It is well established that peptide-MHC complexes bind TCR with low affinity and fast off-rate (Matsui et al, Science. 1991; 254: 1788-1791; Weber et al, Nature. 1992; 356: 793-796). It has been suggested that this low affinity is instrumental to allow a few peptide-MHC complexes to serially trigger many TCRs (Valitutti et al, Nature. 1995; 375: 148-151) by repeated binding and dissociation. This serial triggering is critical to sustain signaling over time, allowing T cells to eventually reach the activation threshold (Valitutti et al, Immunol. Today. 1997; 18: 299-304; Lanzavecchia et al, Cell. 1999; 96: 1-4). This notion is supported by the finding that, when compared to peptide-MHC complexes, high-affinity anti-CD3 antibodies do not efficiently stimulate T cells, since they trigger TCR with a 1:1 stoichiometry (Viola et al, Science 1996; 273: 104-106), suggesting that low-affinity antibodies may be more effective in stimulating T cells via TCR signaling because of their ability to repeatedly dissociate and re-bind to CD3ε. Indeed, in a direct comparison of three derivatives of the anti-CD3ε antibody TR66, which all bind with different affinities, wild-type TR66 having an intermediate affinity showed best efficacy in T cell activation when compared to its derivatives that have either higher or lower affinities (Bortoletto et al, J. Immuno. 2002; 32:3102-3107). Thus, a $K_D$ at around that of TR66 is ideal for the stimulation of T cells. The affinity of TR66 has been determined by use of surface-plasmon resonance (SPR) technology as well as by flow-cytometry, yielding equilibrium dissociation constants of $2.6 \times 10^{-7}$ M (Moore et al, Blood. 2011; 117: 4542-4551) and $1.0 \times 10^{-7}$ M (Amann et al, Cancer Res. 2008; 68: 143-151), respectively. In line with this, it has been recommended to use anti-CD3 antibodies with an affinity of less than $10^{-8}$ M (U.S. Pat. No. 7,112,324), and the T cell-stimulatory antibodies that have been published for human therapeutic use, bind with affinities to human CD3ε in the same range. Therefore, according to the theory of serial TCR triggering and in agreement with published results for anti-CD3ε antibodies, monoclonal antibodies with affinities significantly better than the ones published are not expected to be more potent stimulators of T cells, but in contrast are expected to be weaker activators.

Some of the published antibodies against CD3ε have been generated via immunization of animals with T cell preparations and subsequent isolation of monoclonal antibodies by the so-called hybridoma procedure. The weakness of this approach is that the unselective immune response against various antigens of foreign (human) T cells in the animal, on one hand, and the poor efficiency of the hybridoma procedure on the other hand, decrease the probability to identify monoclonal antibodies with T cell-stimulatory activity, also because these agonistic antibodies may represent a minority in the entirety of anti-CD3ε antibodies. Immunization with a linear peptide spanning the targeted epitope increases the selectivity of the immune response, may, however, result in antibodies that do not recognize the native full-length CD3ε or that may exert non-optimal TCR stimulation.

For the immunization of animals with other type-I transmembrane proteins it has been particularly useful to use the purified extracellular domain (ECD). However, purified ECD of CD3ε tends to aggregate, and aggregates may have an altered structure as compared to the native protein. Further this approach may preferentially lead to antibodies binding to the interface between CD3ε and CD3γ. In contrast, the complex of CD3ε and CD3γ produced as a single-chain protein, connected by a flexible peptide linker, can be purified in a monomeric fraction and in its native conformation (Kim et al, JMB. 2000; 302: 899-916). Immunization of animals with such a CD3ε/γ single-chain protein may however lead to antibodies concomitantly binding to CD3ε and CD3γ, which would result in antagonistic effects.

Several antibodies directed against human CD3ε have been developed in the past.

Monoclonal antibody SP34 is a murine antibody that cross-reacts with non-human primate CD3, and that is also capable of inducing cell proliferation on both human and non-human primate PBMCs (Pessano et al., The T3/T cell receptor complex: antigenic distinction between the two 20 kD T3 (T3δ and T3ε) subunits. EMBO J 4 (1985) 337-344).

WO 2007/042261 and WO 2008/119567, both assigned to Micromet (now Amgen Research (Munich)), disclose cross-reactive binders directed against the epitopes FSEXE (SEQ ID NO: 43) and QDGNE (SEQ ID NO: 44), respectively, in CD3ε. In opposition proceedings filed by several opponents against granted European patent EP 2 155 783 (based on the regional phase of WO 2008/119567), it is submitted that SP34 is binding to epitope QDGNE as well.

WO 2014/191113 disclose cross-reactive binders directed against a novel epitope at the N-terminus of CD3ε, wherein said epitope comprises amino acid residue N4 as residue that is critical for binding, and wherein said epitope further comprises amino acid residue E6 as residue that is involved in binding. It could be shown that these antibodies exhibit both high affinity and high potency. However, while it could additionally be shown in WO 2014/191113 that the antibodies disclosed in the application are cross-reactive with CD3 from non-human primates in vitro, cross-reactivity could not be shown to cynomolgous CD3 in a cellular context. Thus, these antibodies are of rather limited use with respect to the preclinical development of pharmaceutical products comprising an anti-CD3 antibody.

Thus, there remained still a large unmet need to develop novel CD3 binding molecules, in particular novel anti-CD3 antibodies, which exhibit the desired affinity and potency profile, but which additionally are cross-reactive with other species, in particular with non-human primates such as cynomolgus monkeys, both in vitro and in a cellular context.

SUMMARY OF THE INVENTION

The present invention addresses the above needs and provides novel antibodies that are specific for human CD3, in particular antibodies specific for the CD3ε domain. The solution provided by the present invention, i.e. CD3-binding molecules, in particular anti-CD3 antibodies obtained by peptide immunization of rabbits and screening of affinity matured memory B-cells, and in particular CD3-binding molecules, in particular anti-CD3 antibodies, in particular antibodies specific for the CD3ε domain, with the required cross-reactivity profile, has so far not been achieved or suggested by the prior art. Novel CD3 antibodies of the present invention exhibit the desired affinity and potency profile, are cross-reactive with other species, in particular with non-human primates such as cynomolgus monkeys, both in vitro and in a cellular context. In addition, the antibodies of the present invention have favorable biophysical properties, such as quality, stability or solubility, for example as defined by the percentage of antibody in monomer form and thermal unfolding determined by Differential Scanning Fluorimetry (DSF).

In a first aspect, the present invention relates to an antibody or functional fragment thereof, which is specific for human CD3, comprising:
a variable light chain, wherein the variable light chain comprises, from N-terminus to C-terminus, the regions LFW1-LCDR1-LFW2-LCDR2-LFW3-LCDR3-LFW4, wherein each LFW designates a light chain framework region, and each LCDR designates a light chain complementarity-determining region, and wherein said LCDRs together exhibit at least 90% sequence identity to the corresponding LCDRs taken from the VL sequence according to SEQ ID NO: 4;
and
a variable heavy chain, wherein the variable light chain comprises, from N-terminus to C-terminus, the regions HFW1-HCDR1-HFW2-HCDR2-HFW3-HCDR3-HFW4, wherein each HFW designates a heavy chain framework region, and each HCDR designates a heavy chain complementarity-determining region, and wherein said HCDRs together exhibit at least 90% sequence identity to the corresponding HCDRs taken from the VH sequence according to SEQ ID NO: 8.

In a second aspect, the present invention relates to a multispecific polypeptide comprising the antibody of the present invention or functional fragment thereof.

In a third aspect, the present invention relates to a pharmaceutical composition comprising the antibody or functional fragment thereof of the present invention, or the multispecific polypeptide of the present invention, and a pharmaceutically acceptable carrier and/or excipient.

In a fourth aspect, the present invention relates the antibody or functional fragment thereof of the present invention, or the multispecific polypeptide of the present invention for use as a medicament.

In a fifth aspect, the present invention relates to a nucleic acid sequence or a collection of nucleic acid sequences encoding the antibody or functional fragment thereof of the present invention.

In a sixth aspect, the present invention relates to a vector or a collection of vectors comprising the nucleic acid sequence or the collection of nucleic acid sequences of the present invention.

In a seventh aspect, the present invention relates to a host cell, particularly an expression host cell, comprising the nucleic acid sequence or the collection of nucleic acid sequences of the present invention, or the vector or collection of vectors of the present invention.

In an eighth aspect, the present invention relates to a method for producing the antibody or functional fragment thereof of the present invention, comprising the step of expressing the nucleic acid sequence or the collection of nucleic acid sequences of the present invention, or the vector or collection of vectors of the present invention, or the host cell, particularly the expression host cell, of the present invention.

In a ninth aspect, the present invention relates to a method of generating a multispecific construct, comprising the step of cloning, in one or more steps, one or more nucleic acid sequences encoding the antibody or functional fragment thereof according to the present invention, into a multispecific construct comprising a nucleic acid sequence encoding at least a second binding domain or a fragment thereof, and, optionally, a nucleic acid sequence encoding one or more additional binding domains or fragments thereof.

DETAILED DESCRIPTION OF THE INVENTION

Figure 1:
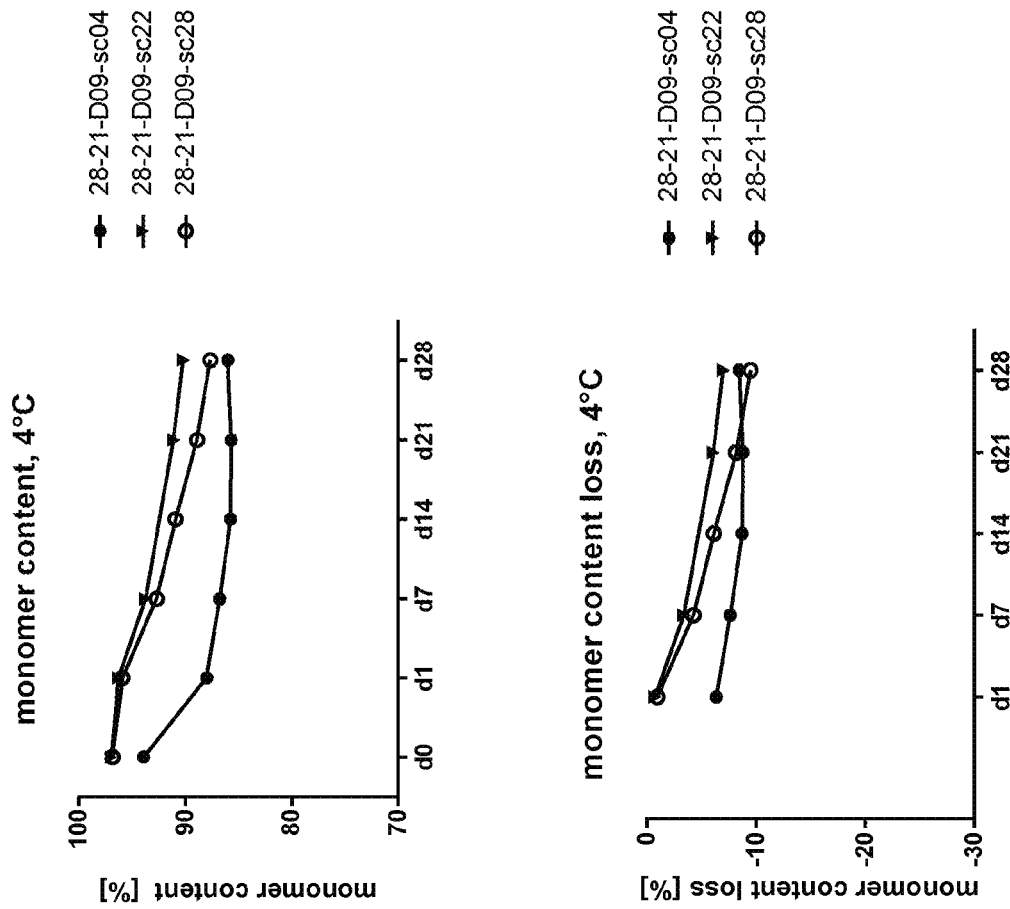
FIG. 1 shows monomer content of each sample determined by SE-HPLC initially (d0) and over a period of 28 days of storage at 4° C. and at a concentration of 10 mg/mL.

The present disclosure relates to novel antibodies that are specific for human CD3, in particular antibodies specific for the CD3ε domain.

Unless defined otherwise, all technical and scientific terms used herein have the same meaning as commonly understood by those of ordinary skill in the art to which this invention pertains.

The terms "comprising" and "including" are used herein in their open-ended and non-limiting sense unless otherwise noted. With respect to such latter embodiments, the term "comprising" thus includes the narrower term "consisting of".

The terms "a" and "an" and "the" and similar references in the context of describing the invention (especially in the context of the following claims) are to be construed to cover both the singular and the plural, unless otherwise indicated herein or clearly contradicted by context. For example, the term "a cell" includes a plurality of cells, including mixtures thereof. Where the plural form is used for compounds, salts, and the like, this is taken to mean also a single compound, salt, or the like.

In a first aspect, the present invention relates to an antibody or functional fragment thereof, which is specific for human CD3, comprising:

(a) a variable light chain, wherein the variable light chain comprises, from N-terminus to C-terminus, the regions LFW1-LCDR1-LFW2-LCDR2-LFW3-LCDR3-LFW4, wherein each LFW designates a light chain framework region, and each LCDR designates a light chain complementarity-determining region, and wherein said LCDRs together exhibit at least 60, 70, 80, 90, 91, 92, 93, 94, 95, 96, 97, 98 or 99 percent sequence identity, preferably at least 90% sequence identity, to the corresponding LCDRs taken from the VL sequence according to SEQ ID NO: 4; and (b) a variable heavy chain, wherein the variable light chain comprises, from N-terminus to C-terminus, the regions HFW1-HCDR1-HFW2-HCDR2-HFW3-HCDR3-HFW4, wherein each HFW designates a heavy chain framework region, and each HCDR designates a heavy chain complementarity-determining region, and wherein said HCDRs together exhibit at least 60, 70, 80, 90, 91, 92, 93, 94, 95, 96, 97, 98 or 99 percent sequence identity, preferably at least 90% sequence identity, to the corresponding HCDRs taken from the VH sequence according to SEQ ID NO: 8.

In the context of the present invention, the term "antibody" is used as a synonym for "immunoglobulin" (Ig), which is defined as a protein belonging to the class IgG, IgM, IgE, IgA, IgY or IgD (or any subclass thereof), and includes all conventionally known antibodies. A naturally occurring "antibody" is a glycoprotein comprising at least two heavy (H) chains and two light (L) chains inter-connected by disulfide bonds. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDRs), interspersed with regions that are more conserved, termed framework regions (FWs). Each VH and VL is composed of three CDRs and four FWs arranged from amino-terminus to carboxy-terminus in the following order: FW1-CDR1-FW2-CDR2-FW3-CDR3-FW4. The variable regions of the heavy and light chains contain a binding domain that interacts with an antigen.

The term "antibody fragment" refers to at least one portion of an intact antibody, or recombinant variants thereof, and the term "functional fragment" or "functional antibody fragment" or "antigen-binding fragment" refers to an antibody fragment comprising at least an antigen-binding domain, e.g., that part of the variable region of an intact antibody, that is sufficient to confer recognition and specific binding of the functional antibody fragment to a target, such as the antigenic determinant of an antigen. Examples of functional antibody fragments include, but are not limited to, Fab, Fab', F(ab')2, and Fv fragments, scFv antibody fragments, linear antibodies, single domain antibodies such as sdAb (either VL or VH), camelid VHH domains, and multi-specific molecules formed from antibody fragments such as a bivalent fragment comprising two or more, e.g., two, Fab fragments linked by a disulfide bridge at the hinge region, or two or more, e.g., two isolated CDR or other epitope binding fragments of an antibody linked. In one embodiment, the functional fragment of the invention is a scFv. An antibody fragment can also be incorporated into single domain antibodies, maxibodies, minibodies, nanobodies, intrabodies, diabodies, triabodies, tetrabodies, v-NAR and bis-scFv (see, e.g., Hollinger and Hudson, Nature Biotechnology 23:1126-1136, 2005). Antibody fragments can also be grafted into scaffolds based on polypeptides such as a fibronectin type III (Fn3) (see U.S. Pat. No. 6,703,199, which describes fibronectin polypeptide minibodies). An "antigen-binding region" or "antigen-binding domain" of an antibody typically is found in one or more hypervariable region(s) of an antibody, i.e., the CDR1, CDR2, and/or CDR3 regions; however, the variable "framework" regions can also play an important role in antigen binding, such as by providing a scaffold for the CDRs. The constant regions of the antibodies may mediate the binding of the immunoglobulin to host tissues or factors, including various cells of the immune system (e.g., effector cells) and the first component (Clq) of the classical complement system. The term "antibody", as used herein, includes for example, monoclonal antibodies, humanized antibodies, or chimeric antibodies. The antibodies can be of any isotype (e.g., IgG, IgE, IgM, IgD, IgA and IgY), class (e.g., IgG1, IgG2, IgG3, IgG4, IgA1 and IgA2) or subclass.

The "Complementarity Determining Regions" ("CDRs") are amino acid sequences with boundaries determined using any of a number of well-known schemes, including those described by Kabat et al. (1991), "Sequences of Proteins of Immunological Interest," 5th Ed. Public Health Service, National Institutes of Health, Bethesda, MD ("Kabat" numbering scheme), Al-Lazikani et al., (1997) JMB 273, 927-948 ("Chothia" numbering scheme) and ImMunoGenTics (IMGT) numbering (Lefranc, M.-P., The Immunologist, 7, 132-136 (1999); Lefranc, M.-P. et al., Dev. Comp. Immunol., 27, 55-77 (2003) ("IMGT" numbering scheme). For example, for classic formats, under Kabat, the CDR amino acid residues in the heavy chain variable domain (VH) are numbered 31-35 (HCDR1), 50-65 (HCDR2), and 95-102 (HCDR3); and the CDR amino acid residues in the light chain variable domain (VL) are numbered 24-34 (LCDR1), 50-56 (LCDR2), and 89-97 (LCDR3). Under Chothia the CDR amino acids in the VH are numbered 26-32 (HCDR1), 52-56 (HCDR2), and 95-102 (HCDR3); and the amino acid residues in VL are numbered 24-34 (LCDR1), 50-56 (LCDR2), and 89-97 (LCDR3). By combining the CDR definitions of both Kabat and Chothia, the CDRs consist of amino acid residues 26-35 (HCDR1), 50-65 (HCDR2), and 95-102 (HCDR3) in human VH and amino acid residues 24-34 (LCDR1), 50-56 (LCDR2), and 89-97 (LCDR3) in human VL. Under IMGT the CDR amino acid residues in the VH are numbered approximately 26-35 (HCDR1), 51-57 (HCDR2) and 93-102 (HCDR3), and the CDR amino acid residues in the VL are numbered approximately 27-32 (LCDR1), 50-52 (LCDR2), and 89-97 (LCDR3) (numbering according to "Kabat"). Under IMGT, the CDRs of an antibody can be determined using the program IMGT/DomainGap Align.

In the context of the present invention, the numbering system suggested by Honegger & Plückthun ("AHo numbering") is used (Honegger & Plückthun, J. Mol. Biol. 309 (2001) 657-670), unless specifically mentioned otherwise. Furthermore, the following residues are defined as CDRs: LCDR1 (also referred to as CDR-L1): L24-L42; LCDR2 (also referred to as CDR-L2): L58-L72; LCDR3 (also referred to as CDR-L3): L107-L138; HCDR1 (also referred to as CDR-H1): H27-H42; HCDR2 (also referred to as CDR-H2): H57-H76; HCDR3 (also referred to as CDR-H3): H108-H138. For the sake of clarity, the numbering system according to Honegger & Plückthun takes the length diversity into account that is found in naturally occurring antibodies, both in the different VH and VL subfamilies and, in particular, in the CDRs, and provides for gaps in the sequences. Thus, in a given antibody variable domain usually not all positions 1 to 149 will be occupied by an amino acid residue.

Preferably, the "antigen-binding region" comprises at least amino acid residues 4 to 138 of the variable light (VL) chain and 5 to 138 of the variable heavy (VH) chain (in each case numbering according to Honegger & Plückthun), more preferably amino acid residues 3 to 144 of VL and 4 to 144 of VH, and particularly preferred are the complete VL and VH chains (amino acid positions 1 to 149 of VL and 1 to 149 of VH). The framework regions and CDRs are indicated in the sequences shown in Table 1. A preferred class of immunoglobulins for use in the present invention is IgG. "Functional fragments" of the invention include the domain of a F(ab')$_2$ fragment, a Fab fragment, Fv and scFv. The F(ab')$_2$ or Fab may be engineered to minimize or completely remove the intermolecular disulphide interactions that occur between the CH1 and CL domains. The antibodies or functional fragments thereof of the present invention may be part of bi- or multifunctional polypeptides, as further described in Sections [0076] to [0111].

The following terms are used to describe the sequence relationships between two or more polynucleotide or amino acid sequences: "sequence identity" or "percentage of sequence identity". The term "sequence identity" as used herein is determined by calculating the maximum number of amino acid residues that are identical between two polypeptide sequences, wherein gaps and/or insertions may be factored in to allow for the largest degree of sequence overlap. For example, two 100mer polypeptides that are fully identical have a sequence identity of 100%. When they differ by a single mutation, or when one polypeptide contains a deletion of one amino acid, the sequence identity is 99% (99 out of 100 positions being identical). In other words, the "percentage of sequence identity" is calculated by comparing two optimally aligned sequences over the window of comparison, determining the number of positions at which the identical nucleic acid base (e.g., A, T, C, G, U or I) or amino acid residue occurs in both sequences to yield the number of matched positions, dividing the number of matched positions by the total number of positions in the comparison window (i.e., the window size), and multiplying the result by 100 to yield the percentage of sequence identity. The "sequence similarity" is the degree of resemblance between two sequences when they are compared. Where necessary or desired, optimal alignment of sequences for comparison can be conducted, for example, by the local homology algorithm of Smith and Waterman (Adv. Appl. Math. 2:482 (1981)), by the homology alignment algorithm of Needleman and Wunsch (J. Mol. Biol. 48:443-53 (1970)), by the search for similarity method of Pearson and Lipman (Proc. Natl. Acad. Sci. USA 85:2444-48 (1988)), by computerized implementations of these algorithms (e.g., GAP, BESTFIT, FASTA, and TFASTA in the Wisconsin Genetics Software Package, Genetics Computer Group, 575 Science Dr., Madison, Wis.), or by visual inspection. (See generally Ausubel et al. (eds.), Current Protocols in Molecular Biology, 4th ed., John Wiley and Sons, New York (1999)). Unless indicated otherwise herein, the degree of sequence similarity referred to herein is determined by utilization of Dayhoff PAM matrix (M. O. Dayhoff, R. Schwartz, B. C. Orcutt: A model of Evolutionary Change in Proteins, pages 345-352; in: Atlas of protein sequence and structure, National Biomedical Research Foundation, 1979).

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, gamma-carboxyglutamate, and O-phosphoserine. The terms "polypeptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer. Unless otherwise indicated, a particular polypeptide sequence also implicitly encompasses conservatively modified variants thereof.

The term "binding specificity" as used herein refers to the ability of an individual antibody combining site to react with one antigenic determinant and not with a different antigenic determinant. As used herein, a binding molecule is "specific to/for", "specifically recognizes", or "specifically binds to" a target, such as for example human CD3, when such binding molecule is able to discriminate between such target biomolecule and one or more reference molecule(s), since binding specificity is not an absolute, but a relative property. In its most general form (and when no defined reference is mentioned), "specific binding" is referring to the ability of the binding molecule to discriminate between the target biomolecule of interest and an unrelated biomolecule, as determined, for example, in accordance with a specificity assay methods known in the art. Such methods comprise, but are not limited to Western blots, ELISA, RIA, ECL, IRMA, SPR (Surface plasmon resonance) tests and peptide scans. For example, a standard ELISA assay can be carried out. The scoring may be carried out by standard colour development (e.g. secondary antibody with horseradish peroxide and tetramethyl benzidine with hydrogen peroxide). The reaction in certain wells is scored by the optical density, for example, at 450 nm. Typical background (=negative reaction) may be about 0.1 OD; typical positive reaction may be about 1 OD. This means the ratio between a positive and a negative score can be 10-fold or higher. In a further example, an SPR assay can be carried out, wherein at least 10-fold, preferably at least 100-fold difference between a background and signal indicates on specific binding. Typically, determination of binding specificity is performed by using not a single reference biomolecule, but a set of about three to five unrelated biomolecules, such as milk powder, transferrin or the like. The antibody of the invention or functional fragment thereof has a binding specificity for human CD3, preferably to human CD3ε.

In one embodiment, the antibody of the invention or functional fragment thereof has a binding specificity for human CD3 and to non-chimpanzee primate CD3. As evident to the person skilled in the art, it is not excluded from the scope of the invention that antibody of the invention or functional fragment thereof exhibiting cross-species specificity as defined herein may also bind, e.g., to chimpanzee CD3. On the other hand, it is apparent that antibody of the invention or functional fragment thereof which only bind to human CD3, but not to non-chimpanzee primate CD3, are excluded from the scope of the invention. This applies mutatis mutandis to binding domains which only bind to non-chimpanzee primate CD3, but not to human CD3, such as e.g. those of monoclonal antibody FN-18.

As used herein, a "non-chimpanzee primate" or "non-chimp primate" or grammatical variants thereof refers to any primate other than chimpanzee, i.e. other than an animal of belonging to the genus *Pan*, and including the species *Pan paniscus* and *Pan troglodytes*, also known as *Anthropopithecus troglodytes* or *Simia satyrus*. A "primate", "primate species", "primates" or grammatical variants thereof denote/s an order of eutherian mammals divided into the two suborders of prosimians and anthropoids and comprising man, apes, monkeys and lemurs. Specifically, "primates" as used herein comprises the suborder Strepsirrhini (non-tarsier prosimians), including the infraorder Lemuriformes (itself including the superfamilies Cheirogaleoidea and Lemuroidea), the infraorder Chiromyiformes (itself including the family Daubentoniidae) and the infraorder Lorisiformes (itself including the families Lorisidae and Galagidae). "Primates" as used herein also comprises the suborder Haplorrhini, including the infraorder Tarsiiformes (itself including the family Tarsiidae), the infraorder Simiiformes (itself including the Platyrrhini, or New World monkeys, and the Catarrhini, including the Cercopithecidea, or Old-World Monkeys). Most preferred is Macaca fascicularis (also known as Cynomolgus monkey and, therefore, in the Examples named "Cynomolgus"). Suitably, the antibody of the invention or functional fragment thereof has a binding specificity for human CD3 and for cynomolgus CD3.

Further, depending on the context, the term "specific binding" may also refer to the ability of a binding molecule to discriminate between the target biomolecule and one or more closely related biomolecule(s), which are used as reference points, such as, for example, CD3 molecules from a different species, e.g. murine CD3. Additionally, "specific binding" may relate to the ability of a binding molecule to discriminate between different parts of its target antigen, e.g. different domains, regions or epitopes of the target biomolecule, in particular the CD3ε domain, or between one or more key amino acid residues or stretches of amino acid residues of the target biomolecule.

In one embodiment, the antibody of the invention or functional fragment thereof has a binding specificity for human CD3ε.

The term "CD3" refers to a molecule expressed as part of the T cell receptor and has the meaning as typically ascribed to it in the prior art. In human, it encompasses individual or independently combined CD3 subunits CD3 epsilon, CD3 delta, and CD3 gamma. The non-chimpanzee primate CD3 antigens as referred to herein are, for example, Macaca fascicularis CD3 and Macaca mulatto CD3. In Macaca fascicularis, it encompasses CD3 epsilon FN-18 negative and CD3 epsilon FN-18 positive, CD3 gamma and CD3 delta. In Macaca mulatto, it encompasses CD3 epsilon, CD3 gamma and CD3 delta.

Preferably, said CD3 as used herein specifically relates to CD3ε. The term "human CD3ε" refers in particular to human CD3ε with the GenBank Accession No.NM_000733, UniProt ID number P07766 reproduced herein as SEQ ID NO: 19, or a variant thereof. The CD3ε "FN-18 negative" of Macaca fascicularis (i.e. CD3ε not recognized by monoclonal antibody FN-18 due to a polymorphism as set forth above) is indicated in GenBank Accession No. AB073994. The CD3ε "FN-18 positive" of Macaca fascicularis (i.e. CD3 epsilon recognized by monoclonal antibody FN-18) is indicated in GenBank Accession No. AB073993.

The human CD3 gamma is indicated in GenBank Accession No. NM 000073. The human CD3 delta is indicated in GenBank Accession No. NM 000732. The CD3 gamma of Macaca fascicularis is indicated in GenBank Accession No. AB073992. The CD3 delta of Macaca fascicularis is indicated in GenBank Accession No. AB073991.

Suitably, the antibodies of the invention or functional fragments thereof target human and cynomoglous (Macaca fascicularis) CD3ε.

Suitably, the antibody of the invention is a monoclonal antibody. The term "monoclonal antibody" or "monoclonal antibody composition" as used herein refers to antibodies that are substantially identical to amino acid sequence or are derived from the same genetic source. A monoclonal antibody composition displays a binding specificity and affinity for a particular epitope, or binding specificities and affinities for specific epitopes.

In the context of the present invention, the term "epitope" refers to that part of a given target biomolecule that is required for specific binding between the target biomolecule and a binding molecule. An epitope may be continuous, i.e. formed by adjacent structural elements present in the target biomolecule, or discontinuous, i.e. formed by structural elements that are at different positions in the primary sequence of the target biomolecule, such as in the amino acid sequence of a protein as target, but in close proximity in the three-dimensional structure, which the target biomolecule adopts, such as in the bodily fluid.

Antibodies of the invention include, but are not limited to, the chimeric, human and humanized antibodies.

The term "chimeric antibody" (or functional fragment thereof) is an antibody molecule (or functional fragment thereof) in which (a) the constant region, or a portion thereof, is altered, replaced or exchanged so that the antigen-binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity. For example, a mouse antibody can be modified by replacing its constant region with the constant region from a human immunoglobulin. Due to the replacement with a human constant region, the chimeric antibody can retain its specificity in recognizing the antigen, while having reduced antigenicity in human as compared to the original mouse antibody.

A "humanized" antibody (or functional fragment thereof), as used herein, is an antibody (or functional fragment thereof) that retains the reactivity of a non-human antibody while being less immunogenic in humans. This can be achieved, for instance, by retaining the non-human CDR regions and replacing the remaining parts of the antibody with their human counterparts (i.e., the constant region as well as the framework portions of the variable region). Additional framework region modifications may be made within the human framework sequences as well as within the CDR sequences derived from the germline of another mammalian species. The humanized antibodies of the invention may include amino acid residues not encoded by human sequences (e.g., mutations introduced by random or site-specific mutagenesis in vitro or by somatic mutation in vivo, or a conservative substitution to promote stability or manufacturing). See, e.g., Morrison et al., Proc. Natl. Acad. Sci. USA, 81:6851-6855, 1984; Morrison and Oi, Adv. Immunol., 44:65-92, 1988; Verhoeyen et al., Science, 239: 1534-1536, 1988; Padlan, Molec. Immun., 28:489-498, 1991; and Padlan, Molec. Immun., 31: 169-217, 1994. Other examples of antibody engineering technology include, but are not limited to Xoma technology disclosed in U.S. Pat. No. 5,766,886.

The term "recombinant humanized antibody", as used herein, includes all humanized antibodies of the invention that are prepared, expressed, created or isolated by recombinant means, such as antibodies isolated from an animal (e.g. a mouse); antibodies expressed using a recombinant expression vector transfected into a host cell, antibodies isolated from a recombinant, combinatorial human antibody library, or antibodies prepared, expressed, created or isolated by any other means that involves splicing of human immunoglobulin gene sequences to other DNA sequences. Such recombinant human antibodies have variable and constant regions (if present) derived from human germline immunoglobulin sequence. Such antibodies can, however, be subjected to in vitro mutagenesis (or, when an animal transgenic for human Ig sequences is used, in vivo somatic mutagenesis) and thus the amino acid sequences of the VH (antibody heavy chain variable region) and VL (antibody light chain variable region) of the recombinant antibodies are sequences that, while derived from and related to human germline VH and VL sequences, may not naturally exist within the human antibody germline.

Suitably, the antibody or functional fragment of the present invention is an artificial or an isolated antibody or functional fragment thereof. The term "artificial antibody", as used herein, means an antibody or functional fragment thereof, which, by virtue of its origin or manipulation: (i) is present in a host cell as the expression product of a portion of an expression vector, or (ii) is linked to a protein or other chemical moiety other than that to which it is linked in nature, or (iii) does not occur in nature. The term "isolated antibody", as used herein, refers to an antibody expressed in a host cell and purified away from associated proteins, as by gel chromatography. The term "isolated antibody" also refers to antibody that is substantially free of other antibodies having different antigenic specificities (e.g., an isolated antibody that specifically binds to human CD3 is substantially free of antibodies that specifically bind antigens other than human CD3). An isolated antibody that specifically binds human CD3 may, however, have cross-reactivity to other antigens, such as CD3 molecules from other species (e.g., non-human primate and/or rodent CD3). Moreover, an isolated antibody may be substantially free of other cellular material and/or chemicals.

In one embodiment, the present invention relates to an antibody or functional fragment thereof comprising (a) an LCDR1 as set forth in SEQ ID NO: 1; (b) an LCDR2 as set forth in SEQ ID NO: 2; (c) an LCDR3 as set forth in SEQ ID NO: 3; (d) an HCDR1 as set forth in SEQ ID NO: 5; (e)

an HCDR2 as set forth in SEQ ID NO: 6; and (f) an HCDR3 as set forth in SEQ ID NO: 7.

The antibody of the invention or functional fragment thereof comprises a variable heavy chain (VH) domain and a variable light chain (VL) domain. In the context of the present invention the terms "VH" (variable heavy chain), "Vκ" and "Vλ" refer to families of antibody heavy and light chain sequences that are grouped according to sequence identity and homology. Methods for the determination of sequence homologies, for example by using a homology search matrix such as BLOSUM (Henikoff, S. & Henikoff, J. G., Proc. Natl. Acad. Sci. USA 89 (1992) 10915-10919), and methods for the grouping of sequences according to homologies are well known to one of ordinary skill in the art. For VH, Vκ and Vλ different subfamilies can be identified, as shown, for example, in Knappik et al., J. Mol. Biol. 296 (2000) 57-86, which groups VH in VH1A, VH1B and VH2 to VH6, Vκ in Vκ1 to Vκ4 and Vλ in Vλ1 to Vλ3. In vivo, antibody Vκ chains, Vλ chains, and VH chains are the result of the random rearrangement of germline κ chain V and J segments, germline λ chain V and J segments, and heavy chain V, D and J segments, respectively. To which subfamily a given antibody variable chain belongs is determined by the corresponding V segment, and in particular by the framework regions FW1 to FW3. Thus, any VH sequence that is characterized in the present application by a particular set of framework regions HFW1 to HFW3 only, may be combined with any HFW4 sequence, for example an HFW4 sequence taken from one of the heavy chain germline J segments, or an HFW4 sequence taken from a rearranged VH sequence. In particular embodiments, the HFW4 sequence is WGQGTLVTVSS.

Suitably, the present invention provides an antibody or functional fragment thereof that specifically binds CD3 (e.g., human CD3 protein, in particular human CD3ε), wherein said antibody or functional fragment thereof comprises a VH4 or VH3 domain, preferably VH3 domain.

Suitably, the present invention provides an antibody or functional fragment thereof that specifically binds CD3 (e.g., human CD3 protein, in particular human CD3ε), wherein said antibody or functional fragment thereof comprises (i) Vκ frameworks FW1, FW2 and FW3, particularly Vκ1 or Vκ3 frameworks, preferably Vκ1 frameworks FW1 to FW3, and (ii) a framework FW4, which is selected from a Vκ FW4, particularly Vκ1 FW4, Vκ3 FW4, and a Vλ FW4. Suitable Vκ1 FW1 to FW3 exhibit at least 60, 70, 80, 90 percent sequence identity, preferably at least 90% sequence identity, to the corresponding framework regions taken from the Vκ1 sequence according to SEQ ID NO: 4. Suitable Vκ1 FW4 exhibits at least 60, 70, 80, 90 percent sequence identity, preferably at least 90% sequence identity, to the corresponding FW4 taken from the Vκ1 sequence according to SEQ ID NO: 4. Suitably, Vκ1 FW4 is the FW4 taken from the Vκ1 sequence according to SEQ ID NO: 4. Suitable Vλ FW4 is as set forth in SEQ ID NO: 17 or SEQ ID NO: 18. In one embodiment the present invention provides an antibody or a functional fragment thereof that specifically binds CD3 (e.g., human CD3 protein, in particular human CD3ε), wherein said antibody or functional fragment thereof comprises Vλ FW4 comprising the amino acid sequence having at least 60, 70, 80, 90 percent identity an amino acid sequence selected from any of SEQ ID NO: 17 to SEQ ID NO: 18, preferably to SEQ ID NO: 17.

In a particular embodiment, said variable light chain is a Vκ1 light chain, and/or said variable heavy chain is a VH3 chain. In another particular embodiment, said variable light chain is a chimeric light chain, comprising Vκ framework regions I to III and a Vλ framework region IV. In one embodiment, light chain is a chimeric light chain, comprising:

(i) the LCDR1, LCDR2, and LCDR3 sequences of SEQ ID NOs: 1, 2, and 3, respectively;
(ii) human Vκ framework regions FW1 to FW3, particularly human Vκ1 framework regions FW1 to FW3;
(iii) FW4, which is selected from (a) a human Vλ germ line sequence for FW4, particularly a Vλ germ line sequence selected from the SEQ ID NO: 17 and SEQ ID NO: 18, preferably SEQ ID NO: 17; and (b) a Vλ-based sequence, which has one or two mutations, particularly one mutation, compared to the closest human Vλ germ line sequence for FW4 comprising an amino acid sequence selected from the SEQ ID NO: 17 and SEQ ID NO: 18, preferably SEQ ID NO: 17.

In one embodiment, said variable light chain exhibits at least 60, 70, 80, 90, 91, 92, 93, 94, 95, 96, 97, 98 or 99% sequence identity to the amino acid sequence according to SEQ ID NO: 4, and/or wherein said variable heavy chain exhibits at least 60, 70, 80, 90, 91, 92, 93, 94, 95, 96, 97, 98 or 99% sequence identity to the amino acid sequence according to SEQ ID NO: 8. In a particular embodiment, said variable light chain exhibits at least 90% sequence identity to the amino acid sequence according to SEQ ID NO: 4, and/or wherein said variable heavy chain exhibits at least 90% sequence identity to the amino acid sequence according to SEQ ID NO: 8.

Suitably, the present invention relates to an antibody or functional fragment thereof, which is specific for human CD3, in particular human CD3ε, comprising a variable light chain, wherein said variable light chain exhibits at least 90% sequence identity to the amino acid sequence according to SEQ ID NO: 4 and wherein said variable light chain comprises an Arginine (R) or a Lysine (K) at the light chain amino acid position 54 (AHo numbering), preferably an Arginine (R). In a further embodiment, said variable light chain further comprises a Glutamine (Q) at the light chain amino acid position 50 (AHo numbering) and/or a Serine (S) at the light chain amino acid position 51 (AHo numbering), and optionally a Phenylalanine (F) at the light chain amino acid position 44 (AHo numbering) or a Glutamine (Q) at the light chain amino acid position 88 (AHo numbering) or a Histidine (H) at the light chain amino acid position 88 (AHo numbering). In a specific embodiment, the present invention relates to an antibody or functional fragment thereof, which is specific for human CD3, in particular human CD3ε, comprising a variable light chain, wherein said variable light chain exhibits at least 90% sequence identity to the amino acid sequence according to SEQ ID NO: 4 and wherein said variable light chain comprises an Arginine (R) at the light chain amino acid position 54 (AHo numbering), a Glutamine (Q) at the light chain amino acid position 50 (AHo numbering), a Serine (S) at the light chain amino acid position 51 (AHo numbering), and a Phenylalanine (F) at the light chain amino acid position 44 (AHo numbering).

In yet another embodiment, the present invention relates to an antibody or functional fragment thereof, which is specific for human CD3, in particular human CD3ε, comprising a variable light chain, wherein said variable light chain exhibits at least 90% sequence identity to the amino acid sequence according to SEQ ID NO: 4 and wherein said variable light chain comprises an Arginine (R) at the light chain amino acid position 54 (AHo numbering), and a Phenylalanine (F) at the light chain amino acid position 44 (AHo numbering).

Suitably, the present invention relates to an antibody or functional fragment thereof, which is specific for human CD3, in particular human CD3ε, comprising a variable heavy chain, wherein said variable heavy chain exhibits at least 90 sequence identity to the amino acid sequence according to SEQ ID NO: 8 and wherein said variable heavy chain comprises at least one, e.g. at least two, preferably at least three, of the following amino acids selected from the list consisting of an Alanine (A) at the heavy chain amino acid position 53 (AHo numbering), a Threonine (T) at the heavy chain amino acid position 103 (AHo numbering), and a Phenylalanine (F) at the heavy chain amino acid position 105 (AHo numbering). In one embodiment said variable heavy chain exhibits at least 90% sequence identity to the amino acid sequence according to SEQ ID NO: 8 and comprises an Alanine (A) at the heavy chain amino acid position 53 (AHo numbering), a Threonine (T) at the heavy chain amino acid position 103 (AHo numbering), and a Phenylalanine (F) at the heavy chain amino acid position 105 (AHo numbering).

In one embodiment, the present invention relates to the antibody of the invention or functional fragment thereof comprising a variable light chain comprising the amino acid sequence of SEQ ID NO: 4 or a conservatively modified variant thereof, and a variable heavy chain comprising the amino acid sequence of SEQ ID NO: 8 or a conservatively modified variant thereof.

The term "conservatively modified variant" or "conservative variants" applies to both amino acid and nucleic acid sequences. With respect to particular nucleic acid sequences, conservatively modified variants refer to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations", which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

For polypeptide sequences, "conservatively modified variants" or "conservative variants" include individual substitutions, deletions or additions to a polypeptide sequence which result in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention. The following eight groups contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)). In one embodiment, the term "conservative sequence modifications" are used to refer to amino acid modifications that do not significantly affect or alter the binding characteristics of the antibody containing the amino acid sequence.

In a preferred embodiment, the antibody of the invention or functional fragment thereof comprises a variable light chain comprising the amino acid sequence of SEQ ID NO: 4, and a variable heavy chain comprising the amino acid sequence of SEQ ID NO: 8.

In one embodiment of the present invention, the isolated antibody or functional fragment thereof is selected from: an IgG antibody, a Fab and an scFv fragment. Suitably, the antibody of the invention or functional fragment thereof is scFv antibody fragment. "Single-chain Fv" or "scFv" or "sFv" antibody fragments comprise the VH and VL domains of an antibody, wherein these domains are present in a single polypeptide chain. Generally, the Fv polypeptide further comprises a polypeptide linker between the VH and VL domains, which enables the sFv to form the desired structure for target binding (see, for example, Plückthun, The Pharmacology of Monoclonal Antibodies, vol. 113, Rosenburg and Moore eds., Springer-Verlag, New York, 1994, pp. 269-315).

Suitably, the antibody of the invention or functional fragment thereof is an scFv. In particular embodiments, said functional fragment is an scFv format comprising the linker according to SEQ ID NO: 15. Suitably, the antibody of the invention or functional fragment thereof is an scFv comprising at least one amino acid sequence selected from the list consisting of SEQ ID NOs: 4, 8, 29, 30, 32, 33, 35, 36, 37, 38, 39, 40, 41, and 42. Suitably, the antibody of the invention or functional fragment thereof is an scFv comprising the amino acid sequence selected from the list consisting of SEQ ID NOs: 29, 30, 32, 33, 35, 36, 37, 38, 39, 40, 41, and 42.

The term "affinity" as used herein refers to the strength of the sum of total noncovalent interactions between a single binding site or a molecule, e.g., an antibody or a functional fragment thereof, and its binding partner, e.g., an antigen. Unless indicated otherwise, as used herein, "binding affinity" refers to intrinsic binding affinity which reflects 1:1 interaction between members of a binding pair, e.g., interaction of a single antibody binding domain and its antigen. The affinity can generally be represented by the dissociation constant ($K_D$). Affinity can be measured by common methods known in the art, including those described herein.

In a suitable embodiment, the antibody of the invention or functional fragment thereof may have a $K_D$ to human CD3 and/or to cynomolgous CD3 of between 0.1 to 100 nM, 0.1 to 90 nM, 0.1 to 80 nM, 0.1 to 70 nM, 0.1 to 60 nM, 0.5 to 50 nM, 0.5 to 40 nM, 0.5 to 30 nM, 0.5 to 20 nM, 0.5 to 10 nM, 0.5 to 9 nM, 0.5 to 8 nM, 0.5 to 7 nM, 0.5 to 6 nM, 0.5 to 5 nM, particularly as measured by surface plasmon resonance. In a suitable embodiment, the antibody of the invention or functional fragment thereof may have a $K_D$ to human CD3 and/or to cynomolgous CD3 of less than approximately 100 nM, less than approximately 90 nM, less than approximately 80 nM, less than approximately 70 nM, less than approximately 60 nM, less than approximately 55 nM, less than approximately 40 nM, less than approximately 45 nM, less than approximately 40 nM, less than approximately 35 nM, less than approximately 30 nM, less than approximately 25 nM, less than approximately 20 nM, less than approximately 15 nM, less than approximately 10 nM, less than approximately 9 nM, less than approximately 8 nM, less than approximately 7 nM, less than approximately 6 nM, less than approximately 5 nM, less than approximately 4 nM, less than approximately 3 nM, less than 2 nM, less than 1 nM, particularly as measured by surface plasmon resonance. Suitably, the antibody of the invention or functional fragment thereof has a $K_D$ to human CD3 and/or to cynomolgous CD3 of less than 10 nM, preferably less than 6 nM, particularly as measured by surface plasmon resonance.

In a particular embodiment, the antibody of the invention or the functional fragment thereof, is characterized by one or more of the following parameters:
(i) a $K_D$ value for the binding to human CD3 of less than 40 nM, particularly less than 10 nM, more particularly less than 6 nM, particularly as measured by surface plasmon resonance, more particularly as determined by the method shown in Example 2.1;
(ii) a $K_D$ value for the binding to cynomolgous CD3 of less than 20 nM, particularly less than 10 nM, more particularly less than 5 nM, particularly as measured by surface plasmon resonance, more particularly as determined by the method shown in Example 2.1; and
(iii) an average midpoint of thermal unfolding temperature (Tm) exceeding at least 60° C., particularly at least 65° C., more particularly at least 68° C., when expressed in the scFv (single chain variable fragment format) antibody format, as determined by differential scanning fluorimetry (DSF) as described earlier (Egan, et al., MAbs, 9(1) (2017), 68-84; Niesen, et al., Nature Protocols, 2(9) (2007) 2212-2221) in particular when samples are diluted in five phosphate-citrate buffers at pH values ranging from 3.5 to 7.5 and containing 0.15-0.25 M NaCl, particularly 0.15 M NaCl. The midpoint of transition for the thermal unfolding of the scFv constructs is determined by Differential Scanning Fluorimetry using the fluorescence dye SYPRO® Orange (see Wong & Raleigh, Protein Science 25 (2016) 1834-1840). Samples in relevant excipient conditions are prepared at a final protein concentration of 50 μg ml$^{-1}$ by spiking in stock excipients that are prepared in relevant buffer. For a buffer scouting experiment samples are diluted in final scFv buffers with different pH values (pH 3.4, 4.4, 5.4, 6.4 and 7.2) containing a final concentration of 5× SYPRO® Orange in a total volume of 100 μl. Along with the unknown samples the scFv DSF reference is measured as internal control. Twenty-five microliters of prepared samples are added in triplicate to white-walled AB gene PCR plates. The assay is performed in a qPCR machine used as a thermal cycler, and the fluorescence emission is detected using the software's custom dye calibration routine. The PCR plate containing the test samples is subjected to a temperature ramp from 25° C. to 96° C. in increments of 1° C. with 30 s pauses after each temperature increment. The total assay time is about two hours. The Tm is calculated by the software GraphPad Prism using a mathematical second derivative method to calculate the inflection point of the curve. The reported Tm is an average of three measurements. In a particular embodiment, the determination of Tm is performed as described in Example 2.2, wherein a sample is diluted in phosphate-citrate buffer at a pH value of 6.4, which contains 0.25 M NaCl In one aspect, the present invention relates to a multispecific molecule, e.g., bispecific molecule, trispecific molecule, tetraspecific, pentaspecific, hexaspecific molecule, or a multivalent molecule, e.g., bivalent, trivalent, tetravalent, pentavalent, hexavalent molecule, comprising the antibody of the invention or functional fragment thereof. In a particular embodiment, the multispecific molecule is a multispecific polypeptide. In a particular embodiment, the multivalent molecule is a multivalent polypeptide.

The term "bispecific antibody" or "bispecific polypeptide", as used herein, refers to an antibody that binds to two different epitopes, in particular two different epitopes on two different targets. The term "trispecific antibody" or "trispecific polypeptide", as used herein, refers to an antibody that binds to three different epitopes, in particular three different epitopes on three different targets.

An antibody of the invention, or functional fragment thereof, can be derivatized or linked to another functional molecule, e.g., another peptide or protein (e.g., another antibody or ligand for a receptor) to generate a multispecific molecule (e.g., multispecific polypeptide) that binds to at least two binding sites and/or different target molecules. The antibody of the invention may in fact be derivatized or linked to more than one other functional molecule to generate multispecific molecules (e.g., multispecific polypeptides) that bind to more than two different binding sites and/or target molecules. To create a multispecific molecule of the invention, an antibody of the invention can be functionally linked (e.g., by chemical coupling, genetic fusion, noncovalent association or otherwise) to one or more other binding molecules, such as another antibody, antibody fragment, peptide or binding mimetic, such that a multispecific molecule results.

In one embodiment, the multispecific polypeptide of the present invention comprises: (a) the antibody of the invention or functional fragment thereof, and (b) at least one binding domain that binds to a different target than CD3.

The terms "binding domain", "antigen-binding fragment thereof", "antigen binding portion" or "functional fragment" of an antibody, and the like, as used herein, refer to one or more fragments of an intact antibody that retain the ability to specifically bind to a given antigen (e.g., CD3, IL23R, HER2, HSA). Antigen binding functions of an antibody can be performed by fragments of an intact antibody. In some embodiments, a binding domain of a multispecific antibody of the present invention is selected from the group consisting of a Fab fragment, a monovalent fragment consisting of the VL, VH, CL and CHI domains; a F(ab')$_2$ fragment, a bivalent fragment comprising two Fab fragments linked by a disulfide bridge at the hinge region; an Fd fragment consisting of the VH and CHI domains; an Fv fragment consisting of the VL and VH domains of a single arm of an antibody; a single domain antibody (dAb) fragment (Ward et al., 1989 Nature 341:544-546), which consists of a VH domain; an isolated complementarity determining region (CDR), dsFv, a scAb, STAB, a single domain antibody (sdAb or dAb), a single domain heavy chain antibody, and a single domain light chain antibody, a VHH, a VNAR, single domain antibodies based on the VNAR structure from shark, and binding domains based on alternative scaffolds including but limited to ankyrin-based domains, fynomers, avimers, anticalins, fibronectins, and binding sites being built into constant regions of antibodies (e.g. f-star technology). Suitably, a binding domain of the present invention is a single-chain Fv fragment (scFv) or single antibody variable domains. In a preferred embodiment, a binding domain of the present invention is a single-chain Fv fragment (scFv).

Suitably, the multispecific polypeptide of the present invention comprises: (a) the antibody of the invention or functional fragment thereof, and (b) at least one, preferably one, tumor associated antigen (TAA) binding domain.

In one embodiment, the multispecific polypeptide of the present invention comprises: (a) the antibody of the invention or functional fragment thereof, and (b) at least one, preferably one, IL23R-binding domain.

Interleukin (IL)-23 is a heterodimeric cytokine comprised of two protein subunits, designated p40 and p19 for their approximate molecular weights. The p40 protein is shared between IL-12 and IL-23, whereas the p19 protein subunit is unique to IL-23. IL-23 signals through a two-chain receptor complex consisting of the IL-12 receptor beta-1 (IL-12Rβ1) chain, which binds to p40, and a unique IL-23 receptor chain (IL23R), which confers IL-23-specific intracellular signaling. The term "IL23R" refers in particular to human IL23R with UniProt ID number Q5VWK5.

In some embodiments, the IL23R-binding domain is derived from a monoclonal antibody or antibody fragment.

A suitable IL23R-binding domain is specific for human IL23R and comprises: a variable light chain, wherein the variable light chain comprises, from N-terminus to C-terminus, the regions LFW1-LCDR1-LFW2-LCDR2-LFW3-LCDR3-LFW4, wherein each LFW designates a light chain framework region, and each LCDR designates a light chain complementarity-determining region, and wherein said LCDRs together exhibit at least 90% sequence identity to the corresponding LCDRs taken from the VL sequence according to SEQ ID NO: 11; and a variable heavy chain, wherein the variable light chain comprises, from N-terminus to C-terminus, the regions HFW1-HCDR1-HFW2-HCDR2-HFW3-HCDR3-HFW4, wherein each HFW designates a heavy chain framework region, and each HCDR designates a heavy chain complementarity-determining region, and wherein said HCDRs together exhibit at least 90% sequence identity to the corresponding HCDRs taken from the VH sequence according to SEQ ID NO: 12. Suitably, the IL23R-binding domain of the present invention comprises (i) an LCDR1, LCDR2, LCDR3 as set forth in the corresponding CDR regions taken from the VL sequence according to SEQ ID NO: 11, and (ii) an HCDR1, HCDR2, HCDR3 as set forth in the corresponding CDR regions taken from the VH sequence according to SEQ ID NO: 12.

In one embodiment, said variable light chain of the IL23R-binding domain exhibits at least 90% sequence identity to the amino acid sequence according to SEQ ID NO: 11, and/or said variable heavy chain of the IL23R-binding domain exhibits at least 90% sequence identity to the amino acid sequence according to SEQ ID NO: 12. In a specific embodiment, the IL23R-binding domain of the present invention comprises: (i) a variable light chain exhibiting at least 90% sequence identity to the amino acid sequence according to SEQ ID NO: 11, wherein said variable light chain comprises an LCDR1, LCDR2, LCDR3 as set forth in the corresponding CDR regions taken from the VL sequence according to SEQ ID NO: 11, and/or (ii) a variable heavy chain exhibiting at least 90% sequence identity to the amino acid sequence according to SEQ ID NO: 12, wherein said variable heavy chain comprises an HCDR1, HCDR2, HCDR3 as set forth in the corresponding CDR regions taken from the VH sequence according to SEQ ID NO: 12. In a specific embodiment, said variable light chain of the IL23R-binding domain comprises the amino acid sequence according to SEQ ID NO: 11 or a conservatively modified variant thereof, and/or said variable heavy chain of the IL23R-binding domain comprises the amino acid sequence according to SEQ ID NO: 12 or a conservatively modified variant thereof. In a more specific embodiment, said variable light chain of the IL23R-binding domain comprises the amino acid sequence according to SEQ ID NO: 11, and/or said variable heavy chain of the IL23R-binding domain comprises the amino acid sequence according to SEQ ID NO: 12.

In particular embodiments, said IL23R-binding domain is in an scFv format comprising the linker according to SEQ ID NO: 15.

In one embodiment, the multispecific polypeptide of the present invention comprises: (a) the antibody of the invention or functional fragment thereof, and (b) at least one IL23R-binding domain, and wherein said multispecific polypeptide comprises the amino acid sequence having at least 60, 70, 80, 90 percent identity to the amino acid sequence SEQ ID NO: 26, preferably wherein said multispecific polypeptide comprises the amino acid sequence according to SEQ ID NO: 26.

In one embodiment, the multispecific polypeptide of the present invention comprises: (a) the antibody of the invention or functional fragment thereof, and (b) at least one, preferably one, HER2-binding domain.

The term "HER2" refers in particular to human HER2 with UniProt ID number Q5VWK5.

In some embodiments, the HER2-binding domain is derived from a monoclonal antibody or antibody fragment.

A suitable HER2-binding domain is specific for human HER2 and comprises: a variable light chain, wherein the variable light chain comprises, from N-terminus to C-terminus, the regions LFW1-LCDR1-LFW2-LCDR2-LFW3-LCDR3-LFW4, wherein each LFW designates a light chain framework region, and each LCDR designates a light chain complementarity-determining region, and wherein said LCDRs together exhibit at least 90% sequence identity to the corresponding LCDRs taken from the VL sequence according to SEQ ID NO: 20; and a variable heavy chain, wherein the variable light chain comprises, from N-terminus to C-terminus, the regions HFW1-HCDR1-HFW2-HCDR2-HFW3-HCDR3-HFW4, wherein each HFW designates a heavy chain framework region, and each HCDR designates a heavy chain complementarity-determining region, and wherein said HCDRs together exhibit at least 90% sequence identity to the corresponding HCDRs taken from the VH sequence according to SEQ ID NO: 21. Suitably, the HER2-binding domain of the present invention comprises (i) an LCDR1, LCDR2, LCDR3 as set forth in the corresponding CDR regions taken from the VL sequence according to SEQ ID NO: 20, and (ii) an HCDR1, HCDR2, HCDR3 as set forth in the corresponding CDR regions taken from the VH sequence according to SEQ ID NO: 21.

In one embodiment, said variable light chain of the HER2-binding domain exhibits at least 90% sequence identity to the amino acid sequence according to SEQ ID NO: 20, and/or said variable heavy chain of the HER2-binding domain exhibits at least 90% sequence identity to the amino acid sequence according to SEQ ID NO: 21. In a specific embodiment, the HER2-binding domain of the present invention comprises: (i) a variable light chain exhibiting at least 90% sequence identity to the amino acid sequence according to SEQ ID NO: 20, wherein said variable light chain comprises an LCDR1, LCDR2, LCDR3 as set forth in the corresponding CDR regions taken from the VL sequence according to SEQ ID NO: 20, and/or (ii) a variable heavy chain exhibiting at least 90% sequence identity to the amino acid sequence according to SEQ ID NO: 21, wherein said variable heavy chain comprises an HCDR1, HCDR2, HCDR3 as set forth in the corresponding CDR regions taken from the VH sequence according to SEQ ID NO: 21. In a specific embodiment, said variable light chain of the HER2-binding domain comprises the amino acid sequence according to SEQ ID NO: 20 or a conservatively modified variant thereof, and/or said variable heavy chain of the HER2 binding domain comprises the amino acid sequence according to SEQ ID NO: 21 or a conservatively modified variant thereof. In a more specific embodiment, said variable light chain of the HER2-binding domain comprises the amino acid sequence according to SEQ ID NO: 20, and/or said variable heavy chain of the HER2 binding domain comprises the amino acid sequence according to SEQ ID NO: 21.

In particular embodiments, said HER2-binding domain is in an scFv format comprising the linker according to SEQ ID NO: 15.

In a specific embodiment, the HER2-binding domain of the present invention is trastuzumab or functional fragment thereof. In one embodiment, the multispecific polypeptide of the present invention comprises: (a) the antibody of the invention or functional fragment thereof, and (b) at least one HER2-binding domain, and wherein said multispecific polypeptide comprises the amino acid sequence having at least 60, 70, 80, 90 percent identity to the amino acid sequence SEQ ID NO: 27, preferably wherein said multispecific polypeptide comprises the amino acid sequence according to SEQ ID NO: 27.

In a further embodiment, the multispecific polypeptide of the present invention may comprise a further binding domain having a specificity to human serum albumin. In one embodiment, the multispecific polypeptide of the present invention comprises: (a) the antibody of the invention or functional fragment thereof, (b) at least one, preferably one, IL23R-binding domain, and (c) at least one, preferably one, HSA-binding domain. In one embodiment, the multispecific polypeptide of the present invention comprises: (a) the antibody of the invention or functional fragment thereof, (b) at least one, preferably one, HER2-binding domain, and (c) at least one, preferably one, HSA-binding domain.

The term "HSA" refers in particular to human serum albumin with UniProt ID number P02768, or a variant thereof. Human Serum Albumin (HSA) is 66.4 kDa abundant protein in human serum (50% of total protein) composing of 585 amino acids (Sugio, Protein Eng, Vol. 12, 1999, 439-446). Multifunctional HSA protein is associated with its structure that allowed to bind and transport a number of metabolizes such as fatty acids, metal ions, bilirubin and some drugs (Fanali, Molecular Aspects of Medicine, Vol. 33, 2012, 209-290). HSA concentration in serum is around 3.5-5 g/dL. Albumin-binding antibodies and fragments thereof may be used for example, for extending the in vivo serum half-life of drugs or proteins conjugated thereto.

In some embodiments, the HSA-binding domain is derived from a monoclonal antibody or antibody fragment.

Suitable HSA-binding domains for use in the multispecific polypeptide of the invention are binding domains provided in the present disclosure. The HSA-binding domains of the invention include, but are not limited to, the humanized monoclonal antibodies whose sequences are listed in Table 1.

A suitable HSA-binding domain is specific for human HSA and comprises: a variable light chain exhibiting at least 90% sequence identity to the amino acid sequence according to SEQ ID NO: 22, and/or a variable heavy chain exhibiting at least 90% sequence identity to the amino acid sequence according to SEQ ID NO: 23. In a specific embodiment, the HSA-binding domain of the present invention comprises: (i) a variable light chain exhibiting at least 90% sequence identity to the amino acid sequence according to SEQ ID NO: 22, wherein said variable light chain comprises an LCDR1, LCDR2, LCDR3 as set forth in the corresponding CDR regions taken from the VL sequence according to SEQ ID NO: 22, and/or (ii) a variable heavy chain exhibiting at least 90% sequence identity to the amino acid sequence according to SEQ ID NO: 23, wherein said variable heavy chain comprises an HCDR1, HCDR2, HCDR3 as set forth in the corresponding CDR regions taken from the VH sequence according to SEQ ID NO: 23. In a more specific embodiment, said variable light chain of the HSA-binding domain comprises the amino acid sequence according to SEQ ID NO: 22, and/or said variable heavy chain of the HSA-binding domain comprises the amino acid sequence according to SEQ ID NO: 23. Another suitable HSA-binding domain specific for human HSA comprises: a variable light chain exhibiting at least 90% sequence identity to the amino acid sequence according to SEQ ID NO: 24, and/or a variable heavy chain exhibiting at least 90% sequence identity to the amino acid sequence according to SEQ ID NO: 25. In a specific embodiment, the HSA-binding domain of the present invention comprises: (i) a variable light chain exhibiting at least 90% sequence identity to the amino acid sequence according to SEQ ID NO: 24, wherein said variable light chain comprises an LCDR1, LCDR2, LCDR3 as set forth in the corresponding CDR regions taken from the VL sequence according to SEQ ID NO: 24, and/or (ii) a variable heavy chain exhibiting at least 90% sequence identity to the amino acid sequence according to SEQ ID NO: 25, wherein said variable heavy chain comprises an HCDR1, HCDR2, HCDR3 as set forth in the corresponding CDR regions taken from the VH sequence according to SEQ ID NO: 25. In a specific embodiment, said variable light chain of the HSA-binding domain comprises the amino acid sequence according to SEQ ID NO: 24 or a conservatively modified variant thereof, and/or said variable heavy chain of the HSA-binding domain comprises the amino acid sequence according to SEQ ID NO: 25 or a conservatively modified variant thereof. In a more specific embodiment, said variable light chain of the HSA-binding domain comprises the amino acid sequence according to SEQ ID NO: 24, and/or said variable heavy chain of the HSA-binding domain comprises the amino acid sequence according to SEQ ID NO: 25.

In particular embodiments, said HSA-binding domain is in an scFv format comprising the linker according to SEQ ID NO: 15.

Suitably, the multispecific polypeptide of the present invention is in an antibody format selected from any suitable multispecific, e.g. bispecific, format known in the art, including, by way of non-limiting example, formats based on a single-chain diabody (scDb), a tandem scDb (Tandab), a linear dimeric scDb (LD-scDb), a circular dimeric scDb (CD-scDb), a bispecific T-cell engager (BiTE; tandem di-scFv), a tandem tri-scFv, a tribody (Fab-(scFv)$_2$) or bibody (Fab-(scFv)1), Fab, Fab-Fv$_2$, Morrison (IgG CH3-scFv fusion (Morrison L) or IgG CL-scFv fusion (Morrison H)), triabody, scDb-scFv, bispecific Fab$_2$, di-miniantibody, tetrabody, scFv-Fc-scFv fusion, scFv-HSA-scFv fusion, di-diabody, DVD-Ig, COVD, IgG-scFab, scFab-dsscFv, Fv$_2$-Fc, IgG-scFv fusions, such as bsAb (scFv linked to C-terminus of light chain), Bs1Ab (scFv linked to N-terminus of light chain), Bs2Ab (scFv linked to N-terminus of heavy chain), Bs3Ab (scFv linked to C-terminus of heavy chain), Ts1Ab (scFv linked to N-terminus of both heavy chain and light chain), Ts2Ab (dsscFv linked to C-terminus of heavy chain), and Knob-into-Hole antibodies (KiHs) (bispecific IgGs prepared by the KiH technology), a MATCH (described in WO2016/0202457; Egan T., et al., mAbs 9 (2017) 68-84)

and DuoBodies (bispecific IgGs prepared by the Duobody technology) (MAbs. 2017 February/March; 9(2):182-212. doi: 10.1080/19420862.2016.1268307). Particularly suitable for use herein is a single-chain diabody (scDb), in particular a bispecific monomeric scDb, or scDb-scFv, in particular trispecific monomeric scDb-scFv.

The term "diabodies" refers to antibody fragments with two antigen-binding sites, which fragments comprise a VH connected to VL in the same polypeptide chain (VH-VL). By using a linker that is too short to allow pairing between the two domains on the same chain, the domains are forced to pair with the complementary domains of another chain to create two antigen-binding sites. Diabodies may be bivalent or bispecific. Diabodies are described more fully in, for example, EP 404097, WO 1993/01161, Hudson et al., Nat. Med. 9:129-134 (2003), and Hollinger et al., Proc. Natl. Acad. Sci. USA 90: 6444-6448 (1993). Triabodies and tetrabodies are also described in Hudson et al., Nat. Med. 9:129-134 (2003).

The bispecific scDb, in particular the bispecific monomeric scDb, particularly comprises two variable heavy chain domains (VH) or fragments thereof and two variable light chain domains (VL) or fragments thereof connected by linkers L1, L2 and L3 in the order VHA-L1-VLB-L2-VHB-L3-VLA, VHA-L1-VHB-L2-VLB-L3-VLA, VLA-L1-VLB-L2-VHB-L3-VHA, VLA-L1-VHB-L2-VLB-L3-VHA, VHB-L1-VLA-L2-VHA-L3-VLB, VHB-L1-VHA-L2-VLA-L3-VLB, VLB-L1-VLA-L2-VHA-L3-VHB or VLB-L1-VHA-L2-VLA-L3-VHB, wherein the VLA and VHA domains jointly form the antigen binding site for the first antigen, and VLB and VHB jointly form the antigen binding site for the second antigen.

The linker L1 particularly is a peptide of 2-10 amino acids, more particularly 3-7 amino acids, and most particularly 5 amino acids, and linker L3 particularly is a peptide of 1-10 amino acids, more particularly 2-7 amino acids, and most particularly 5 amino acids. In particular embodiments, L1 and L3 are both GGGGS (SEQ ID NO: 16). The middle linker L2 particularly is a peptide of 10-40 amino acids, more particularly 15-30 amino acids, and most particularly 20-25 amino acids. In particular embodiments, L2 is (GGGGS)$_4$ (SEQ ID NO: 15).

In one embodiment of the present invention, the multispecific polypeptide comprising the antibody of the invention or functional fragment thereof is a multispecific and/or multivalent antibody in a MATCH format described in WO 2016/0202457; Egan T., et al., mAbs 9 (2017) 68-84.

The bispecific, bivalent, multispecific and/or multivalent constructs of the present invention can be produced using any convenient antibody manufacturing method known in the art (see, e.g., Fischer, N. & Leger, 0., Pathobiology 74 (2007) 3-14 with regard to the production of bispecific constructs; Hornig, N. & Färber-Schwarz, A., Methods Mol. Biol. 907 (2012)713-727, and WO 99/57150 with regard to bispecific diabodies and tandem scFvs). Specific examples of suitable methods for the preparation of the bispecific construct of the present invention further include, inter alia, the Genmab (see Labrijn et al., Proc. Natl. Acad. Sci. USA 110 (2013) 5145-5150) and Merus (see de Kruif et al., Biotechnol. Bioeng. 106 (2010) 741-750) technologies. Methods for production of bispecific antibodies comprising a functional antibody Fc part are also known in the art (see, e.g., Zhu et al., Cancer Lett. 86 (1994) 127-134); and Suresh et al., Methods Enzymol. 121 (1986) 210-228).

These methods typically involve the generation of monoclonal antibodies, for example by means of fusing myeloma cells with the spleen cells from a mouse that has been immunized with the desired antigen using the hybridoma technology (see, e.g., Yokoyama et al., Curr. Protoc. Immunol. Chapter 2, Unit 2.5, 2006) or by means of recombinant antibody engineering (repertoire cloning or phage display/ yeast display) (see, e.g., Chames & Baty, FEMS Microbiol. Letters 189 (2000) 1-8), and the combination of the antigen-binding domains or fragments or parts thereof of two different monoclonal antibodies to give a bispecific construct using known molecular cloning techniques.

In particular embodiments, the multispecific polypeptide further comprises one or more polypeptide linkers.

In particular embodiments, said multispecific polypeptide is a monomeric polypeptide, particularly a monomeric polypeptide wherein the antibody or functional fragment thereof according to the present invention is an scFv antibody fragment linked via a linker to a second binding domain, particularly wherein said second binding domain is a second scFv antibody fragment.

In particular embodiments, said multispecific polypeptide is a dimeric polypeptide, particularly a dimeric polypeptide, wherein the association of the two polypeptides is caused by the association of complementary VL and VH domains of antibody fragments comprised in said multispecific polypeptide. In particular such embodiments, the multispecific polypeptide is a multispecific antibody construct in accordance with the teaching of WO 2016/202457. In particular other embodiments, the multispecific polypeptide is a single-chain diabody construct (scDb). In particular other embodiments, the multispecific polypeptide is a Fab-(scFv)$_n$ construct (n being an integer selected from 1, 2, 3, or 4) that employs a heterodimeric assembly of a Fab fragment consisting of VL-CL and VH-CH1 with either constant domain forming a scaffold, to which one or more scFv fragments are attached via flexible linkers.

In a third aspect, the present invention relates to a pharmaceutical composition comprising the antibody or functional fragment thereof of the present invention or the multispecific polypeptide of the present invention, and a pharmaceutically acceptable carrier and/or excipient.

The phrase "pharmaceutically acceptable" refers to those compounds, materials, compositions, and/or dosage forms which are, within the scope of sound medical judgment, suitable for use in contact with the tissues of human beings or animals without excessive toxicity, irritation, allergic response, or other problem or complication, commensurate with a reasonable benefit/risk ratio.

Pharmaceutical compositions in accordance with the present disclosure may further routinely contain pharmaceutically acceptable concentrations of salt, buffering agents, preservatives, supplementary immune potentiating agents such as adjuvants and cytokines and optionally other therapeutic agents. The composition may also include antioxidants and/or preservatives. As antioxidants may be mentioned thiol derivatives (e.g. thioglycerol, cysteine, acetylcysteine, cystine, dithioerythritol, dithiothreitol, glutathione), tocopherols, butylated hydroxyanisole, butylated hydroxytoluene, sulfurous acid salts (e.g. sodium sulfate, sodium bisulfite, acetone sodium bisulfite, sodium metabisulfite, sodium sulfite, sodium formaldehyde sulfoxylate, sodium thiosulfate) and nordihydroguaiaretic acid. Suitable preservatives may for instance be phenol, chlorobutanol, benzylalcohol, methyl paraben, propyl paraben, benzalkonium chloride and cetylpyridinium chloride.

In particular embodiments provided herein, said antibodies or functional fragments thereof can be isolated, prepared, expressed, or created by recombinant means, such as antibodies expressed using a recombinant expression vector transfected into a host cell, antibodies isolated from a recombinant, combinatorial antibody library, or antibodies prepared, expressed, created or isolated by any other means that involves creation, e.g., via synthesis, genetic engineering of DNA sequences that encode human immunoglobulin sequences, or splicing of sequences that encode human immunoglobulins, e.g., human immunoglobulin gene sequences, to other such sequences.

Thus, in a fourth aspect, the present invention relates to a nucleic acid sequence or a collection of nucleic acid sequences encoding the antibody or functional fragment thereof of the present invention.

The term "nucleic acid" is used herein interchangeably with the term "polynucleotide" and refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphorates, 2-O-methyl ribonucleotides, peptide-nucleic acids (PNAs). Unless otherwise indicated, a particular nucleic acid sequence also implicitly encompasses conservatively modified variants thereof (e.g., degenerate codon substitutions) and complementary sequences, as well as the sequence explicitly indicated. Specifically, as detailed below, degenerate codon substitutions may be achieved by generating sequences in which the third position of one or more selected (or all) codons is substituted with mixed-base and/or deoxyinosine residues (Batzer et al., Nucleic Acid Res. 19:5081, 1991; Ohtsuka et al., J. Biol. Chem. 260:2605-2608, 1985; and Rossolini et al., Mol. Cell. Probes 8:91-98, 1994).

In a fifth aspect, the present invention relates to a vector or a collection of vectors comprising the nucleic acid sequence or a collection of nucleic acid sequences of the present invention. The term "vector" or "expression vector" means a polynucleotide, most commonly a DNA plasmid, comprising nucleotide sequences encoding the antibodies of the invention or a fragment thereof for recombinant expression in host cells, preferably in mammalian cells. A vector may, or may not, be able to replicate in a cell. Once a polynucleotide encoding variable heavy and/or variable light chain of an antibody, or fragment thereof described herein has been obtained, the vector for the production of the antibody molecule can be produced by recombinant DNA technology using techniques well-known in the art. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination.

An expression vector can be transferred to a host cell by conventional techniques and the resulting cells can then be cultured by conventional techniques to produce an antibody described herein or a fragment thereof. Thus, the present invention relates to a host cell, particularly an expression host cell, comprising the nucleic acid sequence or the collection of nucleic acid sequences of the present invention, or the vector or collection of vectors of the present invention. In certain embodiments, a host cell contains a vector comprising a polynucleotide encoding both the variable heavy chain and variable light chain of the antibody of the invention, or a fragment thereof. In specific embodiments, a host cell contains two different vectors, a first vector comprising a polynucleotide encoding a variable heavy chain of said antibody, or a fragment thereof, and a second vector comprising a polynucleotide encoding a variable light chain of said antibody, or a fragment thereof. In other embodiments, a first host cell comprises a first vector comprising a polynucleotide encoding a variable heavy chain of said antibody, or a fragment thereof, and a second host cell comprises a second vector comprising a polynucleotide encoding a variable light chain of said antibody, or a functional fragment thereof.

Methods for the humanization of rabbit antibodies or rodent antibodies are well known to anyone of ordinary skill in the art (see, for example, Borras, J Biol Chem. 2010 Mar. 19; 285(12):9054-66; Rader et al, The FASEB Journal, express article 10.1096/fj.02-0281fje, published online Oct. 18, 2002; Yu et al (2010) A Humanized Anti-VEGF Rabbit Monoclonal Antibody Inhibits Angiogenesis and Blocks Tumor Growth in Xenograft Models. PLoS ONE 5(2): e9072. doi:10.1371/journal.pone.0009072). The immunization of the rabbits or rodents may be performed with the antigen of interest as such, such as a protein, or, in the case of peptide or protein antigens, by DNA immunization of a rabbit with a nucleic acid, e.g. a plasmid, encoding the peptides or proteins of interest.

In a sixth aspect, the present invention relates to a host cell, particularly an expression host cell, comprising the nucleic acid sequence or the collection of nucleic acid sequences of the present invention, or the vector or collection of vectors of the present invention.

The term "host cell" refers to a cell into which an expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

In a seventh aspect, the present invention relates to a method for producing the antibody or functional fragment thereof of the present invention, comprising the step of expressing the nucleic acid sequence or the collection of nucleic acid sequences of the present invention, or the vector or collection of vectors of the present invention, or the host cell, particularly the expression host cell, of the present invention.

In an eighth aspect, the present invention relates to a method of generating a multispecific construct, comprising the step of cloning, in one or more steps, one or more nucleic acid sequences encoding the antibody or functional fragment thereof according to the present invention, into a multispecific construct comprising a nucleic acid sequence encoding at least a second binding domain or a fragment thereof, and, optionally, a nucleic acid sequence encoding one or more additional binding domains or fragments thereof.

In particular embodiments of the eighth aspect, the second binding domain is a second antibody or functional fragment thereof.

In particular embodiments, at least one of said optional, additional binding domains is present, particularly wherein said additional binding domain is a third antibody or functional fragment thereof.

In another aspect, the present invention relates to the antibody of the invention or functional fragment thereof, or the multispecific polypeptide comprising said antibody or functional fragment thereof, or the composition of the invention for use as a medicament.

In another aspect, the present invention relates to the antibody of the present invention or functional fragment thereof, or the multispecific polypeptide comprising said antibody or functional fragment thereof, or the composition of the invention for use in a manufacture of a medicament.

In one aspect, the present invention relates to the antibody of the present invention or functional fragment thereof, or the multispecific polypeptide comprising said antibody or functional fragment thereof, or the composition of the invention for use in treating a cancer, an inflammatory and/or autoimmune disease in a subject in need thereof.

In another aspect, the present invention relates to use of the antibody of the present invention or functional fragment thereof, or the multispecific polypeptide comprising said antibody or functional fragment thereof, or the composition of the invention to treat a cancer, an inflammatory and/or autoimmune disease in a subject in need thereof.

In a further aspect, the present invention relates to use of the antibody of the present invention or functional fragment thereof, or the multispecific polypeptide comprising said antibody or functional fragment thereof, or the composition of the invention in the manufacture of a medicament for treatment of a cancer, an inflammatory and/or autoimmune disease, in a subject in need thereof.

In one aspect, the present invention provides a method of treating a cancer, an inflammatory and/or autoimmune disease in a subject in need thereof comprising administering to the subject a therapeutically effective amount of the antibody of the present invention or functional fragment thereof, or the multispecific polypeptide comprising said antibody or functional fragment thereof, or the composition of the invention.

The term "subject" includes human and non-human animals. Non-human animals include all vertebrates, e.g., mammals and non-mammals, such as non-human primates, sheep, dog, cow, chickens, amphibians, and reptiles. Except when noted, the terms "patient" or "subject" are used herein interchangeably.

The terms "treatment", "treating", "treat", "treated", and the like, as used herein, refer to obtaining a desired pharmacologic and/or physiologic effect. The effect may be therapeutic in terms of a partial or complete cure for a disease and/or adverse effect attributable to the disease or delaying the disease progression. "Treatment", as used herein, covers any treatment of a disease in a mammal, e.g., in a human, and includes: (a) inhibiting the disease, i.e., arresting its development; and (c) relieving the disease, i.e., causing regression of the disease.

The term "therapeutically effective amount" or "efficacious amount" refers to the amount of an agent that, when administered to a mammal or other subject for treating a disease, is sufficient to effect such treatment for the disease. The "therapeutically effective amount" will vary depending on the agent, the disease and its severity and the age, weight, etc., of the subject to be treated.

The inflammatory and/or autoimmune disease may be rheumatoid arthritis, ankylosing spondylitis, psoriasis, psoriatic arthritis, ulcerative colitis, Crohn's disease, systemic lupus erythematosus, juvenile diabetes, autoimmune uveitis, and multiple sclerosis, Parkinson's disease, Alzheimer's disease, and ischemia-reperfusion injury.

The term "cancer" refers to a disease characterized by the rapid and uncontrolled growth of aberrant cells. Cancer cells can spread locally or through the bloodstream and lymphatic system to other parts of the body. The terms "tumor" and "cancer" are used interchangeably herein, e.g., both terms encompass solid and liquid, e.g., diffuse or circulating, tumors. As used herein, the term "cancer" or "tumor" includes premalignant, as well as malignant cancers and tumors.

The cancer to be treated includes, but is not limited to, colorectal cancer, lung cancer, breast cancer, nasopharyngeal cancer, oral cancer, esophageal cancer, pancreatic cancer, B-cell lymphomas, and T-cell lymphomas, including adult T-cell lymphoma leukemia (ATLL), acute myeloid lymphoma (AML), diffuse large B-cell lymphoma (DLBCL), follicular lymphoma (FL), pediatric acute lymphoblastic lymphoma (B-ALL), angioimmunoblastic T-cell lymphoma (AITL), anaplastic large-cell lymphoma (ALCL), T-/natural killer-cell lymphomas, and peripheral T-cell lymphoma (PTCL). In particular embodiments the cancer is selected from colorectal cancer, lung cancer, breast cancer, nasopharyngeal cancer, oral cancer, esophageal cancer, B-cell lymphomas, and T-cell lymphomas such as adult T-cell lymphoma leukemia (ATLL), angioimmunoblastic T-cell lymphoma (AITL), anaplastic large-cell lymphoma (ALCL), T-/natural killer-cell lymphomas, and peripheral T-cell lymphoma (PTCL).

EXAMPLES

The following examples illustrate the invention without limiting its scope.

Example 1: Selection and Humanization

For the Lead Candidate generation of the CD3ε binding domain six rabbit monoclonal antibody clones were selected.

The humanization of the selected clone comprised the transfer of the rabbit CDRs onto a scFv acceptor framework of the Vκ1/VH3 type as described in WO 2014/206561. In this process the amino acid sequences of the six CDR regions were identified on the donor sequence (rabbit mAb) and grafted into the acceptor scaffold sequence. For the selection the scFvs were constructed in a VL-Linker-VH arrangement. An example would be the combination of SEQ ID NOs: 4, 15 and 8 from N-terminus to C-terminus of the protein chain.

Additional amino acids from the rabbit donor in certain framework positions, which have been described to potentially influence CDR positioning and thus antigen binding (Borras et al., 2010; J. Biol. Chem., 285:9054-9066) were included in the final constructs. Table 2 shows the changes made for clone 28-21-D09 (numbering according to AHo). A comparison of the characterization data for these constructs revealed a significant advantage over the CDR grafting alone.

Once the in silico construct design described in the previous section was completed the corresponding genes were synthesized and bacterial expression vectors were constructed. The sequence of the expression constructs was confirmed on the level of the DNA and the constructs were manufactured according to generic expression and purification protocols.

The heterologous expression of the proteins was performed in E. coli as insoluble inclusion bodies. The expression culture was inoculated with an exponentially growing starting culture. The cultivation was performed in shake flasks in an orbital shaker using commercially available rich media. The cells were grown to a defined $OD_{600}$ of 2 and induced by overnight expression with 1 mM Isopropyl β-D-1-thiogalactopyranoside (IPTG). At the end of fermentation the cells were harvested by centrifugation and homogenized by sonication. At this point the expression level of the different constructs was determined by SDS-PAGE analysis of the cell lysate. The inclusion bodies were isolated from the homogenized cell pellet by a centrifugation protocol that included several washing steps to remove cell debris and other host cell impurities. The purified inclusion bodies were solubilized in a denaturing buffer (100 mM Tris/HCl pH 8.0, 6 M Gdn-HCl, 2 mM EDTA) and the scFvs were refolded by a scalable refolding protocol that generated milligram amounts of natively folded, monomeric scFv. A standardized protocol was employed to purify the scFvs, which included the following steps. The product after refolding was captured by an affinity chromatography employing Capto L agarose (GE Healthcare) to yield the purified scFvs. Lead candidates that met the affinity and potency criteria in initial testing were further purified by a polishing size-exclusion chromatography using a HiLoad Superdex75 column (GE Healthcare). Subsequent to the purification protocol the proteins were formulated in a buffered saline solution and characterized.

Example 2: Characterization of Humanized scFvs 2.1 Affinity to Human and Cynomolgus CD3ε

Affinity of the humanized scFvs to human and cynomolgus CD3ε was determined by SPR measurements using a T200 device (Biacore, General Electric). CD3ε was directly coupled to a CM5 sensor chip (Biacore, General Electric) using amine coupling chemistry. After performing a regeneration scouting and surface performance test to find best assay conditions, a scFv dose response was measured and obtained binding curves were double-referenced (empty reference channel and zero analyte injection) and fitted using the 1:1 Langmuir model to retrieve kinetic parameters. The assay was run in a 1 X PBS-Tween buffer at pH 7.4.

The SPR experiment shows the effect of adding structural residues from the rabbit donor IgG onto the humanized sequence (see Table 3). The construct 28-21-D09-sc03, which contains only the rabbit CDRs, exhibits no detectable binding to the target. All clones containing an arginine or lysine on position 54 of the VL do exhibit some binding to the target. Based on the SPR data the domains from construct 28-21-D09-sc04 were chosen for further in-vitro characterization in the scDb format.

2.2 Thermal Unfolding

The midpoint of transition for the thermal unfolding of the tested scFv constructs was determined by Differential Scanning Fluorimetry (DSF), essentially as described by Niesen (Niesen et al., Nat Protoc. 2 (2007) 2212-21). The DSF assay is performed in a qPCR machine (e.g. MX3005p, Agilent Technologies). The samples were diluted in buffer (citrate-phosphate pH 6.4, 0.25 M NaCl) containing a final concentration of 5× SYPRO orange in a total volume of 25 μL. In a buffer scouting experiment the pH dependence of the unfolding temperature was determined and comparable pH characteristics were observed for all constructs. Samples were measured in triplicates and a temperature ramp from 25-96° C. was programmed. The fluorescence signal was acquired and the raw data were analyzed with the GraphPad Prism (GraphPad Software Inc.).

The thermal unfolding of all functional humanized scFv constructs was analyzed by DSF as described above. While all constructs showed a midpoint of unfolding above 60° C. (see Table 4), there appears to be no correlation of high conformational stability and high affinity (compare to Table 3).

2.3. Storage Stability

Initial monomer content of each sample was determined by size exclusion high-performance liquid chromatography (SE-HPLC) (d0). Samples were passed through a Shodex™ (Showa Denko) KW402.5-4F column with running buffer (250 mM NaCl, 50 mM NaOAc, pH 6.0; at a flow rate of 0.35 mL/min. Eluted protein was detected by absorbance at 280 nm. To calculate the percentage of monomeric protein, area under the curve peaking at the monomer retention time was divided by the total area under curves not attributable to the sample matrix. The samples were stored at 4° C. and analyzed repeatedly over a period of 28 days (FIG. 1) at a concentration of 10 mg/mL.

Example 3: Generation of a Single-Chain Diabody (scDb) Format

For the functional characterization of the CD3 domain the selected domains were incorporated into the single-chain diabody format in order to test the domains potential to induce T-cell activation and target cell depletion.

The selected CD3 domain was incorporated into the single-chain diabody format either together with an IL23R-binding domain (anti-IL23R clone 14-11-D07, see SEQ ID NOs: 11 and 12; PRO624, see SEQ ID NO: 26) or with a HER2-binding domain (trastuzumab, see SEQ ID Nos: 20 and 21; PRO957, see SEQ ID NO: 27). In addition to the VL and VH domains from clone 28-21-D09 also VL and VH domains of two other published CD3 binders were tested (anti-CD3 clone 09-24-H09-sc10: see WO 2014/191113 and SEQ ID NOs: 9 and 10; anti-CD3 clone I2C: see US 2010/015091 8 and SEQ ID NOs: 13 and 14).

The construct design in the single-chain diabody (scDb) format was performed as described previously (Holliger et al., "Diabodies": small bivalent and bispecific antibody fragments. Proc. Natl. Acad. Sci. U.S.A. 90, 6444-6448). In short, the variable domains as listed in Table 1 were arranged in an VLA-L1-VHB-L2-VLB-L3-VHA fashion (see Table 5), where L1 and L3 are short $G_4S$ linkers (SEQ ID NO: 16) and L2 is a long $(G_4S)_4$ linker (SEQ ID NO: 15).

The nucleotide sequences were de novo synthesized and cloned into an adapted vector for E. coli expression that is based on a pET26b(+) backbone (Novagen). The expression construct was transformed into the E. coli strain BL12 (DE3) (Novagen) and the cells were cultivated in 2YT medium (Sambrook, J., et al., Molecular Cloning: A Laboratory Manual) as a starting culture. Expression cultures were inoculated and incubated in shake flasks at 37° C. and 200 rpm. Once an $OD_{600}$ of 1 had been reached protein expression was induced by the addition of IPTG at a final concentration of 0.5 mM. After overnight expression, the cells were harvested by centrifugation at 4,000 g. For the preparation of inclusion bodies, the cell pellet was resuspended in IB Resuspension Buffer (50 mM Tris-HCl pH 7.5, 100 mM NaCl, 5 mM EDTA, 0.5% Triton X-100). The cell slurry was supplemented with 1 mM DTT, 0.1 mg/mL lysozyme, 10 mM leupeptin, 100 μM PMSF and 1 μM pepstatin. Cells were lysed by 3 cycles of ultrasonic homogenization while being cooled on ice. Subsequently 0.01 mg/mL DNAse was added and the homogenate was incubated at room temperature for 20 min. The inclusion bodies (IBs) were sedimented by centrifugation at 15,000 g and 4° C. The IBs were resuspended in IB Resuspension buffer and homogenized by sonication before another centrifugation. In total a minimum of three washing steps with IB Resuspension Buffer were performed and subsequently two washes with IB Wash Buffer (50 mM Tris-HCl pH 7.5, 100 mM NaCl, 5 mM EDTA) to yield the final IBs.

For protein refolding the isolated IBs were resuspended in Solubilization Buffer (100 mM Tris/HCl pH 8.0, 6 M Gdn-HCl, 2 mM EDTA) in a ratio of 5 mL per g of wet IBs. The solubilization was incubated for 30 min at room temperature until DTT was added at a final concentration of 20 mM and the incubation was continued for another 30 min. After the solubilization was completed the solution was cleared by 10 min centrifugation at 21,500 g and 4° C. The refolding was performed by rapid dilution at a final protein concentration of 0.3 g/L of the solubilized protein in Refolding Buffer (typically: 100 mM Tris-HCl pH 8.0, 5.0 M urea, 5 mM cysteine,1 mM cystine). The refolding reaction was routinely incubated for a minimum of 14 h. The resulting protein solution was cleared by 10 min centrifugation at 8,500 g and 4° C. The refolded protein was purified by affinity chromatography on Capto L resin (GE Healthcare). The isolated monomer fraction was analyzed by size-exclusion HPLC, SDS-PAGE for purity and UV/Vis spectroscopy for protein content. Buffer was exchange into native buffer (50 mM citrate-phosphate pH 6.4, 200 mM NaCl) by dialysis. The protein concentrations were adjusted to the intended value for the stability analysis.

Figure 8A:
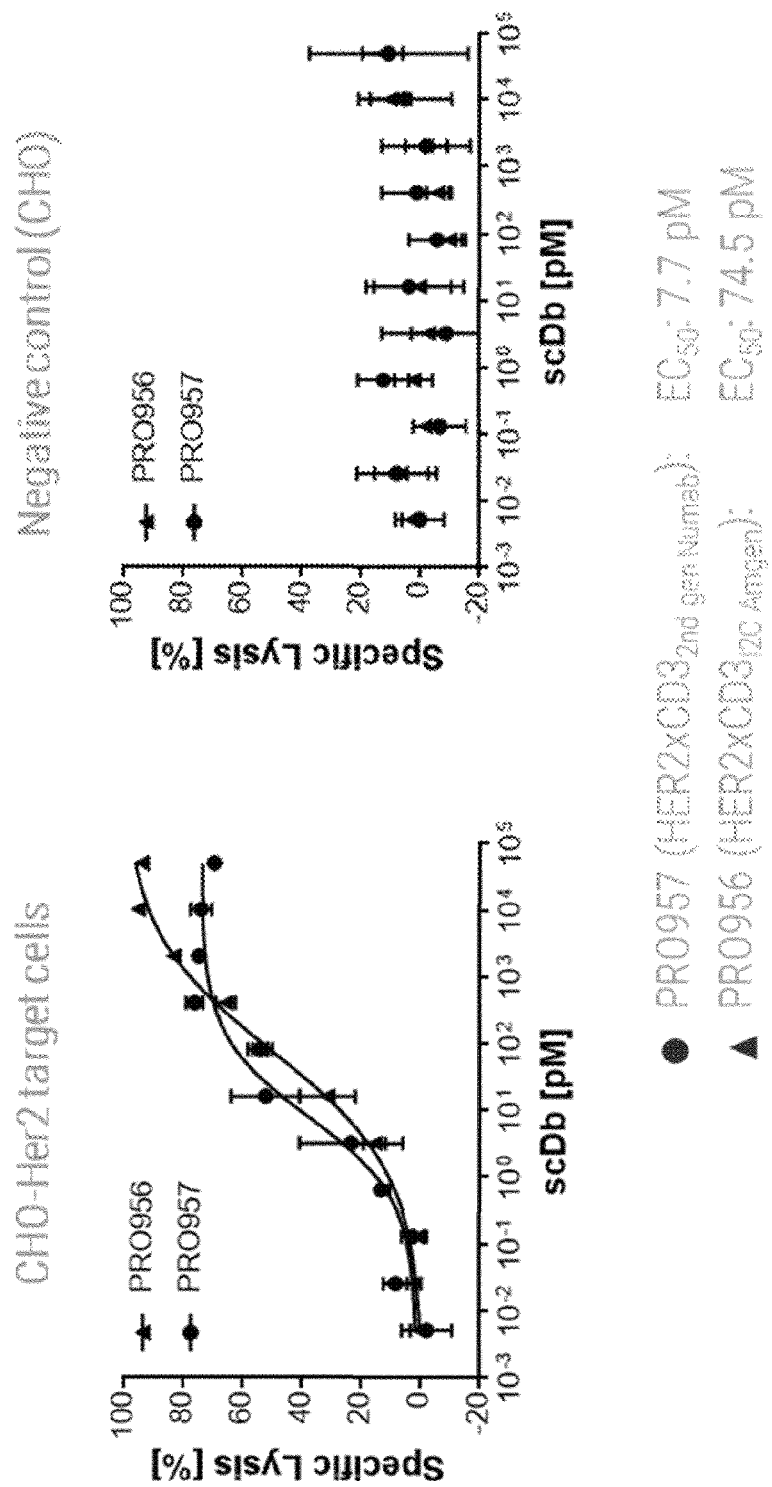
FIG. 8 shows the T-cell mediated target cell depletion induced by PRO957 (HER2×CD3$_{2nd\ gen\ Numab}$) and PRO956 (HER2×CD3$_{I2C\ Amgen}$) using human PBMCs after 16 hours (A) and after 40 hours (B). The left panel shows cell lysis of target-expressing cells, while the right panel shows cell lysis of target-negative cells. The numerical value of the half maximal effective concentration (EC$_{50}$) for the molecules in the presence of target-expressing cells is depicted below the graphs.
Figure 8B:
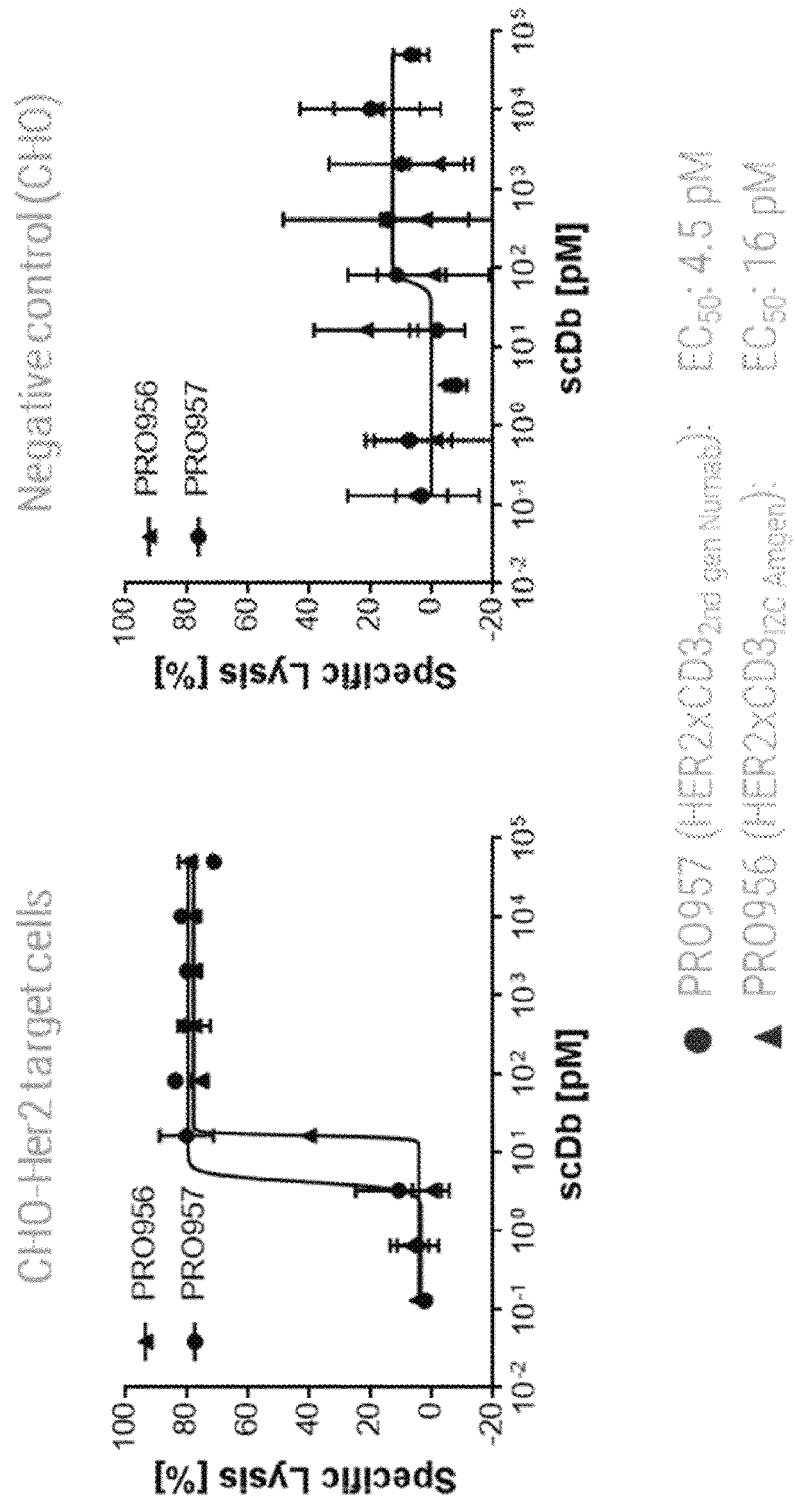
Figure 9A:
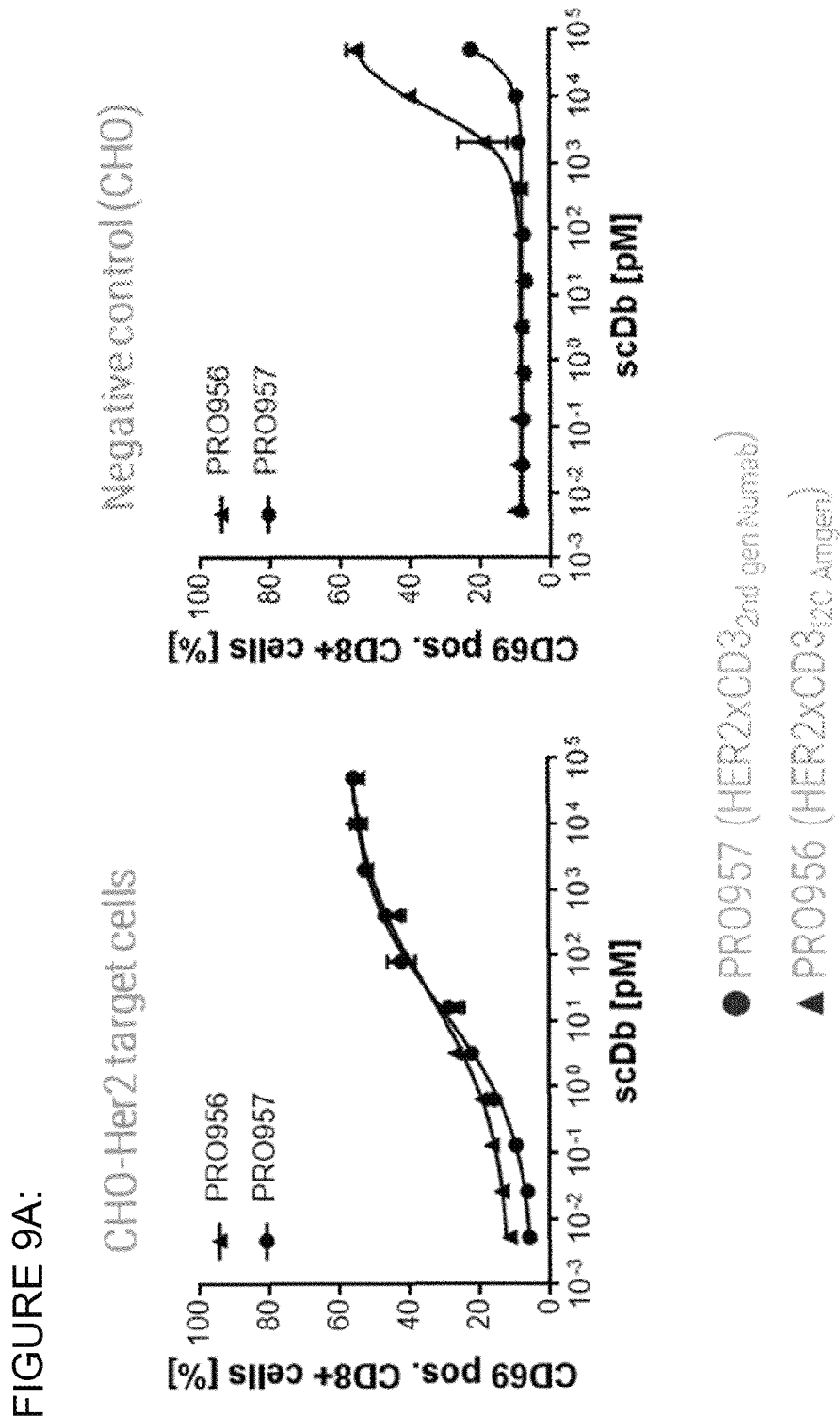
FIG. 9 shows the T-cell activation of the molecules PRO957 (HER2×CD3$_{2nd\ gen\ Numab}$) and PRO956 (HER2×CD3$_{I2C\ Amgen}$) determined by the FC assay after 16 hours (A) and after 40 hours (B). The left panel shows activation in presence of target-expressing cells, while the right panel shows activation in the presence of target-negative cells
Figure 9B:
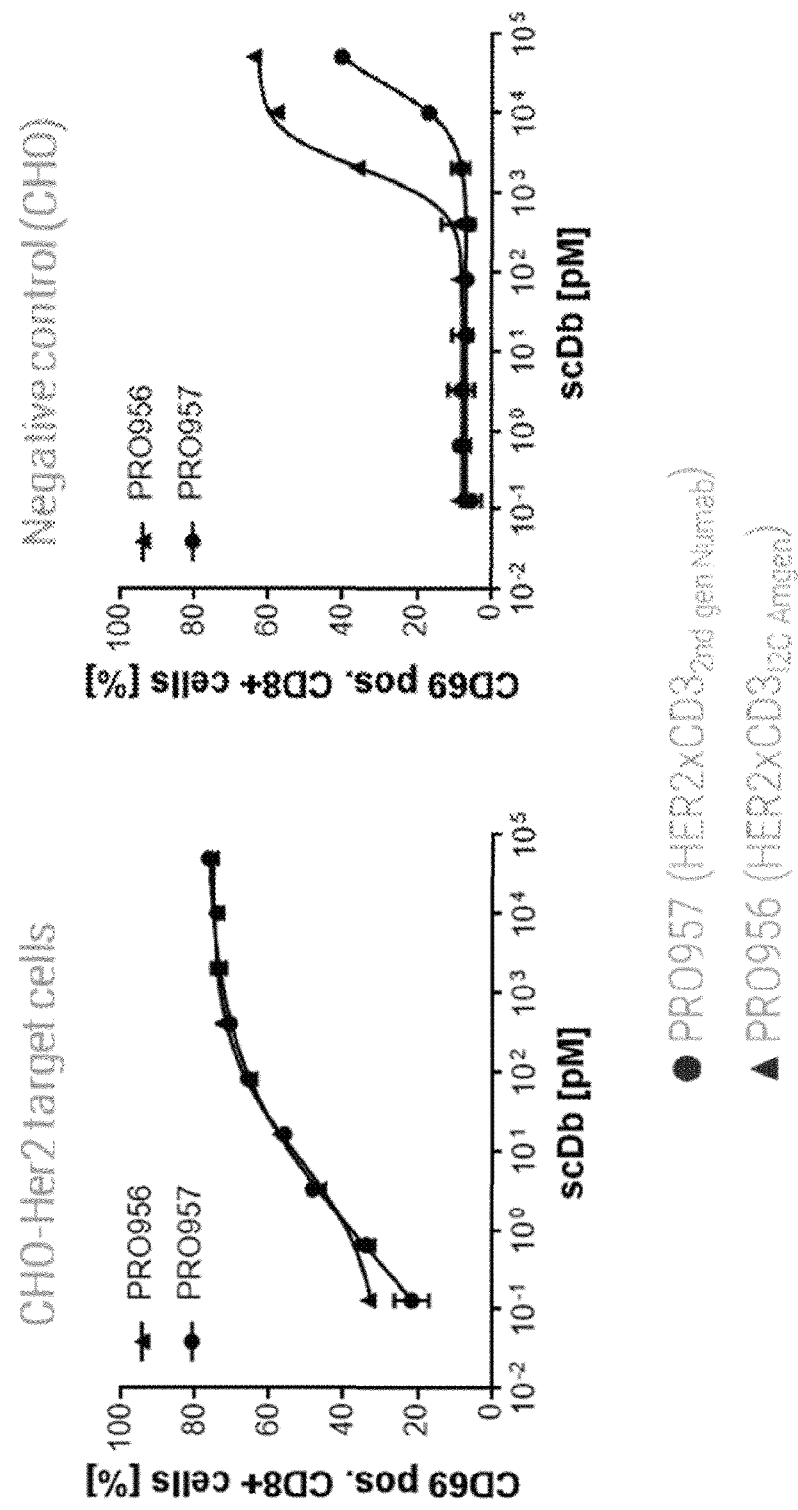

Example 4: Functional Characterization of the Single-Chain Diabody (scDb) Constructs 4.1 T-Cell Activation by NFAT Reporter Gene Assay The T-cell activation was tested in an NFAT assay. The Jurkat NFAT reporter T cell line expresses the luciferase reporter gene under control of the NFAT (nuclear factor of activated T-cells) response elements from the IL-2 promoter (GloResponse™ NFAT-luc2 Jurkat Cells). The transcription factor NFAT is activated upon cross-linking of CD3ε and induces a number of genes involved in T cell activation. In this system, cross-linking of CD3ε induces expression of the luciferase reporter gene. Transgenic IL-23R- (FIGS. 2 to 7) or HER2- (FIGS. 8 to 9) expressing Chinese Hamster Ovary (CHO-K1) cells were used as target cells and the parental CHO-K1 cell line was used as a negative control cell line. 25,000 viable target cells diluted in 50 µl assay medium (RPMI 1640, 10% FCS) were plated in white flat bottom 96-well plates. Then, 25 µl of 4 times concentrated test proteins diluted in assay medium were added to appropriate wells. Finally, 25 µl of assay medium containing 50,000 Jurkat cells was added to each well and plates were incubated first at RT for 10 min with gentle agitation and then transferred to 37° C., 5% $CO_2$ for 5 h. In order to detect luciferase activity, one step luciferase assay kit (Amsbio) was used according to manufacturer's instructions. Briefly, at the end of the incubation times, luciferase reagent substrate was mixed with the luciferase reagent buffer and 50 µl were added to each well and plates were incubated for 15 min in the dark at RT. Plates were read with the Flexstation III multi-mode microplate reader (Molecular Devices).

4.2 Cytotox Assay (T-Cell Driven Target Cell Depletion) Blood Cells Fractionation:

Peripheral blood mononuclear cells (PBMC) were isolated from fresh blood of healthy volunteers or healthy cynomolgus monkeys using the lymphocyte separation medium Lymphoprep (Stemcell technologies) according to manufacturer's instructions. Briefly, blood was diluted 1:2 with human PBMC isolation buffer (PBS, 2% FCS, 2 mM EDTA) or cynomolgus PBMCs isolation buffer (PBS, 5% FCS, 2 mM EDTA) and applied to Leucosep tubes containing recommended amount of Lymphoprep medium. LeucoSep tubes were centrifuged 30 min at 800 g (human blood) or 2,000 g (cynomolgus blood) without brakes at RT. Then, the cell layer containing PBMCs was collected and washed twice with human or cynomolgus PBMCs isolation buffer and red blood cells were lysed using red blood cells lysis buffer for 5 min at RT. Isolated human and cynomolgus cells were then washed once with their respective isolation buffer and once with assay medium (RPMI-1640, 10% FCS). After platelet removal, isolated PBMCs were resuspended in assay medium at a density $3 \times 10^6$ viable cells per ml.

Flow Cytometry-Based In Vitro Cytotoxicity Assay (FC Assay) and CD8+ T Cells Activation:

For anti-IL23R×CD3ε bispecific constructs transgenic IL-23R-expressing Chinese Hamster Ovary (CHO-K1) cells were used as target cells and the parental CHO-K1 cell line was used as a negative control cell line (FIGS. 2 to 7). For anti-HER2×anti-CD3ε bispecific constructs transgenic HER2 expressing Chinese Hamster Ovary (CHO-K1) cells were used (FIGS. 8 to 9). 5,000 viable target cells previously labelled with PKH67 and diluted in 75 µl of assay medium (RPMI-1640, 10% FCS) were added to 96-well plates. Next, 25 µl of 6 times concentrated test proteins diluted in assay medium were added to appropriate wells. Then, in order to have an E:T ratio of 30:1, 150,000 viable effector cells (PBMCs) diluted in 50 µl assay medium were added to each well and plates were mixed on a nutating mixer at RT prior to their incubation at 37° C., 5% $CO_2$. After 16 h, cells were trypsinized, resuspended in staining buffer (PBS, 2% BCS, 2 mM EDTA) and transferred into non-binding plates.

Cells were stained for different markers as CD69, CD8, CD4, CD11c and Annexin-V. For analysis, the focus is on apoptotic and dead target cells and activated CD8+ T cells. Thereby, target cells are identified by green fluorescence (PKH67) and their viability is analyzed by Annexin-V APC. Effector cells (CD8+ cells) were identified by detecting CD8 on their surface (anti-CD8 PerCP-Cy5.5). Activation of CD8+ T cells is finally detected by quantification of CD69 expression (anti-CD69 PE). CD4 is used to better discriminate CD8+ and CD4+ T cells. CD11c is used to mark monocytes and dendritic cells and exclude them. For each marker except Annexin-V antibodies are incubated 30 minutes at RT under gentle agitation. Cells are washed once with staining buffer, once with Annexin binding buffer and Annexin-V staining is carried on for 30 minutes at RT under agitation. Cells are washed once with Annexin-V binding buffer and flow cytometry analysis was done on a Novocyte Flow Cytometer.

The percentage of specific target cells lysis is calculated according to the following equation:

Specific lysis of target cells [in %]=[1−Viability target cells of sample/average viability of control samples]×100

The percentage of activated CD8+ T cells corresponds to the proportion of CD69+ CD8+ T cells.

Results

Comparison of Specificity of T-cell Activation

Figure 2:
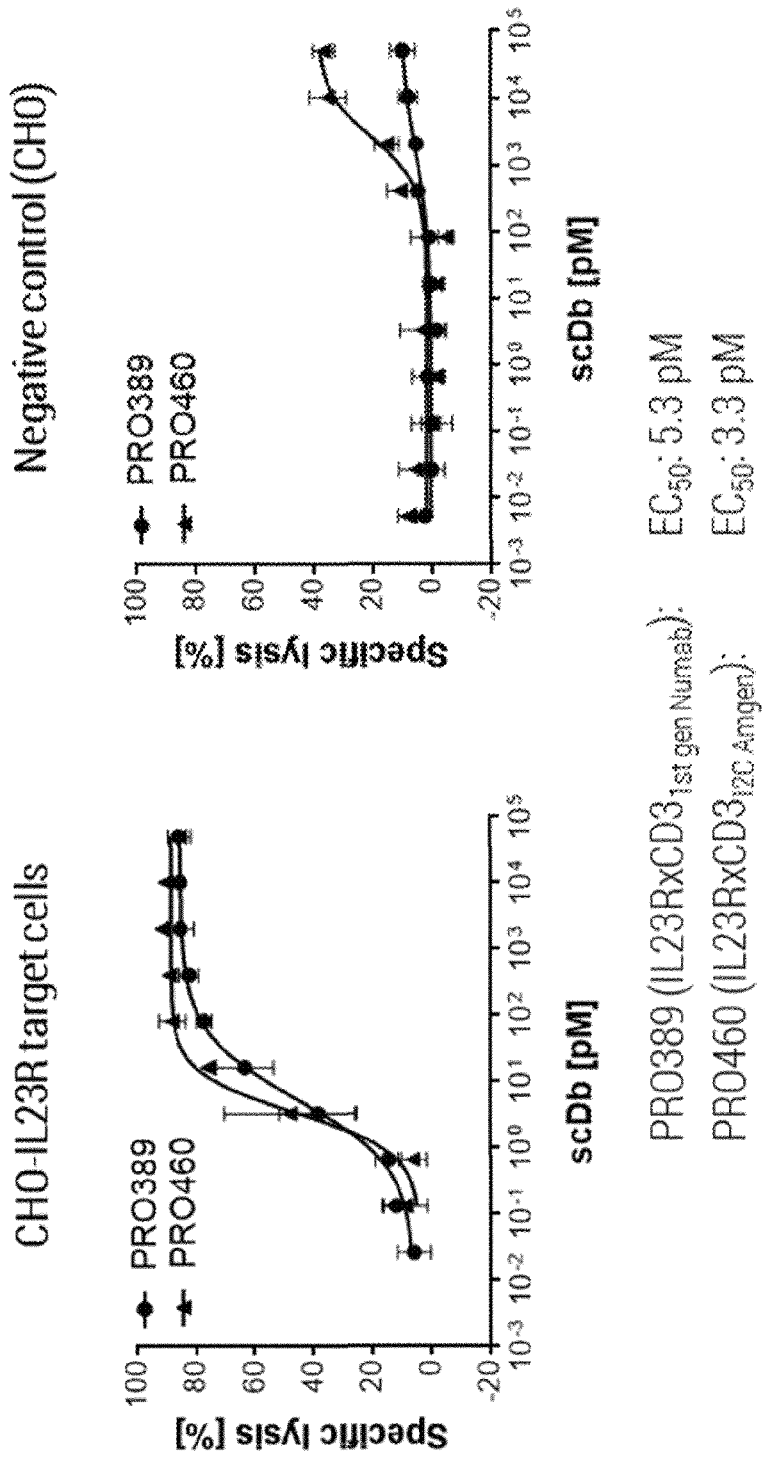
FIG. 2 shows the T-cell mediated target cell depletion induced by PRO460 (IL23R×CD3$_{I2C\ Amgen}$) and PRO389 (IL23R×CD3$_{1st\ gen\ Numab}$) using human PBMCs. The left panel shows cell lysis of target-expressing cells, while the right panel shows cell lysis of target-negative cells. The numerical value of the half maximal effective concentration (EC$_{50}$) for the molecules in the presence of target-expressing cells is depicted below the graphs.
Figure 3:
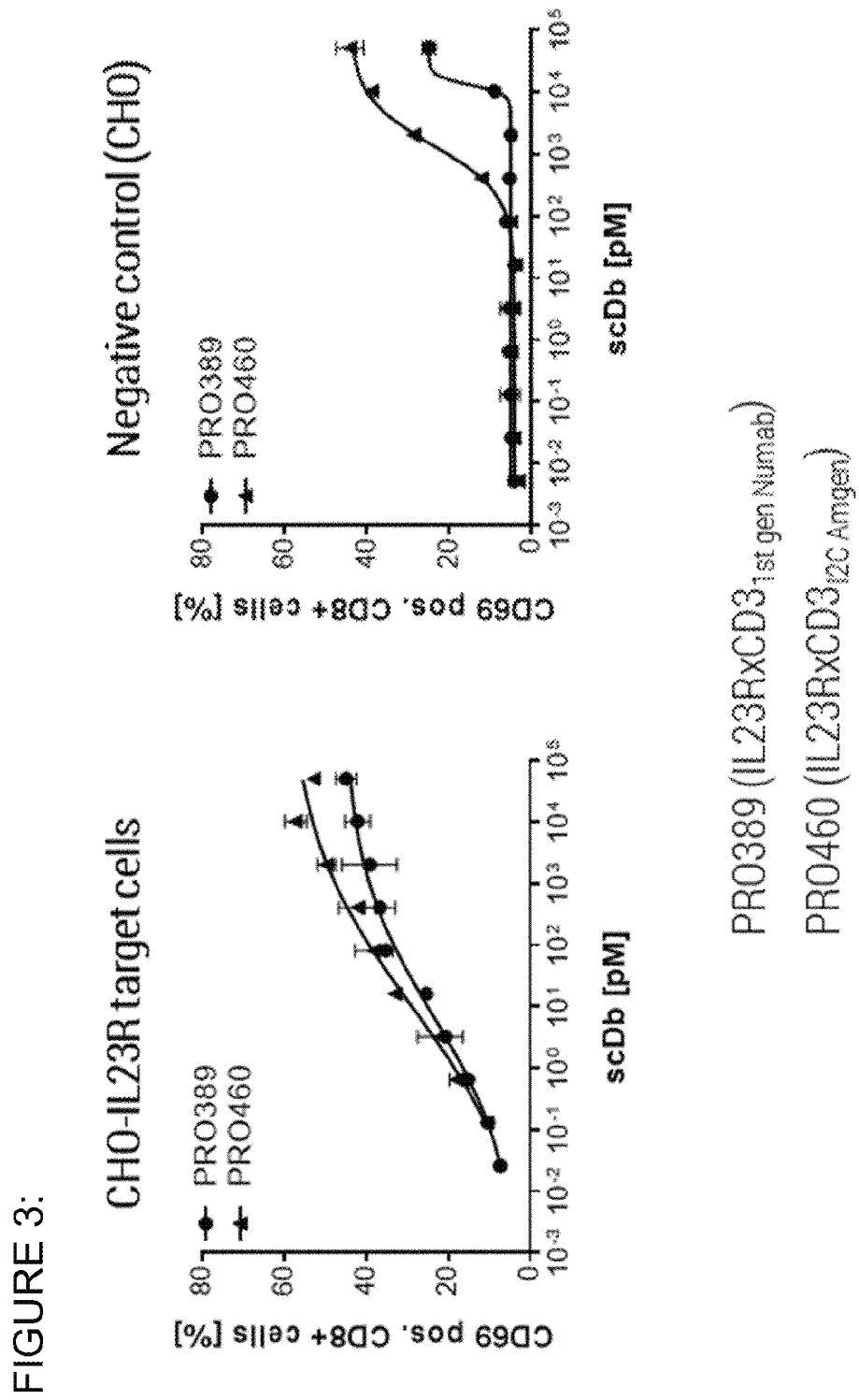
FIG. 3 shows the T-cell activation of the molecules PRO460 (IL23R×CD3$_{I2C}$ Amgen) and PRO389 (IL23R×CD3$_{1st\ gen\ Numab}$) determined by the FC assay. The left panel shows activation in the presence of target-expressing cells, while the right panel shows activation in the presence of target-negative cells.

Comparison of specific target cell lysis of target expressing cells mediated by PRO389 (IL23R×CD3$_{1st\ gen\ Numab}$) and PRO460 (IL23R×CD3$_{J2C\ Amgen}$) shows similar potency with an $EC_{50}$ of 5.3 and 3.3 pM, respectively (see FIG. 2). Also the attainable maximum level of lysis is identical for these two proteins. In combination with antigen-negative cells, however a difference manifests at higher concentrations of the molecules, where PRO460 (IL23R×CD3$_{I2C\ Amgen}$) causes a partial depletion of the negative control cells (FIG. 2). Quantification of the effector cell activation in the wells of the cytotoxicity assay by flow cytometry (FC) is in line with the results of the specific lysis. For the conditions which include target-positive cells a dose response is also observed for the activation of the effector cells. These results reveal a similar $EC_{50}$ of the effector cell activation, while the PRO389 (IL23R×CD3$_{1st\ gen\ Numab}$) apparently reaches a lower plateau for the maximal response (see FIG. 3). For the wells with the target-negative cells an apparent difference of the $EC_{50}$ for the unspecific activation distinguishes the two molecules. The administration of higher concentrations of both molecules leads to an increase of activated cells, even in the absence of target (FIG. 3). However, this effect is observed at about 25-fold lower concentrations of the molecule PRO460 (IL23R×CD3$_{I2C\ Amgen}$). Thus, the data provides evidence that the anti-CD3 domain in the PRO389 (IL23R×CD3$_{1st\ gen\ Numab}$) displays more specific T-cell activation in a head-to-head comparison to the anti-CD3 domain of PRO460 (IL23R×CD3$_{I2C\ Amgen}$) using the same format and target-binding domain.

The specific target cell depletion of the anti-CD3 domains in PRO389 (IL23R×CD3$_{1st\ gen\ Numab}$) and PRO624 (IL23R×CD3$_{2nd\ gen\ Numab}$) were compared in the cytotoxicity assay using human PBMCs. The two scDbs showed nearly identical properties in terms of target cell depletion of target-positive cells and lack of target cell depletion of target-negative cells (see FIG. 4). The quantification of the effector cell activation in the wells of the cytotoxicity assay by flow cytometry (FC) is in line with the results of the specific lysis. For the conditions which include target-positive cells a dose response is also observed for the activation of the effector cells, with both molecules resulting in similar responses. In the conditions containing target-negative cells an increase in activated effector cells is only observed at the highest condition tested (see FIG. 5).

In a confirmatory experiment, the potency of the molecules PRO624 (IL23R×CD3$_{2nd\ gen\ Numab}$) and PRO389 (IL23R×CD3$_{1st\ gen\ Numab}$) for T-cell activation was tested using the NFAT reporter gene assay. In the experiment, the nearly identical potency to induce T-cell activation in presence of antigen-positive cells was confirmed (see FIG. 6). While the $EC_{50}$ is shifted by about 8-fold to higher concentrations compared to the cell lysis (see FIG. 4), the data is in line with the activation data from the same experiment (see FIG. 5), which also shows an apparently 5-fold higher $EC_{50}$. In combination with antigen negative cells both molecules show only at the highest tested concentration of 50 nM an increase of the activation signal over baseline.

In conclusion, the results above show that the anti-CD3 domains incorporated in PRO624 (IL23R×CD3$_{2nd\ gen\ Numab}$) and PRO389 (IL23R×CD3$_{1st\ gen\ Numab}$) behave identical in terms of in-vitro potency and specificity to induce both, target cell depletion and T-cell activation. In comparison, while the anti-CD3 domain of PRO460 (IL23R×CD3$_{I2C\ Amgen}$) shows in the identical molecular background a comparable potency to activate T-cells in the presence of target cells and mediate their specific depletion, the PRO460 (IL23R×CD3$_{I2C\ Amgen}$) also shows an increased activation of T-cells in absence of target cells, which even causes cell lysis of target-negative cells.

In addition, comparison of specific target cell lysis of HER2-target-expressing cells mediated by PRO957 (HER2×CD3$_{2nd\ gen\ Numab}$) and PRO956 (HER2×CD3$_{I2C\ Amgen}$) was carried out. The comparison of specific target cell lysis of HER2-expressing target cells mediated by PRO957 (HER2×CD3$_{2nd\ gen\ Numab}$) and PRO956 (HER2×CD3$_{I2C\ Amgen}$) shows approximately 10-fold higher potency of PRO957 (HER2×CD3$_{2nd\ gen\ Numab}$) after 16 hours and approximately 3 to 4-fold higher potency after 40 hours (see FIG. 8A and 8B). After 40 hours both molecules reach the identical levels of specific lysis of target cells. Quantification of the effector cell activation in the wells of the cytotoxicity assay by flow cytometry (FC) is in line with the results of the specific lysis. For the conditions which include target-positive cells a dose response is also observed for the activation of the effector cells. These results reveal a similar $EC_{50}$ of the effector cell activation for PRO957 (HER2×CD3$_{2nd\ gen\ Numab}$) and PRO956 (HER2×CD3$_{I2C\ Amgen}$). However, for the wells with the target-negative cells an apparent difference of the $EC_{50}$ for the unspecific activation distinguishes PRO957 (HER2×CD3$_{2nd\ gen\ Numab}$) and PRO956 (HER2×CD3$_{I2C\ Amgen}$). The administration of higher concentrations of both molecules leads to an increase of activated cells, even in the absence of target. However, this effect is observed at about 25-fold lower concentrations of the molecule PRO956 (HER2×CD3$_{I2C\ Amgen}$) (see FIG. 9A and 9B). Moreover, when the anti-CD3 domain is tested in combination with an anti-HER2 binding domain, PRO957 (HER2×CD3$_{2nd\ gen\ Numab}$) shows superior potency and specificity to induce both, target cell depletion and T-cell activation compared to P R0956 (HER2×CD3$_{I2C\ Amgen}$).

4.3 Crossreactivity of PRO624 (IL23R×CD3$_{2nd\ gen\ Numab}$) and PRO 389 (IL23R×CD3$_{1st\ gen\ Numab}$) to Cynomolgus Monkey An important feature of the anti-CD3ε binding domain I2C (US 2010/0150918) is the cross-species reactivity to human and non-chimpanzee primates, which offers an advantage in the pre-clinical development of derived therapeutics. Both anti-CD3ε domains incorporated in PRO624 (IL23R×CD3$_{2nd\ gen\ Numab}$) and PRO389 (IL23R×CD3$_{1st\ gen\ Numab}$) bind to recombinant human and cyno CD3ε in SPR measurements (Table 3 and WO 2014/191113). However, the reactivity of the domains of clone 09-24-H09, which are incorporated in PRO389 (IL23R×CD3$_{1st\ gen\ Numab}$), was not maintained in the cellular context of plasma-membrane bound CD3ε. In contrast, the domains derived from clone 28-21-D09, present in PR0624 (IL23R×CD3$_{2nd\ gen\ Numab}$), display conserved species-reactivity also in cellular assays. These differential features have been characterized by cytotox assays using cynomolgus PBMCs as effector cells.

Figure 4:
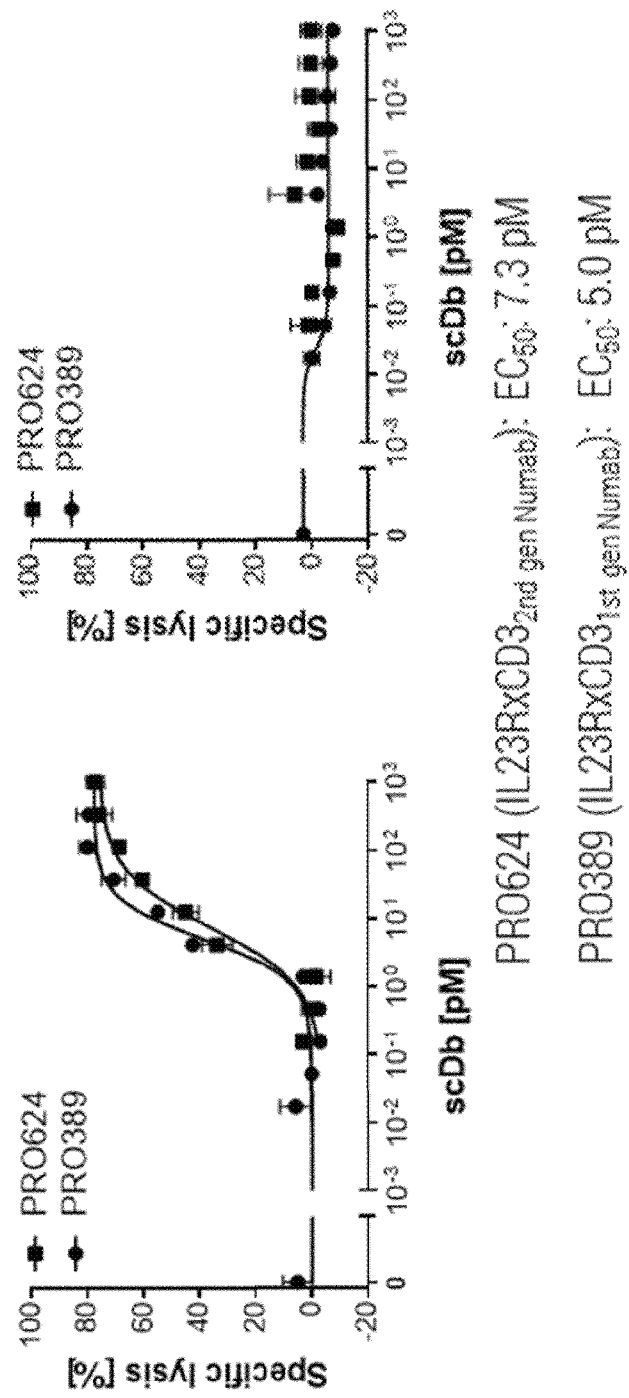
FIG. 4 shows the T-cell mediated target cell depletion induced by PRO624 (IL23R×CD3$_{2nd\ gen\ Numab}$) and PRO389 (IL23R×CD3$_{1st\ gen\ Numab}$) using human PBMCs. The left panel shows cell lysis of target-expressing cells, while the right panel shows cell lysis of target-negative cells. The numerical value of the half maximal effective concentration (EC$_{50}$) for the molecules in the presence of target-expressing cells is depicted below the graphs.
Figure 5:
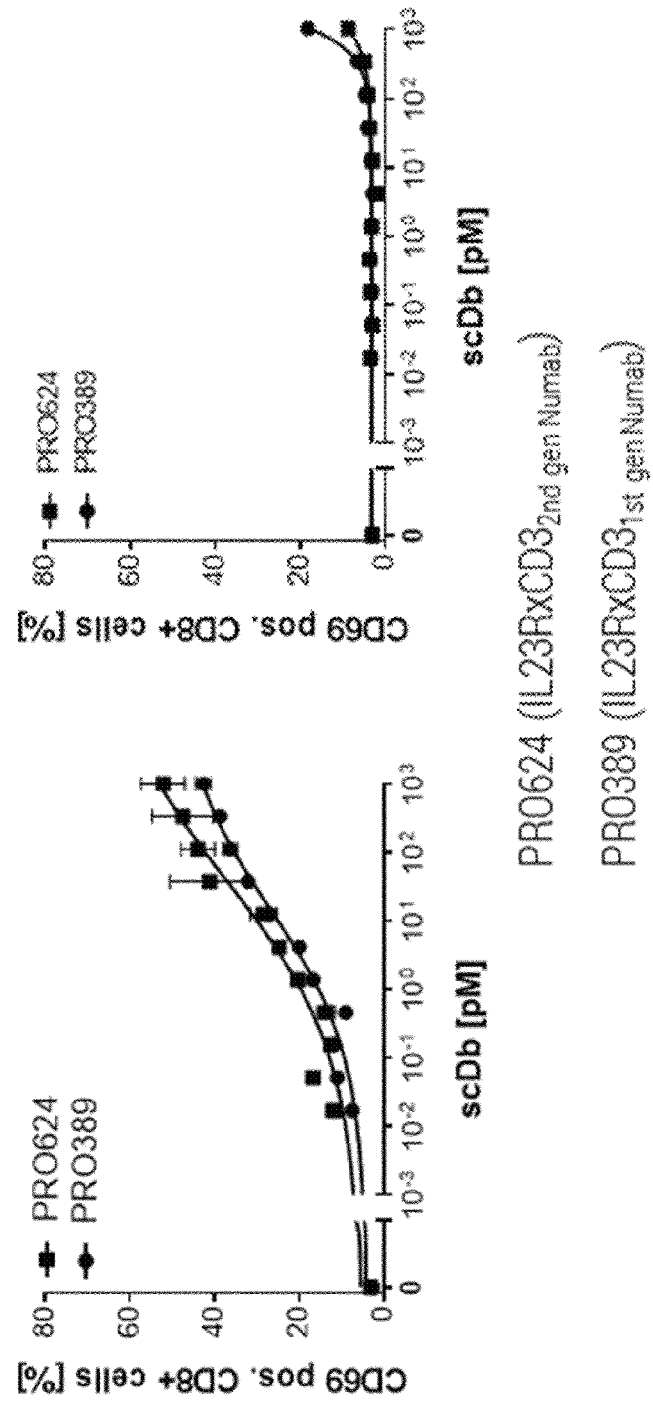
FIG. 5 shows the T-cell activation of the molecules PRO624 (IL23R×CD3$_{2nd\ gen\ Numab}$) and PRO389 (IL23R×CD3$_{1st\ gen\ Numab}$) determined by the FC assay. The left panel shows activation in the presence of target-expressing cells, while the right panel shows activation in the presence of target-negative cells.
Figure 6:
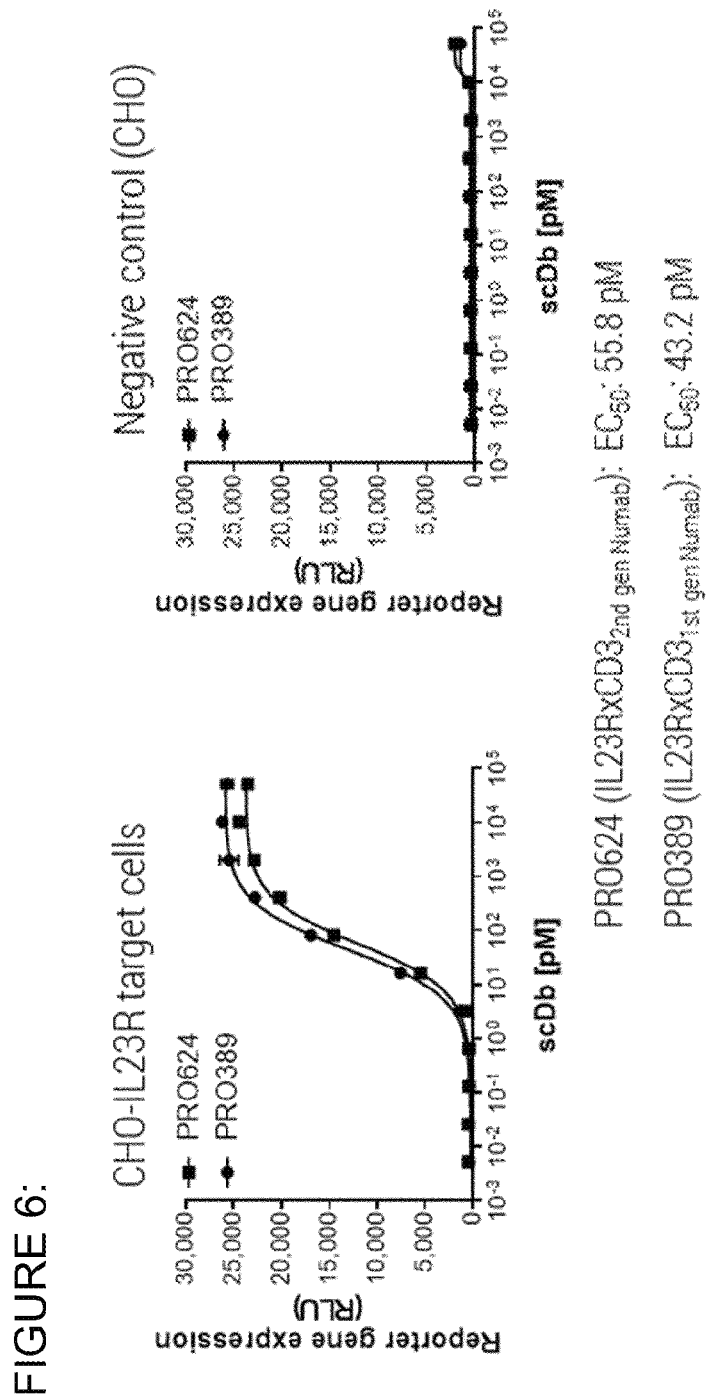
FIG. 6 shows the T-cell activation of the molecules PRO624 (IL23R×CD3$_{2nd\ gen\ Numab}$) and PRO389 (IL23R×CD3$_{1st\ gen\ Numab}$) determined by the NFAT reporter gene assay. The left panel shows activation in the presence of target-expressing cells, while the right panel shows activation in the presence of target-negative cells. The numerical value of the half maximal effective concentration (EC$_{50}$) for the molecules in the presence of target-expressing cells is depicted below the graphs.
Figure 7:
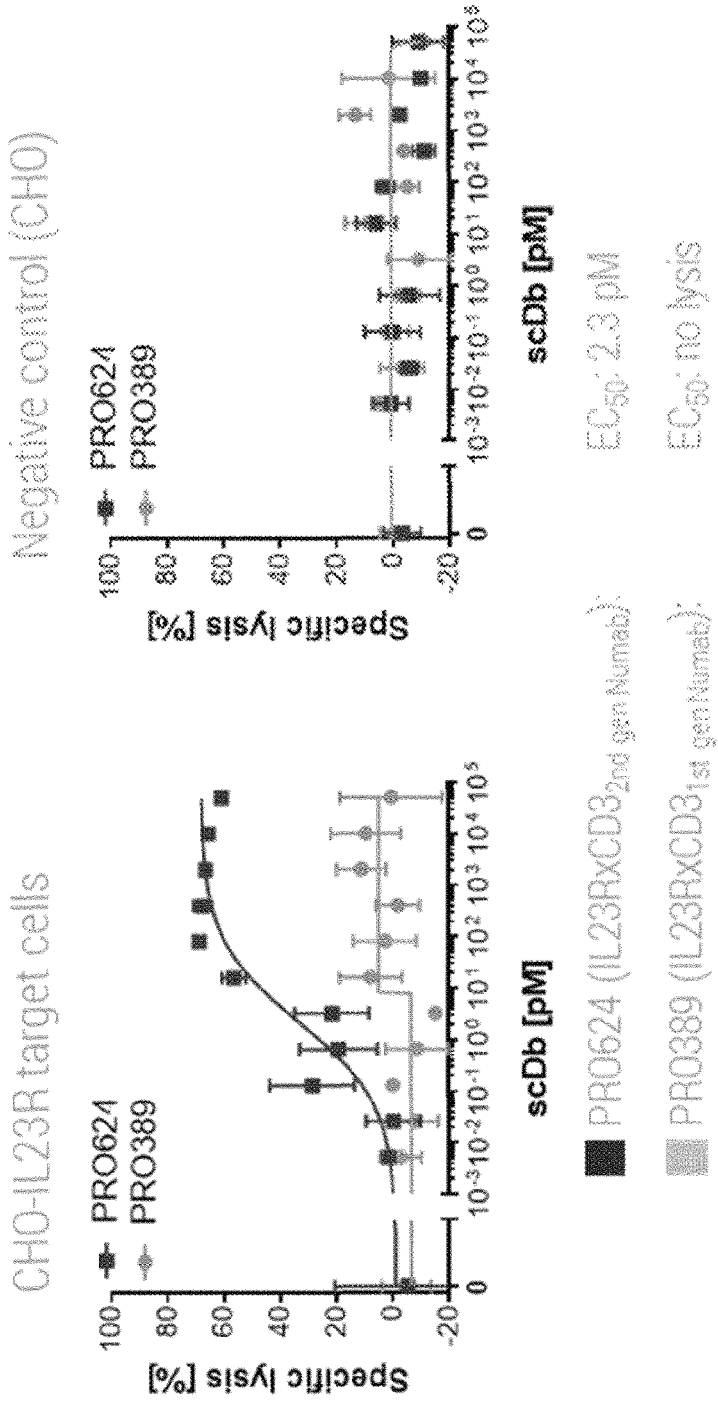
FIG. 7 shows the T-cell mediated target cell depletion induced by PRO624 (IL23R×CD3$_{2nd\ gen\ Numab}$) and PRO389 (IL23R×CD3$_{1st\ gen\ Numab}$) using cynomolgus PBMCs. The left panel shows cell lysis in of target-expressing cells, while the right panel shows cell lysis of target-negative cells. The numerical value of the half maximal effective concentration (EC$_{50}$) for the molecules in the presence of target-expressing cells is depicted below the graphs.

The data from the cytotox assay with cyno PBMCs (see FIG. 7) show a similar potency of PR0624 (IL23R×CD3$_{2nd\ gen\ Numab}$) to induce specific target cell depletion in comparison to using human effector cells (see FIG. 4). In addition, also in the context of target-negative cells there is no unspecific lysis of cells observed. The analysis of PRO389 (IL23R×CD3$_{1st\ gen\ Numab}$) on the other hand shows no depletion of target cells by the cyno effector cells. Further characterization of the domains revealed the absence of cell binding for PRO389 (IL23R×CD3$_{1st\ gen\ Numab}$) to cyno CD3ε expressing cells.

In conclusion, the surprising finding that the 09-24-H09 domains do not display relevant cross-species reactivity to human and non-chimpanzee primates results in only the domains 28-21-D09 to offer both, an advantage in specificity over the current state of the art and the desired feature of cross-species reactivity.

TABLE 1

Sequence listing (CDR residues shown in bold and italic letters

| Sequence ID (SEQ ID) | Description | Sequence |
|---|---|---|
| 1 | LCDR1 28-21-D09-sc04 | QSSQSVFSNNYLA |
| 2 | LCDR2 28-21-D09-sc04 | SASTLAS |
| 3 | LCDR3 28-21-D09-sc04 | LGSYACSSADCYV |
| 4 | Anti-CD3 VL 28-21-D09-sc04 | DIQMTQSPSSLSASVGDRVTITC*QSSQSVFSNNYLA*WFQQKPGQSPKRLIY*SASTLAS*GVPSRFSGSGSGTDFTLTISSLQPEDFATYYC*LGSYACSSADCYV*FGTGTKVTVLG |
| 5 | HCDR1 28-21-D09-sc04 | GFSLSSYDMS |
| 6 | HCDR2 28-21-D09-sc04 | ASYASGPTYYASWAKG |
| 7 | HCDR3 28-21-D09-sc04 | RGGWTGTSHSNI |
| 8 | Anti-CD3 VH 28-21-D09-sc04 | EVQLVESGGGLVQPGGSLRLSCAAS*GFSLSSYDMS*WVRQAPGKGLAWIG*ASYASGPTYYASWAKG*RFTISRDNSKNTVYLQMNSLRAEDTATYFCAR*GGWTGTSHSNI*WGQGTLVTVSS |
| 9 | Anti-CD3 VL 09-24-H09-sc10 | DIQMTQSPSSLSASVGDRVTITC*QSSESVYNNKRLS*WYQQKPGKAPKLLIY*TASSLAS*GVPSRFSGSGSGTDFTLTISSLQPEDFATYYC*QGEFTCSNADCFT*FGTGTKVTVLG |
| 10 | Anti-CD3 VH 09-24-H09-sc10 | EVQLVESGGGLVQPGGSLRLSCAAS*GFPLSSYAMI*WVRQAPGKGLEWIG*MILRAGNIYYASWVKG*RFTISRDNSKNTVYLQMNSLRAEDTAVYYCAR*RHYNREGYPIGIGDL*WGQGTLVTVSS |
| 11 | Anti-IL23R VL 14-11-D07-sc03 | DIQMTQSPSSLSASVGDRVTITC*QASENIYSFLA*WYQQKPGKAPKWY*SASKLAA*GVPSRFSGSGSGTDFTLTISSLQPEDFATYYC*QQTNRYSNPDIYNV*FGTGTKVTVLG |
| 12 | Anti-IL23R VH 14-11-D07-sc03 | EVQLVESGGGLVQPGGSLRLSCAAS*GIDFNSNYYMC*WVRQAPGKGLEWIG*CIYVGSHVNTYYANWAKG* RFTISRDNSKNTVYLQMNSLRAEDTAVYYCA*TSGSSVLYFKF*WGQGTLVTVSS |
| 13 | Anti-CD3 VL I2C | QTVVTQEPSLTVSPGGTVTLTC*GSSTGAVTSGNYPN*WVQQKPGQAPRGLIG*GTKFLAP*GTPARFSGSLLGGKAALTLSGVQPEDEAEYYC*VLWYSNRWV*FGGGTKLTVL |
| 14 | Anti-CD3 VH I2C | EVQLVESGGGLVQPGGSLKLSCAAS*GFTFNKYAMN*WVRQAPGKGLEWVA*RIRSKYNNYATYYADSVKD*RFTISRDDSKNTAYLQMNNLKTEDTAVYYCV*RHGNFGNSYISYWAY*WGQGTLVTVSS |
| 15 | Linker L2 | GGGGSGGGGSGGGGSGGGGS |
| 16 | Linker L1/L3 | GGGGS |
| 17 | Vλ germline-based FR4 (Sk17) | FGTGTKVTVLG |
| 18 | Vλ germ line-based FR4 (Sk12) | FGGGTKLTVLG |
| 19 | Human CD3ε | MQSGTHWRVLGLCLLSVGVWGQDGNEEMGGITQTPYKVSISGTTVILTCPQYPGSEILWQHNDKNIGGDEDDKNIGSDEDHLSLKEFSELEQSGYYVCYPRGSKPEDANFYLYLRARVCENCMEMDVMSVATIVIVDICITGGLLLLVYYWSKNRKAKAKPVTRGAGAGGRQRGQNKERPPPVPNPDYEPIRKGQRDLYSGLNQRRI |
| 20 | HER2 VL | DIQMTQSPSSLSASVGDRVTITC*RASQDVNTAVA*WYQQKPGKAPKLLIY*SASFLYS*GVPSRFSGSRSGTDFTLTISSLQPEDFATYYC*QQHYTTPPT*FGTGTKVTVLG |
| 21 | HER2 VH | EVQLVESGGGLVQPGGSLRLSCAAS*GFNIKDTYIH*WVRQAPGKGLEWVA*RIYPTNGYTRYADSVKG*RFTISADTSKNTAYLQMNSLRAEDTAVYYCS*RWGGDGFYAMDY*WGQGTLVTVSS |
| 22 | HSA VL 19-01-H04-sc03 | DIQMTQSPSSLSASVGDRVTITC*QSSESVYSNNQL*WYQQKPGQPPKLLIY*DASDLAS*GVPSRFSGSGSGTDFTLTISSLQPEDFATYYC*AGGFSSSSDTA*FGGGTKLTVLG |
| 23 | HSA VH 19-01-H04-sc03 | EVQLVESGGGLVQPGGSLRLSCAAS*GFSLSSNAMG*WVRQAPGKGLEYIGI*ISVGGFTYYASWAKG*RFTISRDNSKNTVYLQMNSLRAEDTATYFCAR*DRHGGDSSGAFYL*WGQGTLVTVSS |
| 24 | HSA VL 23-13-A01-sc03 | DVVMTQSPSSLSASVGDRVTITC*QASQIISSRSA*WYQQKPGQPPKLLIYQ*ASKLAS*GVPSRFSGSGSGTDFTLTISSLQPEDFATYYC*QCTYIDSNFGA*FGGGTKLTVLG |
| 25 | HSA VH 23-13-A01-sc03 | EVQLVESGGGLVQPGGSLRLSCAAS*GFSFSSSYWIC*WVRQAPGKGLEWVG*CVFTGDGTTYYASWAKG*RFTISRDNSKNTVYLQMNSLRAEDTATYFCAR*PVSVYYYGMDL*WGQGTLVTVSS |

TABLE 1-continued

Sequence listing (CDR residues shown in bold and italic letters

| Sequence ID (SEQ ID) | Description | Sequence |
|---|---|---|
| 26 | PRO624 (28-21-D09-sc04/14-11-D07-sc03) | DIQMTQSPSSLSASVGDRVTITCQASENIYSFLAWYQQKPGKAPKLLIYSASKLAAGVPSRFSG SGSGTDFTLTISSLQPEDFATYYCQQTNRYSNPDIYNVFGTGTKVTVLGGGGGSEVQLVESGG GLVQPGGSLRLSCAASGFSLSSYDMSWVRQAPGKGLAWIGASYASGPTYYASWAKGRFTISR DNSKNTVYLQMNSLRAEDTATYFCARGGWTGTSHSNIWGQGTLVTVSSGGGGSGGGGSGG GGSGGGGSDIQMTQSPSSLSASVGDRVTITCQSSQSVFSNNYLAWFQQKPGQSPKRLIYSAS TLASGVPSRFSGSGSGTDFTLTISSLQPEDFATYYCLGSYACSSADCYVFGTGTKVTVLGGGG GSEVQLVESGGGLVQPGGSLRLSCAASGIDFNSNYYMCWVRQAPGKGLEWIGCIYVGSHVNT YYANWAKGRFTISRDNSKNTVYLQMNSLRAEDTAVYYCATSGSSVLYFKFWGQGTLVTVSS |
| 27 | PRO957 (28-21-D09-sc04/anti-HER2) | DIQMTQSPSSLSASVGDRVTITCRASQDVNTAVAWYQQKPGKAPKLLIYSASFLYSGVPSRFSG SRSGTDFTLTISSLQPEDFATYYCQQHYTTPPTFGTGTKVTVLGGGGGSEVQLVESGGGLVQP GGSLRLSCAASGFSLSSYDMSWVRQAPGKGLAWIGASYASGPTYYASWAKGRFTISRDNSKN TVYLQMNSLRAEDTATYFCARGGWTGTSHSNIWGQGTLVTVSSGGGGSGGGGSGGGGSGG GGSDIQMTQSPSSLSASVGDRVTITCQSSQSVFSNNYLAWFQQKPGQSPKRLIYSASTLASGV PSRFSGSGSGTDFTLTISSLQPEDFATYYCLGSYACSSADCYVFGTGTKVTVLGGGGGSEVQL VESGGGLVQPGGSLRLSCAASGFNIKDTYIHWVRQAPGKGLEWVARIYPTNGYTRYADSVKG RFTISADTSKNTAYLQMNSLRAEDTAVYYCSRWGGDGFYAMDYWGQGTLVTVSS |
| 28 | 28-21-D09-sc14 (PRO718) | DIQMTQSPSSLSASVGDRVTITCQSSQSVFSNNYLAWYQQKPGQSPKLLIYSASTLASGVPSRF SGSGSGTDFTLTISSLQPEDFATYYCLGSYACSSADCYVFGTGTKVTVLGGGGSGGGGSGG GGSGGGGSEVQLVESGGGLVQPGGSLRLSCAASGFSLSSYDMSWVRQAPGKGLEWIGASYA SGPTYYASWAKGRFTISRDNSKNTVYLQMNSLRAEDTATYFCARGGWTGTSHSNIWGQGTLV TVSS |
| 29 | 28-21-D09-sc15 (PRO719) | DIQMTQSPSSLSASVGDRVTITCQSSQSVFSNNYLAWYQQKPGQSPKRLIYSASTLASGVPSR FSGSGSGTHFTLTISSLQPEDFATYYCLGSYACSSADCYVFGTGTKVTVLGGGGSGGGGSG GGGSGGGGSEVQLVESGGGLVQPGGSLRLSCAASGFSLSSYDMSWVRQAPGKGLEWIGASY ASGPTYYASWAKGRFTISRDNSKNTVYLQMNSLRAEDTATYFCARGGWTGTSHSNIWGQGTL VTVSS |
| 30 | 28-21-D09-sc16 (PRO720) | DIQMTQSPSSLSASVGDRVTITCQSSQSVFSNNYLAWYQQKPGQSPKRLIYSASTLASGVPSR FSGSGSGTDFTLTISSLQPEDFATYYCLGSYACSSADCYVFGTGTKVTVLGGGGSGGGGSG GGGSGGGGSEVQLVESGGGLVQPGGSLRLSCAASGFSLSSYDMSWVRQAPGKGLEWIGASY ASGPTYYASWAKGRFTISRDNSKNTVYLQMNSLRAEDTATYFCARGGWTGTSHSNIWGQGTL VTVSS |
| 31 | 28-21-D09-sc17 (PRO721) | DIQMTQSPSSLSASVGDRVTITCQSSQSVFSNNYLAWYQQKPGQSPKLLIYSASTLASGVPSRF SGSGSGTHFTLTISSLQPEDFATYYCLGSYACSSADCYVFGTGTKVTVLGGGGSGGGGSGG GGSGGGGSEVQLVESGGGLVQPGGSLRLSCAASGFSLSSYDMSWVRQAPGKGLEWIGASYA SGPTYYASWAKGRFTISRDNSKNTVYLQMNSLRAEDTATYFCARGGWTGTSHSNIWGQGTLV TVSS |
| 32 | 28-21-D09-sc18 (PRO722) | DIQMTQSPSSLSASVGDRVTITCQSSQSVFSNNYLAWYQQKPGQSPKRLIYSASTLASGVPSR FSGSGSGTHFTLTISSLQPEDFATYYCLGSYACSSADCYVFGTGTKVTVLGGGGSGGGGSG GGGSGGGGSEVQLVESGGGLVQPGGSLRLSCAASGFSLSSYDMSWVRQAPGKGLEWIGASY ASGPTYYASWAKGRFTISRDNSKNTVYLQMNSLRAEDTAVYYCARGGWTGTSHSNIWGQGTL VTVSS |
| 33 | 28-21-D09-sc19 (PRO723) | DIQMTQSPSSLSASVGDRVTITCQSSQSVFSNNYLAWYQQKPGQSPKRLIYSASTLASGVPSR FSGSGSGTDFTLTISSLQPEDFATYYCLGSYACSSADCYVFGTGTKVTVLGGGGSGGGGSG GGGSGGGGSEVQLVESGGGLVQPGGSLRLSCAASGFSLSSYDMSWVRQAPGKGLEWIGASY ASGPTYYASWAKGRFTISRDNSKNTVYLQMNSLRAEDTAVYYCARGGWTGTSHSNIWGQGTL VTVSS |
| 34 | 28-21-D09-sc20 (PRO724) | DIQMTQSPSSLSASVGDRVTITCQSSQSVFSNNYLAWYQQKPGQSPKLLIYSASTLASGVPSRF SGSGSGTHFTLTISSLQPEDFATYYCLGSYACSSADCYVFGTGTKVTVLGGGGSGGGGSGG GGSGGGGSEVQLVESGGGLVQPGGSLRLSCAASGFSLSSYDMSWVRQAPGKGLAWIGASYA SGPTYYASWAKGRFTISRDNSKNTVYLQMNSLRAEDTAVYYCARGGWTGTSHSNIWGQGTLV TVSS |
| 35 | 28-21-D09-sc21 (PRO801) | DIQMTQSPSSLSASVGDRVTITCQSSQSVFSNNYLAWYQQKPGQSPKRLIYSASTLASGVPSR FSGSGSGTDFTLTISSLQPEDFATYYCLGSYACSSADCYVFGTGTKVTVLGGGGSGGGGSG GGGSGGGGSEVQLVESGGGLVQPGGSLRLSCAASGFSLSSYDMSWVRQAPGKGLAWIGASY ASGPTYYASWAKGRFTISRDNSKNTVYLQMNSLRAEDTAVYYCARGGWTGTSHSNIWGQGTL VTVSS |
| 36 | 28-21-D09-sc22 (PRO802) | DIQMTQSPSSLSASVGDRVTITCQSSQSVFSNNYLAWFQQKPGQSPKRLIYSASTLASGVPSR FSGSGSGTDFTLTISSLQPEDFATYYCLGSYACSSADCYVFGTGTKVTVLGGGGSGGGGSG GGGSGGGGSEVQLVESGGGLVQPGGSLRLSCAASGFSLSSYDMSWVRQAPGKGLEWIGASY ASGPTYYASWAKGRFTISRDNSKNTVYLQMNSLRAEDTAVYYCARGGWTGTSHSNIWGQGTL VTVSS |

TABLE 1-continued

Sequence listing (CDR residues shown in bold and italic letters

| Sequence ID (SEQ ID) | Description | Sequence |
|---|---|---|
| 37 | 28-21-D09-sc23 (PRO803) | DIQMTQSPSSLSASVGDRVTITCQSSQSVFSNNYLAWYQQKPGKAPKRLIYSASTLASGVPSRF SGSGSGTDFTLTISSLQPEDFATYYCLGSYACSSADCYVFGTGTKVTVLGGGGSGGGGSGG GGSGGGGSEVQLVESGGGLVQPGGSLRLSCAASGFSLSSYDMSWVRQAPGKGLAWIGASYA SGPTYYASWAKGRFTISRDNSKNTVYLQMNSLRAEDTAVYYCARGGWTGTSHSNIWGQGTLV TVSS |
| 38 | 28-21-D09-sc24 (PRO804) | DIQMTQSPSSLSASVGDRVTITCQSSQSVFSNNYLAWYQQKPGQSPKKLIYSASTLASGVPSR FSGSGSGTDFTLTISSLQPEDFATYYCLGSYACSSADCYVFGTGTKVTVLGGGGSGGGGSG GGGSGGGGSEVQLVESGGGLVQPGGSLRLSCAASGFSLSSYDMSWVRQAPGKGLAWIGASY ASGPTYYASWAKGRFTISRDNSKNTVYLQMNSLRAEDTAVYYCARGGWTGTSHSNIWGQGTL VTVSS |
| 39 | 28-21-D09-sc25 (PRO805) | DIQMTQSPSSLSASVGDRVTITCQSSQSVFSNNYLAWYQQKPGQSPKRLIYSASTLASGVPSR FSGSGSGTDFTLTISSLQPEDFATYYCLGSYACSSADCYVFGTGTKVTVLGGGGSGGGGSG GGGSGGGGSEVQLVESGGGLVQPGGSLRLSCAASGFSLSSYDMSWVRQAPGKGLAWIGASY ASGPTYYASWAKGRFTISRDNSKNTVYLQMNSLRAEDTATYFCARGGWTGTSHSNIWGQGTL VTVSS |
| 40 | 28-21-D09-sc26 (PRO806) | DIQMTQSPSSLSASVGDRVTITCQSSQSVFSNNYLAWYQQKPGQSPKRLIYSASTLASGVPSR FSGSGSGTQFTLTISSLQPEDFATYYCLGSYACSSADCYVFGTGTKVTVLGGGGSGGGGSG GGGSGGGGSEVQLVESGGGLVQPGGSLRLSCAASGFSLSSYDMSWVRQAPGKGLAWIGASY ASGPTYYASWAKGRFTISRDNSKNTVYLQMNSLRAEDTAVYYCARGGWTGTSHSNIWGQGTL VTVSS |
| 41 | 28-21-D09-sc27 (PRO807) | DIQMTQSPSSLSASVGDRVTITCQSSQSVFSNNYLAWYQQKPGQSPKRLIYSASTLASGVPSR FSGSGSGTDFTLTISSLQPEDFATYYCLGSYACSSADCYVFGTGTKVTVLGGGGSGGGGSG GGGSGGGGSEVQLVESGGGLVQPGGSLRLSCAVSGFSLSSYDMSWVRQAPGKGLAWIGASY ASGPTYYASWAKGRFTISRDNSKNTVYLQMNSLRAEDTAVYYCARGGWTGTSHSNIWGQGTL VTVSS |
| 42 | 28-21-D09-sc28 (PRO868) | DIQMTQSPSSLSASVGDRVTITCQSSQSVFSNNYLAWFQQKPGKAPKRLIYSASTLASGVPSRF SGSGSGTDFTLTISSLQPEDFATYYCLGSYACSSADCYVFGTGTKVTVLGGGGSGGGGSGG GGSGGGGSEVQLVESGGGLVQPGGSLRLSCAASGFSLSSYDMSWVRQAPGKGLEWIGASYA SGPTYYASWAKGRFTISRDNSKNTVYLQMNSLRAEDTAVYYCARGGWTGTSHSNIWGQGTLV TVSS |

TABLE 2

Rabbit residues grafted in addition to the CDR regions
(numbering according to AHo) for clone 28-21-D09

| Construct | Structural residues grafted VL | | | | Structural residues grafted VH | | | |
|---|---|---|---|---|---|---|---|---|
| 28-21-D09-sc28 | Y44F | | | L54R | | | | |
| 28-21-D09-sc04 | Y44F | K50Q | A51S | L54R | | E53A | V103T | Y105F |
| 28-21-D09-sc22 | Y44F | K50Q | A51S | L54R | | | | |
| 28-21-D09-sc23 | | | | L54R | | E53A | | |
| 28-21-D09-sc26 | | K50Q | A51S | L54R | D88Q | E53A | | |
| 28-21-D09-sc21 | | K50Q | A51S | L54R | | E53A | | |
| 28-21-D09-sc15 | | K50Q | A51S | L54R | D88H | | V103T | Y105F |
| 28-21-D09-sc18 | | K50Q | A51S | L54R | D88H | | | |
| 28-21-D09-sc27 | | K50Q | A51S | L54R | | A25V E53A | | |
| 28-21-D09-sc16 | | K50Q | A51S | L54R | | | V103T | Y105F |
| 28-21-D09-sc19 | | K50Q | A51S | L54R | | | | |
| 28-21-D09-sc24 | | K50Q | A51S | L54K | | E53A | | |
| 28-21-D09-sc14 | | K50Q | A51S | | | | V103T | Y105F |
| 28-21-D09-sc17 | | K50Q | A51S | | D88H | | V103T | Y105F |
| 28-21-D09-sc20 | | K50Q | A51S | | D88H | | | |
| 28-21-D09-sc03 | | | | | | | | |

TABLE 3

Affinity data for anti-CD3 scFvs for human and cyno CD3ε, determined by SPR

| Construct | Affinity Human KD [M] | Affinity Cyno KD [M] |
|---|---|---|
| 28-21-D09-sc28 | 4.32E−09 | not available |
| 28-21-D09-sc04 | 5.52E−09 | 4.78E−09 |
| 28-21-D09-sc22 | 5.66E−09 | not available |
| 28-21-D09-sc23 | 9.65E−09 | not available |
| 28-21-D09-sc26 | 1.08E−08 | not available |
| 28-21-D09-sc21 | 1.18E−08 | not available |
| 28-21-D09-sc15 | 1.47E−08 | 1.37E−08 |
| 28-21-D09-sc18 | 1.55E−08 | 1.42E−08 |
| 28-21-D09-sc27 | 1.61E−08 | not available |
| 28-21-D09-sc16 | 1.76E−08 | 1.66E−08 |
| 28-21-D09-sc19 | 2.10E−08 | 1.95E−08 |
| 28-21-D09-sc24 | 3.39E−08 | not available |
| 28-21-D09-sc14 | no binding | no binding |
| 28-21-D09-sc17 | no binding | no binding |
| 28-21-D09-sc20 | no binding | no binding |
| 28-21-D09-sc03 | no binding | no binding |

TABLE 4

Thermal unfolding data of the various αCD3 scFv constructs

| Construct | Tm |
|---|---|
| 28-21-D09-sc28 | 61.9 |
| 28-21-D09-sc04 | 68.1 |
| 28-21-D09-sc22 | 69.5 |
| 28-21-D09-sc23 | 64.7 |
| 28-21-D09-sc26 | 65.1 |
| 28-21-D09-sc21 | 64.9 |
| 28-21-D09-sc15 | 62.9 |
| 28-21-D09-sc18 | 63.8 |
| 28-21-D09-sc27 | 61.3 |
| 28-21-D09-sc16 | 71.8 |
| 28-21-D09-sc19 | 76.0 |
| 28-21-D09-sc24 | 60.7 |
| 28-21-D09-sc25 |  |
| 28-21-D09-sc14 | 69.5 |
| 28-21-D09-sc17 | 70.7 |
| 28-21-D09-sc20 | 69.4 |
| 28-21-D09-sc03 |  |

TABLE 5

Anti-CD3/anti-IL23R diabody and anti-CD3/anti-HER2 diabody constructs

| scDb construct | VLA | Linker L1 | VHB | Linker L2 | VLB | Linker L3 | VHA |
|---|---|---|---|---|---|---|---|
| | | | SEQ ID NO: | | | | |
| PRO624 | 11 | 16 | 8  | 15 | 4  | 16 | 12 |
| PRO389 | 11 | 16 | 10 | 15 | 9  | 16 | 12 |
| PRO460 | 11 | 16 | 14 | 15 | 13 | 16 | 12 |
| PRO956 | 20 | 16 | 14 | 15 | 13 | 16 | 21 |
| PRO957 | 20 | 16 | 8  | 15 | 4  | 16 | 21 |

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

To the extent possible under the respective patent law, all patents, applications, publications, test methods, literature, and other materials cited herein are hereby incorporated by reference.

The invention claimed is:

1. An antibody or functional fragment thereof, which is specific for human CD3, comprising:

(a) a variable light chain domain,
wherein the variable light chain domain comprises, from N-terminus to C-terminus, the regions LFW1-LCDR1-LFW2-LCDR2-LFW3-LCDR3-LFW4, wherein each LFW designates a light chain framework region, and each LCDR designates a light chain complementarity-determining region, and wherein said LCDR1 is as set forth in SEQ ID NO: 1; said LCDR2 is as set forth in SEQ ID NO: 2; and said LCDR3 is as set forth in SEQ ID NO: 3; and (b) a variable heavy chain domain,
wherein the variable heavy chain domain comprises, from N-terminus to C-terminus, the regions HFW1-HCDR1-HFW2-HCDR2-HFW3-HCDR3-HFW4, wherein each HFW designates a heavy chain framework region, and each HCDR designates a heavy chain complementarity-determining region, and wherein said HCDR1 is as set forth in SEQ ID NO: 5; said HCDR2 is as set forth in SEQ ID NO: 6; and said HCDR3 is as set forth in SEQ ID NO: 7.

2. The antibody or the functional fragment thereof according to claim 1, wherein said variable light chain domain is a VK1 light chain domain, and/or wherein said variable heavy chain domain is a VH3 heavy chain domain.

3. The antibody or the functional fragment thereof according to claim 1, wherein said variable light chain domain exhibits at least 90% sequence identity to the amino acid sequence according to SEQ ID NO: 4, and/or wherein said variable heavy chain domain exhibits at least 90% sequence identity to the amino acid sequence according to SEQ ID NO: 8.

4. The antibody or the functional fragment thereof according to claim 1, wherein said variable light chain domain comprises an Arginine or a Lysine at the light chain amino acid position 54 according to AHo numbering.

5. The antibody or the functional fragment thereof according to claim 1, wherein said variable light chain domain comprises the amino acid sequence of SEQ ID NO: 4, and said variable heavy chain domain comprises the amino acid sequence of SEQ ID NO: 8.

6. The antibody or the functional fragment thereof according to claim 1, wherein said antibody or the functional fragment thereof is characterized by one or more of the following parameters:
   (i) a $K_D$ value for the binding to human CD3 of less than 40 nM as measured by surface plasmon resonance;
   (ii) a $K_D$ value for the binding to cynomolgous CD3 of less than 20 nM as measured by surface plasmon resonance; and
   (iii) an average midpoint of thermal unfolding temperature (Tm) exceeding at least 60° C. as determined by differential scanning fluorimetry.

7. A multispecific polypeptide comprising the antibody or the functional fragment thereof according to claim 1 and at least a second binding domain or a fragment thereof with specificity for a target different from CD3.

8. A pharmaceutical composition comprising the antibody or the functional fragment thereof of claim 1 and a pharmaceutically acceptable carrier and/or excipient.

9. A nucleic acid or a collection of nucleic acids encoding the antibody or the functional fragment thereof according to claim 1.

10. A vector or a collection of vectors comprising the nucleic acid or the collection of nucleic acids of claim 9.

11. A method for producing the antibody or the functional fragment thereof of claim 1, comprising the step of expressing a nucleic acid or a collection of nucleic acids encoding the antibody or the functional fragment thereof according to claim 1.

12. A method of generating a multispecific construct, comprising the step of
    cloning, in one or more steps, one or more nucleic acids encoding the antibody or the functional fragment thereof according to claim 1, into a multispecific construct comprising a nucleic acid encoding at least a second binding domain or a fragment thereof, and, optionally, a nucleic acid encoding one or more additional binding domains or fragments thereof.

13. The method of claim 12, wherein said second binding domain is a second antibody or a functional fragment thereof.

14. A pharmaceutical composition comprising the multispecific polypeptide of claim 7, and a pharmaceutically acceptable carrier and/or excipient.

15. A method of treating a disease, comprising the step of administering the multispecific polypeptide of claim 7 to a patient in need thereof, wherein the disease is inflammatory disease, autoimmune disease or cancer, and wherein the second binding domain or the fragment thereof is specific for IL23R or tumor associated antigen (TAA), respectively.

16. A method of treating a disease, comprising the step of administering the pharmaceutical composition of claim 14 to a patient in need thereof, wherein the disease is inflammatory disease, autoimmune disease or cancer, and wherein the second binding domain or the fragment thereof is specific for IL23R or tumor associated antigen (TAA), respectively.

\* \* \* \* \*

SEQUENCE LISTING

```
<160> NUMBER OF SEQ ID NOS: 44

<210> SEQ ID NO 1
<211> LENGTH: 13
<212> TYPE: PRT
<213> ORGANISM: Artificial Sequence
<220> FEATURE:
<223> OTHER INFORMATION: artificial CDR sequence

<400> SEQUENCE: 1

Gln Ser Ser Gln Ser Val Phe Ser Asn Asn Tyr Leu Ala
1               5                   10

<210> SEQ ID NO 2
<211> LENGTH: 7
<212> TYPE: PRT
<213> ORGANISM: Artificial Sequence
<220> FEATURE:
<223> OTHER INFORMATION: artificial CDR sequence

<400> SEQUENCE: 2

Ser Ala Ser Thr Leu Ala Ser
1               5

<210> SEQ ID NO 3
<211> LENGTH: 13
<212> TYPE: PRT
<213> ORGANISM: Artificial Sequence
```

```
<220> FEATURE:
<223> OTHER INFORMATION: artificial CDR sequence

<400> SEQUENCE: 3

Leu Gly Ser Tyr Ala Cys Ser Ser Ala Asp Cys Tyr Val
1               5                   10

<210> SEQ ID NO 4
<211> LENGTH: 114
<212> TYPE: PRT
<213> ORGANISM: Artificial Sequence
<220> FEATURE:
<223> OTHER INFORMATION: artificial VL sequence

<400> SEQUENCE: 4

Asp Ile Gln Met Thr Gln Ser Pro Ser Ser Leu Ser Ala Ser Val Gly
1               5                   10                  15

Asp Arg Val Thr Ile Thr Cys Gln Ser Ser Gln Ser Val Phe Ser Asn
            20                  25                  30

Asn Tyr Leu Ala Trp Phe Gln Gln Lys Pro Gly Gln Ser Pro Lys Arg
        35                  40                  45

Leu Ile Tyr Ser Ala Ser Thr Leu Ala Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Leu Gly Ser Tyr Ala Cys
                85                  90                  95

Ser Ser Ala Asp Cys Tyr Val Phe Gly Thr Gly Thr Lys Val Thr Val
            100                 105                 110

Leu Gly

<210> SEQ ID NO 5
<211> LENGTH: 10
<212> TYPE: PRT
<213> ORGANISM: Artificial Sequence
<220> FEATURE:
<223> OTHER INFORMATION: artificial CDR sequence

<400> SEQUENCE: 5

Gly Phe Ser Leu Ser Ser Tyr Asp Met Ser
1               5                   10

<210> SEQ ID NO 6
<211> LENGTH: 16
<212> TYPE: PRT
<213> ORGANISM: Artificial Sequence
<220> FEATURE:
<223> OTHER INFORMATION: artificial CDR sequence

<400> SEQUENCE: 6

Ala Ser Tyr Ala Ser Gly Pro Thr Tyr Tyr Ala Ser Trp Ala Lys Gly
1               5                   10                  15

<210> SEQ ID NO 7
<211> LENGTH: 12
<212> TYPE: PRT
<213> ORGANISM: Artificial Sequence
<220> FEATURE:
<223> OTHER INFORMATION: artificial CDR sequence

<400> SEQUENCE: 7

Arg Gly Gly Trp Thr Gly Thr Ser His Ser Asn Ile
1               5                   10
```

<210> SEQ ID NO 8
<211> LENGTH: 119
<212> TYPE: PRT
<213> ORGANISM: Artificial Sequence
<220> FEATURE:
<223> OTHER INFORMATION: artificial VH sequence

<400> SEQUENCE: 8

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Ser Tyr
            20                  25                  30

Asp Met Ser Trp Val Arg Gln Ala Pro Gly Lys Gly Leu Ala Trp Ile
        35                  40                  45

Gly Ala Ser Tyr Ala Ser Gly Pro Thr Tyr Tyr Ala Ser Trp Ala Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Ala Glu Asp Thr Ala Thr Tyr Phe Cys Ala
                85                  90                  95

Arg Gly Gly Trp Thr Gly Thr Ser His Ser Asn Ile Trp Gly Gln Gly
            100                 105                 110

Thr Leu Val Thr Val Ser Ser
        115

<210> SEQ ID NO 9
<211> LENGTH: 114
<212> TYPE: PRT
<213> ORGANISM: Artificial Sequence
<220> FEATURE:
<223> OTHER INFORMATION: artificial VL sequence

<400> SEQUENCE: 9

Asp Ile Gln Met Thr Gln Ser Pro Ser Ser Leu Ser Ala Ser Val Gly
1               5                   10                  15

Asp Arg Val Thr Ile Thr Cys Gln Ser Ser Glu Ser Val Tyr Asn Asn
            20                  25                  30

Lys Arg Leu Ser Trp Tyr Gln Gln Lys Pro Gly Lys Ala Pro Lys Leu
        35                  40                  45

Leu Ile Tyr Thr Ala Ser Ser Leu Ala Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Gln Gly Glu Phe Thr Cys
                85                  90                  95

Ser Asn Ala Asp Cys Phe Thr Phe Gly Thr Gly Thr Lys Val Thr Val
            100                 105                 110

Leu Gly

<210> SEQ ID NO 10
<211> LENGTH: 123
<212> TYPE: PRT
<213> ORGANISM: Artificial Sequence
<220> FEATURE:
<223> OTHER INFORMATION: artificial VH sequence

<400> SEQUENCE: 10

Glu Val Gln Leu Val Glu Ser Gly Gly Gly Leu Val Gln Pro Gly Gly

```
                1               5                       10                      15
            Ser Leu Arg Leu Ser Cys Ala Ala Ser Gly Phe Pro Leu Ser Ser Tyr
                            20                      25                      30

Ala Met Ile Trp Val Arg Gln Ala Pro Gly Lys Gly Leu Glu Trp Ile
                            35                      40                      45

Gly Met Ile Leu Arg Ala Gly Asn Ile Tyr Tyr Ala Ser Trp Val Lys
                            50                      55                      60

Gly Arg Phe Thr Ile Ser Arg Asp Asn Ser Lys Asn Thr Val Tyr Leu
            65                      70                      75                      80

Gln Met Asn Ser Leu Arg Ala Glu Asp Thr Ala Val Tyr Tyr Cys Ala
                            85                      90                      95

Arg Arg His Tyr Asn Arg Glu Gly Tyr Pro Ile Gly Ile Gly Asp Leu
                            100                     105                     110

Trp Gly Gln Gly Thr Leu Val Thr Val Ser Ser
                            115                     120
```

<210> SEQ ID NO 11
<211> LENGTH: 113
<212> TYPE: PRT
<213> ORGANISM: Artificial Sequence
<220> FEATURE:
<223> OTHER INFORMATION: artificial VL sequence

<400> SEQUENCE: 11

```
            Asp Ile Gln Met Thr Gln Ser Pro Ser Ser Leu Ser Ala Ser Val Gly
            1               5                       10                      15

Asp Arg Val Thr Ile Thr Cys Gln Ala Ser Glu Asn Ile Tyr Ser Phe
                            20                      25                      30

Leu Ala Trp Tyr Gln Gln Lys Pro Gly Lys Ala Pro Lys Leu Leu Ile
                            35                      40                      45

Tyr Ser Ala Ser Lys Leu Ala Ala Gly Val Pro Ser Arg Phe Ser Gly
                            50                      55                      60

Ser Gly Ser Gly Thr Asp Phe Thr Leu Thr Ile Ser Ser Leu Gln Pro
            65                      70                      75                      80

Glu Asp Phe Ala Thr Tyr Tyr Cys Gln Gln Thr Asn Arg Tyr Ser Asn
                            85                      90                      95

Pro Asp Ile Tyr Asn Val Phe Gly Thr Gly Thr Lys Val Thr Val Leu
                            100                     105                     110

Gly
```

<210> SEQ ID NO 12
<211> LENGTH: 121
<212> TYPE: PRT
<213> ORGANISM: Artificial Sequence
<220> FEATURE:
<223> OTHER INFORMATION: artificial VH sequence

<400> SEQUENCE: 12

```
            Glu Val Gln Leu Val Glu Ser Gly Gly Gly Leu Val Gln Pro Gly Gly
            1               5                       10                      15

Ser Leu Arg Leu Ser Cys Ala Ala Ser Gly Ile Asp Phe Asn Ser Asn
                            20                      25                      30

Tyr Tyr Met Cys Trp Val Arg Gln Ala Pro Gly Lys Gly Leu Glu Trp
                            35                      40                      45

Ile Gly Cys Ile Tyr Val Gly Ser His Val Asn Thr Tyr Tyr Ala Asn
                            50                      55                      60

Trp Ala Lys Gly Arg Phe Thr Ile Ser Arg Asp Asn Ser Lys Asn Thr
```

```
                65                  70                  75                  80
Val Tyr Leu Gln Met Asn Ser Leu Arg Ala Glu Asp Thr Ala Val Tyr
                    85                  90                  95

Tyr Cys Ala Thr Ser Gly Ser Ser Val Leu Tyr Phe Lys Phe Trp Gly
                    100                 105                 110

Gln Gly Thr Leu Val Thr Val Ser Ser
            115                 120
```

```
<210> SEQ ID NO 13
<211> LENGTH: 109
<212> TYPE: PRT
<213> ORGANISM: Artificial Sequence
<220> FEATURE:
<223> OTHER INFORMATION: artificial VL sequence

<400> SEQUENCE: 13

Gln Thr Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Ser Gly
                20                  25                  30

Asn Tyr Pro Asn Trp Val Gln Gln Lys Pro Gly Gln Ala Pro Arg Gly
            35                  40                  45

Leu Ile Gly Gly Thr Lys Phe Leu Ala Pro Gly Thr Pro Ala Arg Phe
        50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Val Leu Trp Tyr Ser Asn
                85                  90                  95

Arg Trp Val Phe Gly Gly Gly Thr Lys Leu Thr Val Leu
            100                 105
```

```
<210> SEQ ID NO 14
<211> LENGTH: 125
<212> TYPE: PRT
<213> ORGANISM: Artificial Sequence
<220> FEATURE:
<223> OTHER INFORMATION: artificial VH sequence

<400> SEQUENCE: 14

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Lys Tyr
                20                  25                  30

Ala Met Asn Trp Val Arg Gln Ala Pro Gly Lys Gly Leu Glu Trp Val
            35                  40                  45

Ala Arg Ile Arg Ser Lys Tyr Asn Asn Tyr Ala Thr Tyr Tyr Ala Asp
        50                  55                  60

Ser Val Lys Asp Arg Phe Thr Ile Ser Arg Asp Asp Ser Lys Asn Thr
65                  70                  75                  80

Ala Tyr Leu Gln Met Asn Leu Lys Thr Glu Asp Thr Ala Val Tyr
                85                  90                  95

Tyr Cys Val Arg His Gly Asn Phe Gly Asn Ser Tyr Ile Ser Tyr Trp
                100                 105                 110

Ala Tyr Trp Gly Gln Gly Thr Leu Val Thr Val Ser Ser
            115                 120                 125
```

```
<210> SEQ ID NO 15
<211> LENGTH: 20
```

-continued

```
<212> TYPE: PRT
<213> ORGANISM: Artificial Sequence
<220> FEATURE:
<223> OTHER INFORMATION: artificial linker sequence

<400> SEQUENCE: 15

Gly Gly Gly Gly Ser Gly Gly Gly Gly Ser Gly Gly Gly Gly Ser Gly
1               5                   10                  15

Gly Gly Gly Ser
            20

<210> SEQ ID NO 16
<211> LENGTH: 5
<212> TYPE: PRT
<213> ORGANISM: Artificial Sequence
<220> FEATURE:
<223> OTHER INFORMATION: artificial linker sequence

<400> SEQUENCE: 16

Gly Gly Gly Gly Ser
1               5

<210> SEQ ID NO 17
<211> LENGTH: 11
<212> TYPE: PRT
<213> ORGANISM: Artificial Sequence
<220> FEATURE:
<223> OTHER INFORMATION: artificial FW4 sequence

<400> SEQUENCE: 17

Phe Gly Thr Gly Thr Lys Val Thr Val Leu Gly
1               5                   10

<210> SEQ ID NO 18
<211> LENGTH: 11
<212> TYPE: PRT
<213> ORGANISM: Artificial Sequence
<220> FEATURE:
<223> OTHER INFORMATION: artificial FW4 sequence

<400> SEQUENCE: 18

Phe Gly Gly Gly Thr Lys Leu Thr Val Leu Gly
1               5                   10

<210> SEQ ID NO 19
<211> LENGTH: 207
<212> TYPE: PRT
<213> ORGANISM: Homo sapiens

<400> SEQUENCE: 19

Met Gln Ser Gly Thr His Trp Arg Val Leu Gly Leu Cys Leu Leu Ser
1               5                   10                  15

Val Gly Val Trp Gly Gln Asp Gly Asn Glu Glu Met Gly Gly Ile Thr
                20                  25                  30

Gln Thr Pro Tyr Lys Val Ser Ile Ser Gly Thr Thr Val Ile Leu Thr
            35                  40                  45

Cys Pro Gln Tyr Pro Gly Ser Glu Ile Leu Trp Gln His Asn Asp Lys
        50                  55                  60

Asn Ile Gly Gly Asp Glu Asp Asp Lys Asn Ile Gly Ser Asp Glu Asp
65                  70                  75                  80

His Leu Ser Leu Lys Glu Phe Ser Glu Leu Glu Gln Ser Gly Tyr Tyr
                85                  90                  95

Val Cys Tyr Pro Arg Gly Ser Lys Pro Glu Asp Ala Asn Phe Tyr Leu
```

```
                  100                 105                 110
Tyr Leu Arg Ala Arg Val Cys Glu Asn Cys Met Glu Met Asp Val Met
            115                 120                 125

Ser Val Ala Thr Ile Val Ile Val Asp Ile Cys Ile Thr Gly Gly Leu
130                 135                 140

Leu Leu Leu Val Tyr Tyr Trp Ser Lys Asn Arg Lys Ala Lys Ala Lys
145                 150                 155                 160

Pro Val Thr Arg Gly Ala Gly Ala Gly Gly Arg Gln Arg Gly Gln Asn
                165                 170                 175

Lys Glu Arg Pro Pro Pro Val Pro Asn Pro Asp Tyr Glu Pro Ile Arg
            180                 185                 190

Lys Gly Gln Arg Asp Leu Tyr Ser Gly Leu Asn Gln Arg Arg Ile
                195                 200                 205

<210> SEQ ID NO 20
<211> LENGTH: 108
<212> TYPE: PRT
<213> ORGANISM: Artificial Sequence
<220> FEATURE:
<223> OTHER INFORMATION: artificial VL sequence

<400> SEQUENCE: 20

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
                20                  25                  30

Val Ala Trp Tyr Gln Gln Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Thr Gly Thr Lys Val Thr Val Leu Gly
            100                 105

<210> SEQ ID NO 21
<211> LENGTH: 120
<212> TYPE: PRT
<213> ORGANISM: Artificial Sequence
<220> FEATURE:
<223> OTHER INFORMATION: artificial VH sequence

<400> SEQUENCE: 21

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
                20                  25                  30

Tyr Ile His Trp Val Arg Gln Ala Pro Gly Lys Gly Leu Glu Trp Val
            35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95
```

Ser Arg Trp Gly Gly Asp Gly Phe Tyr Ala Met Asp Tyr Trp Gly Gln
            100                 105                 110

Gly Thr Leu Val Thr Val Ser Ser
        115                 120

<210> SEQ ID NO 22
<211> LENGTH: 112
<212> TYPE: PRT
<213> ORGANISM: Artificial Sequence
<220> FEATURE:
<223> OTHER INFORMATION: artificial VL sequence

<400> SEQUENCE: 22

Asp Ile Gln Met Thr Gln Ser Pro Ser Ser Leu Ser Ala Ser Val Gly
1               5                   10                  15

Asp Arg Val Thr Ile Thr Cys Gln Ser Ser Glu Ser Val Tyr Ser Asn
            20                  25                  30

Asn Gln Leu Ser Trp Tyr Gln Gln Lys Pro Gly Gln Pro Pro Lys Leu
        35                  40                  45

Leu Ile Tyr Asp Ala Ser Asp Leu Ala Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Ala Gly Phe Ser Ser
                85                  90                  95

Ser Ser Asp Thr Ala Phe Gly Gly Gly Thr Lys Leu Thr Val Leu Gly
            100                 105                 110

<210> SEQ ID NO 23
<211> LENGTH: 121
<212> TYPE: PRT
<213> ORGANISM: Artificial Sequence
<220> FEATURE:
<223> OTHER INFORMATION: artificial VH sequence

<400> SEQUENCE: 23

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Ser Asn
            20                  25                  30

Ala Met Gly Trp Val Arg Gln Ala Pro Gly Lys Gly Leu Glu Tyr Ile
        35                  40                  45

Gly Ile Ile Ser Val Gly Gly Phe Thr Tyr Tyr Ala Ser Trp Ala Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Ala Glu Asp Thr Ala Thr Tyr Phe Cys Ala
                85                  90                  95

Arg Asp Arg His Gly Gly Asp Ser Ser Gly Ala Phe Tyr Leu Trp Gly
            100                 105                 110

Gln Gly Thr Leu Val Thr Val Ser Ser
        115                 120

<210> SEQ ID NO 24
<211> LENGTH: 110
<212> TYPE: PRT
<213> ORGANISM: Artificial Sequence
<220> FEATURE:
<223> OTHER INFORMATION: artificial VL sequence

<400> SEQUENCE: 24

Asp Val Val Met Thr Gln Ser Pro Ser Leu Ser Ala Ser Val Gly
1               5                   10                  15

Asp Arg Val Thr Ile Thr Cys Gln Ala Ser Gln Ile Ile Ser Ser Arg
            20                  25                  30

Ser Ala Trp Tyr Gln Gln Lys Pro Gly Gln Pro Pro Lys Leu Leu Ile
        35                  40                  45

Tyr Gln Ala Ser Lys Leu Ala Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Cys Thr Tyr Ile Asp Ser Asn
                85                  90                  95

Phe Gly Ala Phe Gly Gly Gly Thr Lys Leu Thr Val Leu Gly
            100                 105                 110

<210> SEQ ID NO 25
<211> LENGTH: 121
<212> TYPE: PRT
<213> ORGANISM: Artificial Sequence
<220> FEATURE:
<223> OTHER INFORMATION: artificial VH sequence

<400> SEQUENCE: 25

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Ser Ser
            20                  25                  30

Tyr Trp Ile Cys Trp Val Arg Gln Ala Pro Gly Lys Gly Leu Glu Trp
        35                  40                  45

Val Gly Cys Val Phe Thr Gly Asp Gly Thr Thr Tyr Tyr Ala Ser Trp
50                  55                  60

Ala Lys Gly Arg Phe Thr Ile Ser Arg Asp Asn Ser Lys Asn Thr Val
65                  70                  75                  80

Tyr Leu Gln Met Asn Ser Leu Arg Ala Glu Asp Thr Ala Thr Tyr Phe
                85                  90                  95

Cys Ala Arg Pro Val Ser Val Tyr Tyr Tyr Gly Met Asp Leu Trp Gly
            100                 105                 110

Gln Gly Thr Leu Val Thr Val Ser Ser
        115                 120

<210> SEQ ID NO 26
<211> LENGTH: 497
<212> TYPE: PRT
<213> ORGANISM: Artificial Sequence
<220> FEATURE:
<223> OTHER INFORMATION: artificial diabody sequence

<400> SEQUENCE: 26

Asp Ile Gln Met Thr Gln Ser Pro Ser Ser Leu Ser Ala Ser Val Gly
1               5                   10                  15

Asp Arg Val Thr Ile Thr Cys Gln Ala Ser Glu Asn Ile Tyr Ser Phe
            20                  25                  30

Leu Ala Trp Tyr Gln Gln Lys Pro Gly Lys Ala Pro Lys Leu Leu Ile
        35                  40                  45

Tyr Ser Ala Ser Lys Leu Ala Ala Gly Val Pro Ser Arg Phe Ser Gly
50                  55                  60

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Thr Asn Arg Tyr Ser Asn
             85                   90                  95

Pro Asp Ile Tyr Asn Val Phe Gly Thr Gly Thr Lys Val Thr Val Leu
            100                 105                 110

Gly Gly Gly Gly Ser Glu Val Gln Leu Val Glu Ser Gly Gly Gly
        115                 120                 125

Leu Val Gln Pro Gly Gly Ser Leu Arg Leu Ser Cys Ala Ala Ser Gly
        130                 135                 140

Phe Ser Leu Ser Ser Tyr Asp Met Ser Trp Val Arg Gln Ala Pro Gly
145                 150                 155                 160

Lys Gly Leu Ala Trp Ile Gly Ala Ser Tyr Ala Ser Gly Pro Thr Tyr
                165                 170                 175

Tyr Ala Ser Trp Ala Lys Gly Arg Phe Thr Ile Ser Arg Asp Asn Ser
            180                 185                 190

Lys Asn Thr Val Tyr Leu Gln Met Asn Ser Leu Arg Ala Glu Asp Thr
        195                 200                 205

Ala Thr Tyr Phe Cys Ala Arg Gly Gly Trp Thr Gly Thr Ser His Ser
    210                 215                 220

Asn Ile Trp Gly Gln Gly Thr Leu Val Thr Val Ser Ser Gly Gly Gly
225                 230                 235                 240

Gly Ser Gly Gly Gly Gly Ser Gly Gly Gly Gly Ser Gly Gly Gly Gly
                245                 250                 255

Ser Asp Ile Gln Met Thr Gln Ser Pro Ser Ser Leu Ser Ala Ser Val
            260                 265                 270

Gly Asp Arg Val Thr Ile Thr Cys Gln Ser Ser Gln Ser Val Phe Ser
        275                 280                 285

Asn Asn Tyr Leu Ala Trp Phe Gln Gln Lys Pro Gly Gln Ser Pro Lys
290                 295                 300

Arg Leu Ile Tyr Ser Ala Ser Thr Leu Ala Ser Gly Val Pro Ser Arg
305                 310                 315                 320

Phe Ser Gly Ser Gly Ser Gly Thr Asp Phe Thr Leu Thr Ile Ser Ser
                325                 330                 335

Leu Gln Pro Glu Asp Phe Ala Thr Tyr Tyr Cys Leu Gly Ser Tyr Ala
            340                 345                 350

Cys Ser Ser Ala Asp Cys Tyr Val Phe Gly Thr Gly Thr Lys Val Thr
        355                 360                 365

Val Leu Gly Gly Gly Gly Ser Glu Val Gln Leu Val Glu Ser Gly Gly
    370                 375                 380

Gly Leu Val Gln Pro Gly Gly Ser Leu Arg Leu Ser Cys Ala Ala Ser
385                 390                 395                 400

Ser Gly Ile Asp Phe Asn Ser Asn Tyr Tyr Met Cys Trp Val Arg Gln
                405                 410                 415

Ala Pro Gly Lys Gly Leu Glu Trp Ile Gly Cys Ile Tyr Val Gly Ser
            420                 425                 430

His Val Asn Thr Tyr Tyr Ala Asn Trp Ala Lys Gly Arg Phe Thr Ile
        435                 440                 445

Ser Arg Asp Asn Ser Lys Asn Thr Val Tyr Leu Gln Met Asn Ser Leu
    450                 455                 460

Arg Ala Glu Asp Thr Ala Val Tyr Tyr Cys Ala Thr Ser Gly Ser Ser
465                 470                 475                 480

Val Leu Tyr Phe Lys Phe Trp Gly Gln Gly Thr Leu Val Thr Val Ser
```

485                 490                 495

Ser

<210> SEQ ID NO 27
<211> LENGTH: 491
<212> TYPE: PRT
<213> ORGANISM: Artificial Sequence
<220> FEATURE:
<223> OTHER INFORMATION: artificial diabody sequence

<400> SEQUENCE: 27

Asp Ile Gln Met Thr Gln Ser Pro Ser Leu Ser Ala Ser Val Gly
1               5                   10                  15

Asp Arg Val Thr Ile Thr Cys Arg Ala Ser Gln Asp Val Asn Thr Ala
                20                  25                  30

Val Ala Trp Tyr Gln Gln Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
        50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Thr Gly Thr Lys Val Thr Val Leu Gly Gly Gly Gly
            100                 105                 110

Ser Glu Val Gln Leu Val Glu Ser Gly Gly Leu Val Gln Pro Gly
        115                 120                 125

Gly Ser Leu Arg Leu Ser Cys Ala Ala Ser Gly Phe Ser Leu Ser Ser
        130                 135                 140

Tyr Asp Met Ser Trp Val Arg Gln Ala Pro Gly Lys Gly Leu Ala Trp
145                 150                 155                 160

Ile Gly Ala Ser Tyr Ala Ser Gly Pro Thr Tyr Tyr Ala Ser Trp Ala
                165                 170                 175

Lys Gly Arg Phe Thr Ile Ser Arg Asp Asn Ser Lys Asn Thr Val Tyr
            180                 185                 190

Leu Gln Met Asn Ser Leu Arg Ala Glu Asp Thr Ala Thr Tyr Phe Cys
        195                 200                 205

Ala Arg Gly Gly Trp Thr Gly Thr Ser His Ser Asn Ile Trp Gly Gln
210                 215                 220

Gly Thr Leu Val Thr Val Ser Ser Gly Gly Gly Ser Gly Gly Gly
225                 230                 235                 240

Gly Ser Gly Gly Gly Ser Gly Gly Gly Ser Asp Ile Gln Met
            245                 250                 255

Thr Gln Ser Pro Ser Ser Leu Ser Ala Ser Val Gly Asp Arg Val Thr
        260                 265                 270

Ile Thr Cys Gln Ser Ser Gln Ser Val Phe Ser Asn Asn Tyr Leu Ala
            275                 280                 285

Trp Phe Gln Gln Lys Pro Gly Gln Ser Pro Lys Arg Leu Ile Tyr Ser
        290                 295                 300

Ala Ser Thr Leu Ala Ser Gly Val Pro Ser Arg Phe Ser Gly Ser Gly
305                 310                 315                 320

Ser Gly Thr Asp Phe Thr Leu Thr Ile Ser Ser Leu Gln Pro Glu Asp
                325                 330                 335

Phe Ala Thr Tyr Tyr Cys Leu Gly Ser Tyr Ala Cys Ser Ser Ala Asp
            340                 345                 350

```
Cys Tyr Val Phe Gly Thr Gly Thr Lys Val Thr Val Leu Gly Gly Gly
            355                 360                 365

Gly Gly Ser Glu Val Gln Leu Val Glu Ser Gly Gly Gly Leu Val Gln
        370                 375                 380

Pro Gly Ser Leu Arg Leu Ser Cys Ala Ala Ser Gly Phe Asn Ile
385                 390                 395                 400

Lys Asp Thr Tyr Ile His Trp Val Arg Gln Ala Pro Gly Lys Gly Leu
                    405                 410                 415

Glu Trp Val Ala Arg Ile Tyr Pro Thr Asn Gly Tyr Thr Arg Tyr Ala
            420                 425                 430

Asp Ser Val Lys Gly Arg Phe Thr Ile Ser Ala Asp Thr Ser Lys Asn
                435                 440                 445

Thr Ala Tyr Leu Gln Met Asn Ser Leu Arg Ala Glu Asp Thr Ala Val
    450                 455                 460

Tyr Tyr Cys Ser Arg Trp Gly Asp Gly Phe Tyr Ala Met Asp Tyr
465                 470                 475                 480

Trp Gly Gln Gly Thr Leu Val Thr Val Ser Ser
                485                 490
```

<210> SEQ ID NO 28
<211> LENGTH: 253
<212> TYPE: PRT
<213> ORGANISM: Artificial Sequence
<220> FEATURE:
<223> OTHER INFORMATION: artificial scFv sequence

<400> SEQUENCE: 28

```
Asp Ile Gln Met Thr Gln Ser Pro Ser Ser Leu Ser Ala Ser Val Gly
1               5                   10                  15

Asp Arg Val Thr Ile Thr Cys Gln Ser Ser Gln Ser Val Phe Ser Asn
                20                  25                  30

Asn Tyr Leu Ala Trp Tyr Gln Gln Lys Pro Gly Gln Ser Pro Lys Leu
            35                  40                  45

Leu Ile Tyr Ser Ala Ser Thr Leu Ala Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Leu Gly Ser Tyr Ala Cys
                85                  90                  95

Ser Ser Ala Asp Cys Tyr Val Phe Gly Thr Gly Thr Lys Val Thr Val
                100                 105                 110

Leu Gly Gly Gly Gly Ser Gly Gly Gly Gly Ser Gly Gly Gly Gly
            115                 120                 125

Ser Gly Gly Gly Gly Ser Glu Val Gln Leu Val Glu Ser Gly Gly Gly
        130                 135                 140

Leu Val Gln Pro Gly Gly Ser Leu Arg Leu Ser Cys Ala Ala Ser Gly
145                 150                 155                 160

Phe Ser Leu Ser Ser Tyr Asp Met Ser Trp Val Arg Gln Ala Pro Gly
                165                 170                 175

Lys Gly Leu Glu Trp Ile Gly Ala Ser Tyr Ala Ser Gly Pro Thr Tyr
                180                 185                 190

Tyr Ala Ser Trp Ala Lys Gly Arg Phe Thr Ile Ser Arg Asp Asn Ser
            195                 200                 205

Lys Asn Thr Val Tyr Leu Gln Met Asn Ser Leu Arg Ala Glu Asp Thr
    210                 215                 220
```

```
Ala Thr Tyr Phe Cys Ala Arg Gly Gly Trp Thr Gly Thr Ser His Ser
225                 230                 235                 240

Asn Ile Trp Gly Gln Gly Thr Leu Val Thr Val Ser Ser
                245                 250

<210> SEQ ID NO 29
<211> LENGTH: 253
<212> TYPE: PRT
<213> ORGANISM: Artificial Sequence
<220> FEATURE:
<223> OTHER INFORMATION: artificial scFv sequence

<400> SEQUENCE: 29

Asp Ile Gln Met Thr Gln Ser Pro Ser Ser Leu Ser Ala Ser Val Gly
1               5                   10                  15

Asp Arg Val Thr Ile Thr Cys Gln Ser Ser Gln Ser Val Phe Ser Asn
            20                  25                  30

Asn Tyr Leu Ala Trp Tyr Gln Gln Lys Pro Gly Gln Ser Pro Lys Arg
        35                  40                  45

Leu Ile Tyr Ser Ala Ser Thr Leu Ala Ser Gly Val Pro Ser Arg Phe
    50                  55                  60

Ser Gly Ser Gly Ser Gly Thr His Phe Thr Leu Thr Ile Ser Ser Leu
65                  70                  75                  80

Gln Pro Glu Asp Phe Ala Thr Tyr Tyr Cys Leu Gly Ser Tyr Ala Cys
                85                  90                  95

Ser Ser Ala Asp Cys Tyr Val Phe Gly Thr Gly Thr Lys Val Thr Val
            100                 105                 110

Leu Gly Gly Gly Gly Ser Gly Gly Gly Ser Gly Gly Gly Gly
        115                 120                 125

Ser Gly Gly Gly Gly Ser Glu Val Gln Leu Val Glu Ser Gly Gly Gly
    130                 135                 140

Leu Val Gln Pro Gly Gly Ser Leu Arg Leu Ser Cys Ala Ala Ser Gly
145                 150                 155                 160

Phe Ser Leu Ser Ser Tyr Asp Met Ser Trp Val Arg Gln Ala Pro Gly
                165                 170                 175

Lys Gly Leu Glu Trp Ile Gly Ala Ser Tyr Ala Ser Gly Pro Thr Tyr
            180                 185                 190

Tyr Ala Ser Trp Ala Lys Gly Arg Phe Thr Ile Ser Arg Asp Asn Ser
        195                 200                 205

Lys Asn Thr Val Tyr Leu Gln Met Asn Ser Leu Arg Ala Glu Asp Thr
    210                 215                 220

Ala Thr Tyr Phe Cys Ala Arg Gly Gly Trp Thr Gly Thr Ser His Ser
225                 230                 235                 240

Asn Ile Trp Gly Gln Gly Thr Leu Val Thr Val Ser Ser
                245                 250

<210> SEQ ID NO 30
<211> LENGTH: 253
<212> TYPE: PRT
<213> ORGANISM: Artificial Sequence
<220> FEATURE:
<223> OTHER INFORMATION: artificial scFv sequence

<400> SEQUENCE: 30

Asp Ile Gln Met Thr Gln Ser Pro Ser Ser Leu Ser Ala Ser Val Gly
1               5                   10                  15

Asp Arg Val Thr Ile Thr Cys Gln Ser Ser Gln Ser Val Phe Ser Asn
```

```
Asn Tyr Leu Ala Trp Tyr Gln Gln Lys Pro Gly Gln Ser Pro Lys Arg
             35                  40                  45

Leu Ile Tyr Ser Ala Ser Thr Leu Ala Ser Gly Val Pro Ser Arg Phe
 50                  55                  60

Ser Gly Ser Gly Ser Gly Thr Asp Phe Thr Leu Thr Ile Ser Ser Leu
 65                  70                  75                  80

Gln Pro Glu Asp Phe Ala Thr Tyr Tyr Cys Leu Gly Ser Tyr Ala Cys
                 85                  90                  95

Ser Ser Ala Asp Cys Tyr Val Phe Gly Thr Gly Thr Lys Val Thr Val
                100                 105                 110

Leu Gly Gly Gly Gly Ser Gly Gly Gly Gly Ser Gly Gly Gly Gly
            115                 120                 125

Ser Gly Gly Gly Gly Ser Glu Val Gln Leu Val Glu Ser Gly Gly Gly
            130                 135                 140

Leu Val Gln Pro Gly Gly Ser Leu Arg Leu Ser Cys Ala Ala Ser Gly
145                 150                 155                 160

Phe Ser Leu Ser Ser Tyr Asp Met Ser Trp Val Arg Gln Ala Pro Gly
                165                 170                 175

Lys Gly Leu Glu Trp Ile Gly Ala Ser Tyr Ala Ser Gly Pro Thr Tyr
            180                 185                 190

Tyr Ala Ser Trp Ala Lys Gly Arg Phe Thr Ile Ser Arg Asp Asn Ser
        195                 200                 205

Lys Asn Thr Val Tyr Leu Gln Met Asn Ser Leu Arg Ala Glu Asp Thr
210                 215                 220

Ala Thr Tyr Phe Cys Ala Arg Gly Gly Trp Thr Gly Thr Ser His Ser
225                 230                 235                 240

Asn Ile Trp Gly Gln Gly Thr Leu Val Thr Val Ser Ser
                245                 250

<210> SEQ ID NO 31
<211> LENGTH: 253
<212> TYPE: PRT
<213> ORGANISM: Artificial Sequence
<220> FEATURE:
<223> OTHER INFORMATION: artificial scFv sequence

<400> SEQUENCE: 31

Asp Ile Gln Met Thr Gln Ser Pro Ser Ser Leu Ser Ala Ser Val Gly
 1               5                  10                  15

Asp Arg Val Thr Ile Thr Cys Gln Ser Ser Gln Ser Val Phe Ser Asn
             20                  25                  30

Asn Tyr Leu Ala Trp Tyr Gln Gln Lys Pro Gly Gln Ser Pro Lys Leu
             35                  40                  45

Leu Ile Tyr Ser Ala Ser Thr Leu Ala Ser Gly Val Pro Ser Arg Phe
 50                  55                  60

Ser Gly Ser Gly Ser Gly Thr His Phe Thr Leu Thr Ile Ser Ser Leu
 65                  70                  75                  80

Gln Pro Glu Asp Phe Ala Thr Tyr Tyr Cys Leu Gly Ser Tyr Ala Cys
                 85                  90                  95

Ser Ser Ala Asp Cys Tyr Val Phe Gly Thr Gly Thr Lys Val Thr Val
                100                 105                 110

Leu Gly Gly Gly Gly Ser Gly Gly Gly Gly Ser Gly Gly Gly Gly
            115                 120                 125

Ser Gly Gly Gly Gly Ser Glu Val Gln Leu Val Glu Ser Gly Gly Gly
```

```
            130                 135                 140
Leu Val Gln Pro Gly Gly Ser Leu Arg Leu Ser Cys Ala Ala Ser Gly
145                 150                 155                 160

Phe Ser Leu Ser Ser Tyr Asp Met Ser Trp Val Arg Gln Ala Pro Gly
                165                 170                 175

Lys Gly Leu Glu Trp Ile Gly Ala Ser Tyr Ala Ser Gly Pro Thr Tyr
            180                 185                 190

Tyr Ala Ser Trp Ala Lys Gly Arg Phe Thr Ile Ser Arg Asp Asn Ser
                195                 200                 205

Lys Asn Thr Val Tyr Leu Gln Met Asn Ser Leu Arg Ala Glu Asp Thr
            210                 215                 220

Ala Thr Tyr Phe Cys Ala Arg Gly Gly Trp Thr Gly Thr Ser His Ser
225                 230                 235                 240

Asn Ile Trp Gly Gln Gly Thr Leu Val Thr Val Ser Ser
                245                 250

<210> SEQ ID NO 32
<211> LENGTH: 253
<212> TYPE: PRT
<213> ORGANISM: Artificial Sequence
<220> FEATURE:
<223> OTHER INFORMATION: artificial scFv sequence

<400> SEQUENCE: 32

Asp Ile Gln Met Thr Gln Ser Pro Ser Ser Leu Ser Ala Ser Val Gly
1               5                   10                  15

Asp Arg Val Thr Ile Thr Cys Gln Ser Ser Gln Ser Val Phe Ser Asn
            20                  25                  30

Asn Tyr Leu Ala Trp Tyr Gln Gln Lys Pro Gly Gln Ser Pro Lys Arg
        35                  40                  45

Leu Ile Tyr Ser Ala Ser Thr Leu Ala Ser Gly Val Pro Ser Arg Phe
    50                  55                  60

Ser Gly Ser Gly Ser Gly Thr His Phe Thr Leu Thr Ile Ser Ser Leu
65                  70                  75                  80

Gln Pro Glu Asp Phe Ala Thr Tyr Tyr Cys Leu Gly Ser Tyr Ala Cys
                85                  90                  95

Ser Ser Ala Asp Cys Tyr Val Phe Gly Thr Gly Thr Lys Val Thr Val
            100                 105                 110

Leu Gly Gly Gly Gly Ser Gly Gly Gly Ser Gly Gly Gly Gly
        115                 120                 125

Ser Gly Gly Gly Gly Ser Glu Val Gln Leu Val Glu Ser Gly Gly Gly
        130                 135                 140

Leu Val Gln Pro Gly Gly Ser Leu Arg Leu Ser Cys Ala Ala Ser Gly
145                 150                 155                 160

Phe Ser Leu Ser Ser Tyr Asp Met Ser Trp Val Arg Gln Ala Pro Gly
                165                 170                 175

Lys Gly Leu Glu Trp Ile Gly Ala Ser Tyr Ala Ser Gly Pro Thr Tyr
            180                 185                 190

Tyr Ala Ser Trp Ala Lys Gly Arg Phe Thr Ile Ser Arg Asp Asn Ser
                195                 200                 205

Lys Asn Thr Val Tyr Leu Gln Met Asn Ser Leu Arg Ala Glu Asp Thr
            210                 215                 220

Ala Val Tyr Tyr Cys Ala Arg Gly Gly Trp Thr Gly Thr Ser His Ser
225                 230                 235                 240

Asn Ile Trp Gly Gln Gly Thr Leu Val Thr Val Ser Ser
```

<210> SEQ ID NO 33
<211> LENGTH: 253
<212> TYPE: PRT
<213> ORGANISM: Artificial Sequence
<220> FEATURE:
<223> OTHER INFORMATION: artificial scFv sequence

<400> SEQUENCE: 33

```
Asp Ile Gln Met Thr Gln Ser Pro Ser Ser Leu Ser Ala Ser Val Gly
1               5                   10                  15

Asp Arg Val Thr Ile Thr Cys Gln Ser Ser Gln Ser Val Phe Ser Asn
            20                  25                  30

Asn Tyr Leu Ala Trp Tyr Gln Gln Lys Pro Gly Gln Ser Pro Lys Arg
        35                  40                  45

Leu Ile Tyr Ser Ala Ser Thr Leu Ala Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Leu Gly Ser Tyr Ala Cys
                85                  90                  95

Ser Ser Ala Asp Cys Tyr Val Phe Gly Thr Gly Thr Lys Val Thr Val
            100                 105                 110

Leu Gly Gly Gly Gly Ser Gly Gly Gly Ser Gly Gly Gly Gly
        115                 120                 125

Ser Gly Gly Gly Gly Ser Glu Val Gln Leu Val Glu Ser Gly Gly Gly
130                 135                 140

Leu Val Gln Pro Gly Gly Ser Leu Arg Leu Ser Cys Ala Ala Ser Gly
145                 150                 155                 160

Phe Ser Leu Ser Ser Tyr Asp Met Ser Trp Val Arg Gln Ala Pro Gly
                165                 170                 175

Lys Gly Leu Glu Trp Ile Gly Ala Ser Tyr Ala Ser Gly Pro Thr Tyr
            180                 185                 190

Tyr Ala Ser Trp Ala Lys Gly Arg Phe Thr Ile Ser Arg Asp Asn Ser
        195                 200                 205

Lys Asn Thr Val Tyr Leu Gln Met Asn Ser Leu Arg Ala Glu Asp Thr
    210                 215                 220

Ala Val Tyr Tyr Cys Ala Arg Gly Gly Trp Thr Gly Thr Ser His Ser
225                 230                 235                 240

Asn Ile Trp Gly Gln Gly Thr Leu Val Thr Val Ser Ser
                245                 250
```

<210> SEQ ID NO 34
<211> LENGTH: 253
<212> TYPE: PRT
<213> ORGANISM: Artificial Sequence
<220> FEATURE:
<223> OTHER INFORMATION: artificial scFv sequence

<400> SEQUENCE: 34

```
Asp Ile Gln Met Thr Gln Ser Pro Ser Ser Leu Ser Ala Ser Val Gly
1               5                   10                  15

Asp Arg Val Thr Ile Thr Cys Gln Ser Ser Gln Ser Val Phe Ser Asn
            20                  25                  30

Asn Tyr Leu Ala Trp Tyr Gln Gln Lys Pro Gly Gln Ser Pro Lys Leu
        35                  40                  45
```

```
Leu Ile Tyr Ser Ala Ser Thr Leu Ala Ser Gly Val Pro Ser Arg Phe
 50                  55                  60

Ser Gly Ser Gly Ser Gly Thr His Phe Thr Leu Thr Ile Ser Ser Leu
 65                  70                  75                  80

Gln Pro Glu Asp Phe Ala Thr Tyr Tyr Cys Leu Gly Ser Tyr Ala Cys
                 85                  90                  95

Ser Ser Ala Asp Cys Tyr Val Phe Gly Thr Gly Thr Lys Val Thr Val
                100                 105                 110

Leu Gly Gly Gly Gly Ser Gly Gly Gly Ser Gly Gly Gly Gly
            115                 120                 125

Ser Gly Gly Gly Ser Glu Val Gln Leu Val Glu Ser Gly Gly Gly
    130                 135                 140

Leu Val Gln Pro Gly Gly Ser Leu Arg Leu Ser Cys Ala Ala Ser Gly
145                 150                 155                 160

Phe Ser Leu Ser Ser Tyr Asp Met Ser Trp Val Arg Gln Ala Pro Gly
                165                 170                 175

Lys Gly Leu Glu Trp Ile Gly Ala Ser Tyr Ala Ser Gly Pro Thr Tyr
                180                 185                 190

Tyr Ala Ser Trp Ala Lys Gly Arg Phe Thr Ile Ser Arg Asp Asn Ser
                195                 200                 205

Lys Asn Thr Val Tyr Leu Gln Met Asn Ser Leu Arg Ala Glu Asp Thr
            210                 215                 220

Ala Val Tyr Tyr Cys Ala Arg Gly Gly Trp Thr Gly Thr Ser His Ser
225                 230                 235                 240

Asn Ile Trp Gly Gln Gly Thr Leu Val Thr Val Ser Ser
                245                 250

<210> SEQ ID NO 35
<211> LENGTH: 253
<212> TYPE: PRT
<213> ORGANISM: Artificial Sequence
<220> FEATURE:
<223> OTHER INFORMATION: artificial scFv sequence

<400> SEQUENCE: 35

Asp Ile Gln Met Thr Gln Ser Pro Ser Ser Leu Ser Ala Ser Val Gly
  1               5                  10                  15

Asp Arg Val Thr Ile Thr Cys Gln Ser Ser Gln Ser Val Phe Ser Asn
                 20                  25                  30

Asn Tyr Leu Ala Trp Tyr Gln Gln Lys Pro Gly Gln Ser Pro Lys Arg
             35                  40                  45

Leu Ile Tyr Ser Ala Ser Thr Leu Ala Ser Gly Val Pro Ser Arg Phe
 50                  55                  60

Ser Gly Ser Gly Ser Gly Thr Asp Phe Thr Leu Thr Ile Ser Ser Leu
 65                  70                  75                  80

Gln Pro Glu Asp Phe Ala Thr Tyr Tyr Cys Leu Gly Ser Tyr Ala Cys
                 85                  90                  95

Ser Ser Ala Asp Cys Tyr Val Phe Gly Thr Gly Thr Lys Val Thr Val
                100                 105                 110

Leu Gly Gly Gly Gly Ser Gly Gly Gly Ser Gly Gly Gly Gly
            115                 120                 125

Ser Gly Gly Gly Ser Glu Val Gln Leu Val Glu Ser Gly Gly Gly
    130                 135                 140

Leu Val Gln Pro Gly Gly Ser Leu Arg Leu Ser Cys Ala Ala Ser Gly
145                 150                 155                 160
```

```
Phe Ser Leu Ser Ser Tyr Asp Met Ser Trp Val Arg Gln Ala Pro Gly
            165                 170                 175

Lys Gly Leu Ala Trp Ile Gly Ala Ser Tyr Ala Ser Gly Pro Thr Tyr
        180                 185                 190

Tyr Ala Ser Trp Ala Lys Gly Arg Phe Thr Ile Ser Arg Asp Asn Ser
        195                 200                 205

Lys Asn Thr Val Tyr Leu Gln Met Asn Ser Leu Arg Ala Glu Asp Thr
        210                 215                 220

Ala Val Tyr Tyr Cys Ala Arg Gly Gly Trp Thr Gly Thr Ser His Ser
225                 230                 235                 240

Asn Ile Trp Gly Gln Gly Thr Leu Val Thr Val Ser Ser
                245                 250
```

<210> SEQ ID NO 36
<211> LENGTH: 253
<212> TYPE: PRT
<213> ORGANISM: Artificial Sequence
<220> FEATURE:
<223> OTHER INFORMATION: artificial scFv sequence

<400> SEQUENCE: 36

```
Asp Ile Gln Met Thr Gln Ser Pro Ser Ser Leu Ser Ala Ser Val Gly
1               5                   10                  15

Asp Arg Val Thr Ile Thr Cys Gln Ser Ser Gln Ser Val Phe Ser Asn
            20                  25                  30

Asn Tyr Leu Ala Trp Phe Gln Gln Lys Pro Gly Gln Ser Pro Lys Arg
        35                  40                  45

Leu Ile Tyr Ser Ala Ser Thr Leu Ala Ser Gly Val Pro Ser Arg Phe
50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Leu Gly Ser Tyr Ala Cys
                85                  90                  95

Ser Ser Ala Asp Cys Tyr Val Phe Gly Thr Gly Thr Lys Val Thr Val
            100                 105                 110

Leu Gly Gly Gly Gly Ser Gly Gly Gly Ser Gly Gly Gly Gly
        115                 120                 125

Ser Gly Gly Gly Gly Ser Glu Val Gln Leu Val Glu Ser Gly Gly Gly
    130                 135                 140

Leu Val Gln Pro Gly Gly Ser Leu Arg Leu Ser Cys Ala Ala Ser Gly
145                 150                 155                 160

Phe Ser Leu Ser Ser Tyr Asp Met Ser Trp Val Arg Gln Ala Pro Gly
            165                 170                 175

Lys Gly Leu Glu Trp Ile Gly Ala Ser Tyr Ala Ser Gly Pro Thr Tyr
        180                 185                 190

Tyr Ala Ser Trp Ala Lys Gly Arg Phe Thr Ile Ser Arg Asp Asn Ser
        195                 200                 205

Lys Asn Thr Val Tyr Leu Gln Met Asn Ser Leu Arg Ala Glu Asp Thr
        210                 215                 220

Ala Val Tyr Tyr Cys Ala Arg Gly Gly Trp Thr Gly Thr Ser His Ser
225                 230                 235                 240

Asn Ile Trp Gly Gln Gly Thr Leu Val Thr Val Ser Ser
                245                 250
```

<210> SEQ ID NO 37
<211> LENGTH: 253

```
<212> TYPE: PRT
<213> ORGANISM: Artificial Sequence
<220> FEATURE:
<223> OTHER INFORMATION: artificial scFv sequence

<400> SEQUENCE: 37

Asp Ile Gln Met Thr Gln Ser Pro Ser Ser Leu Ser Ala Ser Val Gly
1               5                   10                  15

Asp Arg Val Thr Ile Thr Cys Gln Ser Ser Gln Ser Val Phe Ser Asn
            20                  25                  30

Asn Tyr Leu Ala Trp Tyr Gln Gln Lys Pro Gly Lys Ala Pro Lys Arg
        35                  40                  45

Leu Ile Tyr Ser Ala Ser Thr Leu Ala Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Leu Gly Ser Tyr Ala Cys
                85                  90                  95

Ser Ser Ala Asp Cys Tyr Val Phe Gly Thr Gly Thr Lys Val Thr Val
            100                 105                 110

Leu Gly Gly Gly Gly Ser Gly Gly Gly Ser Gly Gly Gly Gly
            115                 120                 125

Ser Gly Gly Gly Gly Ser Glu Val Gln Leu Val Glu Ser Gly Gly Gly
            130                 135                 140

Leu Val Gln Pro Gly Gly Ser Leu Arg Leu Ser Cys Ala Ala Ser Gly
145                 150                 155                 160

Phe Ser Leu Ser Ser Tyr Asp Met Ser Trp Val Arg Gln Ala Pro Gly
                165                 170                 175

Lys Gly Leu Ala Trp Ile Gly Ala Ser Tyr Ala Ser Gly Pro Thr Tyr
            180                 185                 190

Tyr Ala Ser Trp Ala Lys Gly Arg Phe Thr Ile Ser Arg Asp Asn Ser
        195                 200                 205

Lys Asn Thr Val Tyr Leu Gln Met Asn Ser Leu Arg Ala Glu Asp Thr
210                 215                 220

Ala Val Tyr Tyr Cys Ala Arg Gly Gly Trp Thr Gly Thr Ser His Ser
225                 230                 235                 240

Asn Ile Trp Gly Gln Gly Thr Leu Val Thr Val Ser Ser
                245                 250

<210> SEQ ID NO 38
<211> LENGTH: 253
<212> TYPE: PRT
<213> ORGANISM: Artificial Sequence
<220> FEATURE:
<223> OTHER INFORMATION: artificial scFv sequence

<400> SEQUENCE: 38

Asp Ile Gln Met Thr Gln Ser Pro Ser Ser Leu Ser Ala Ser Val Gly
1               5                   10                  15

Asp Arg Val Thr Ile Thr Cys Gln Ser Ser Gln Ser Val Phe Ser Asn
            20                  25                  30

Asn Tyr Leu Ala Trp Tyr Gln Gln Lys Pro Gly Gln Ser Pro Lys Lys
        35                  40                  45

Leu Ile Tyr Ser Ala Ser Thr Leu Ala Ser Gly Val Pro Ser Arg Phe
    50                  55                  60

Ser Gly Ser Gly Ser Gly Thr Asp Phe Thr Leu Thr Ile Ser Ser Leu
65                  70                  75                  80
```

Gln Pro Glu Asp Phe Ala Thr Tyr Tyr Cys Leu Gly Ser Tyr Ala Cys
                85                  90                  95

Ser Ser Ala Asp Cys Tyr Val Phe Gly Thr Gly Thr Lys Val Thr Val
            100                 105                 110

Leu Gly Gly Gly Gly Ser Gly Gly Gly Ser Gly Gly Gly Gly
        115                 120                 125

Ser Gly Gly Gly Ser Glu Val Gln Leu Val Glu Ser Gly Gly Gly
    130                 135                 140

Leu Val Gln Pro Gly Gly Ser Leu Arg Leu Ser Cys Ala Ala Ser Gly
145                 150                 155                 160

Phe Ser Leu Ser Ser Tyr Asp Met Ser Trp Val Arg Gln Ala Pro Gly
                165                 170                 175

Lys Gly Leu Ala Trp Ile Gly Ala Ser Tyr Ala Ser Gly Pro Thr Tyr
            180                 185                 190

Tyr Ala Ser Trp Ala Lys Gly Arg Phe Thr Ile Ser Arg Asp Asn Ser
        195                 200                 205

Lys Asn Thr Val Tyr Leu Gln Met Asn Ser Leu Arg Ala Glu Asp Thr
    210                 215                 220

Ala Val Tyr Tyr Cys Ala Arg Gly Gly Trp Thr Gly Thr Ser His Ser
225                 230                 235                 240

Asn Ile Trp Gly Gln Gly Thr Leu Val Thr Val Ser Ser
                245                 250

<210> SEQ ID NO 39
<211> LENGTH: 253
<212> TYPE: PRT
<213> ORGANISM: Artificial Sequence
<220> FEATURE:
<223> OTHER INFORMATION: artificial scFv sequence

<400> SEQUENCE: 39

Asp Ile Gln Met Thr Gln Ser Pro Ser Ser Leu Ser Ala Ser Val Gly
1               5                   10                  15

Asp Arg Val Thr Ile Thr Cys Gln Ser Ser Gln Ser Val Phe Ser Asn
            20                  25                  30

Asn Tyr Leu Ala Trp Tyr Gln Gln Lys Pro Gly Gln Ser Pro Lys Arg
        35                  40                  45

Leu Ile Tyr Ser Ala Ser Thr Leu Ala Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Leu Gly Ser Tyr Ala Cys
                85                  90                  95

Ser Ser Ala Asp Cys Tyr Val Phe Gly Thr Gly Thr Lys Val Thr Val
            100                 105                 110

Leu Gly Gly Gly Gly Ser Gly Gly Gly Ser Gly Gly Gly Gly
        115                 120                 125

Ser Gly Gly Gly Ser Glu Val Gln Leu Val Glu Ser Gly Gly Gly
    130                 135                 140

Leu Val Gln Pro Gly Gly Ser Leu Arg Leu Ser Cys Ala Ala Ser Gly
145                 150                 155                 160

Phe Ser Leu Ser Ser Tyr Asp Met Ser Trp Val Arg Gln Ala Pro Gly
                165                 170                 175

Lys Gly Leu Ala Trp Ile Gly Ala Ser Tyr Ala Ser Gly Pro Thr Tyr
            180                 185                 190

Tyr Ala Ser Trp Ala Lys Gly Arg Phe Thr Ile Ser Arg Asp Asn Ser
            195                 200                 205

Lys Asn Thr Val Tyr Leu Gln Met Asn Ser Leu Arg Ala Glu Asp Thr
    210                 215                 220

Ala Thr Tyr Phe Cys Ala Arg Gly Gly Trp Thr Gly Thr Ser His Ser
225                 230                 235                 240

Asn Ile Trp Gly Gln Gly Thr Leu Val Thr Val Ser Ser
                245                 250

<210> SEQ ID NO 40
<211> LENGTH: 253
<212> TYPE: PRT
<213> ORGANISM: Artificial Sequence
<220> FEATURE:
<223> OTHER INFORMATION: artificial scFv sequence

<400> SEQUENCE: 40

Asp Ile Gln Met Thr Gln Ser Pro Ser Ser Leu Ser Ala Ser Val Gly
1               5                   10                  15

Asp Arg Val Thr Ile Thr Cys Gln Ser Ser Gln Ser Val Phe Ser Asn
            20                  25                  30

Asn Tyr Leu Ala Trp Tyr Gln Gln Lys Pro Gly Gln Ser Pro Lys Arg
        35                  40                  45

Leu Ile Tyr Ser Ala Ser Thr Leu Ala Ser Gly Val Pro Ser Arg Phe
50                  55                  60

Ser Gly Ser Gly Ser Gly Thr Gln Phe Thr Leu Thr Ile Ser Ser Leu
65                  70                  75                  80

Gln Pro Glu Asp Phe Ala Thr Tyr Tyr Cys Leu Gly Ser Tyr Ala Cys
                85                  90                  95

Ser Ser Ala Asp Cys Tyr Val Phe Gly Thr Gly Thr Lys Val Thr Val
            100                 105                 110

Leu Gly Gly Gly Gly Ser Gly Gly Gly Gly Ser Gly Gly Gly Gly
        115                 120                 125

Ser Gly Gly Gly Gly Ser Glu Val Gln Leu Val Glu Ser Gly Gly Gly
    130                 135                 140

Leu Val Gln Pro Gly Gly Ser Leu Arg Leu Ser Cys Ala Ala Ser Gly
145                 150                 155                 160

Phe Ser Leu Ser Ser Tyr Asp Met Ser Trp Val Arg Gln Ala Pro Gly
                165                 170                 175

Lys Gly Leu Ala Trp Ile Gly Ala Ser Tyr Ala Ser Gly Pro Thr Tyr
            180                 185                 190

Tyr Ala Ser Trp Ala Lys Gly Arg Phe Thr Ile Ser Arg Asp Asn Ser
        195                 200                 205

Lys Asn Thr Val Tyr Leu Gln Met Asn Ser Leu Arg Ala Glu Asp Thr
    210                 215                 220

Ala Val Tyr Tyr Cys Ala Arg Gly Gly Trp Thr Gly Thr Ser His Ser
225                 230                 235                 240

Asn Ile Trp Gly Gln Gly Thr Leu Val Thr Val Ser Ser
                245                 250

<210> SEQ ID NO 41
<211> LENGTH: 253
<212> TYPE: PRT
<213> ORGANISM: Artificial Sequence
<220> FEATURE:
<223> OTHER INFORMATION: artificial scFv sequence

<400> SEQUENCE: 41

Asp Ile Gln Met Thr Gln Ser Pro Ser Ser Leu Ser Ala Ser Val Gly
1               5                   10                  15

Asp Arg Val Thr Ile Thr Cys Gln Ser Ser Gln Ser Val Phe Ser Asn
            20                  25                  30

Asn Tyr Leu Ala Trp Tyr Gln Gln Lys Pro Gly Gln Ser Pro Lys Arg
        35                  40                  45

Leu Ile Tyr Ser Ala Ser Thr Leu Ala Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Leu Gly Ser Tyr Ala Cys
                85                  90                  95

Ser Ser Ala Asp Cys Tyr Val Phe Gly Thr Gly Thr Lys Val Thr Val
            100                 105                 110

Leu Gly Gly Gly Gly Ser Gly Gly Gly Ser Gly Gly Gly Gly
        115                 120                 125

Ser Gly Gly Gly Ser Glu Val Gln Leu Val Glu Ser Gly Gly
    130                 135                 140

Leu Val Gln Pro Gly Gly Ser Leu Arg Leu Ser Cys Ala Val Ser Gly
145                 150                 155                 160

Phe Ser Leu Ser Ser Tyr Asp Met Ser Trp Val Arg Gln Ala Pro Gly
                165                 170                 175

Lys Gly Leu Ala Trp Ile Gly Ala Ser Tyr Ala Ser Gly Pro Thr Tyr
            180                 185                 190

Tyr Ala Ser Trp Ala Lys Gly Arg Phe Thr Ile Ser Arg Asp Asn Ser
        195                 200                 205

Lys Asn Thr Val Tyr Leu Gln Met Asn Ser Leu Arg Ala Glu Asp Thr
    210                 215                 220

Ala Val Tyr Tyr Cys Ala Arg Gly Gly Trp Thr Gly Thr Ser His Ser
225                 230                 235                 240

Asn Ile Trp Gly Gln Gly Thr Leu Val Thr Val Ser Ser
                245                 250

<210> SEQ ID NO 42
<211> LENGTH: 253
<212> TYPE: PRT
<213> ORGANISM: Artificial Sequence
<220> FEATURE:
<223> OTHER INFORMATION: artificial scFv sequence

<400> SEQUENCE: 42

Asp Ile Gln Met Thr Gln Ser Pro Ser Ser Leu Ser Ala Ser Val Gly
1               5                   10                  15

Asp Arg Val Thr Ile Thr Cys Gln Ser Ser Gln Ser Val Phe Ser Asn
            20                  25                  30

Asn Tyr Leu Ala Trp Phe Gln Gln Lys Pro Gly Lys Ala Pro Lys Arg
        35                  40                  45

Leu Ile Tyr Ser Ala Ser Thr Leu Ala Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Leu Gly Ser Tyr Ala Cys
                85                  90                  95

Ser Ser Ala Asp Cys Tyr Val Phe Gly Thr Gly Thr Lys Val Thr Val

-continued

```
                100             105             110
Leu Gly Gly Gly Gly Ser Gly Gly Gly Ser Gly Gly Gly
        115             120             125

Ser Gly Gly Gly Ser Glu Val Gln Leu Val Glu Ser Gly Gly Gly
        130             135             140

Leu Val Gln Pro Gly Gly Ser Leu Arg Leu Ser Cys Ala Ala Ser Gly
145             150             155             160

Phe Ser Leu Ser Ser Tyr Asp Met Ser Trp Val Arg Gln Ala Pro Gly
                165             170             175

Lys Gly Leu Glu Trp Ile Gly Ala Ser Tyr Ala Ser Gly Pro Thr Tyr
            180             185             190

Tyr Ala Ser Trp Ala Lys Gly Arg Phe Thr Ile Ser Arg Asp Asn Ser
            195             200             205

Lys Asn Thr Val Tyr Leu Gln Met Asn Ser Leu Arg Ala Glu Asp Thr
    210             215             220

Ala Val Tyr Tyr Cys Ala Arg Gly Gly Trp Thr Gly Thr Ser His Ser
225             230             235             240

Asn Ile Trp Gly Gln Gly Thr Leu Val Thr Val Ser Ser
                245             250

<210> SEQ ID NO 43
<211> LENGTH: 5
<212> TYPE: PRT
<213> ORGANISM: Artificial sequence
<220> FEATURE:
<223> OTHER INFORMATION: CD3epsilon epitope with X = L from human and
      X = M from cynomolgus
<220> FEATURE:
<221> NAME/KEY: MISC_FEATURE
<222> LOCATION: (4)..(4)
<223> OTHER INFORMATION: X is selected from L and M

<400> SEQUENCE: 43

Phe Ser Glu Xaa Glu
1               5

<210> SEQ ID NO 44
<211> LENGTH: 5
<212> TYPE: PRT
<213> ORGANISM: Artificial sequence
<220> FEATURE:
<223> OTHER INFORMATION: CD3epsilon epitope of human and non-chimpanzee
      primates

<400> SEQUENCE: 44

Gln Asp Gly Asn Glu
1               5
```